US012565642B2

(12) United States Patent
Fuchs et al.

(10) Patent No.: US 12,565,642 B2
(45) Date of Patent: *Mar. 3, 2026

(54) ENGINEERED DNASE ENZYMES FOR THROMBOSIS THERAPY

(71) Applicant: NEUTROLIS, INC., Cambridge, MA (US)

(72) Inventors: Tobias A. Fuchs, Cambridge, MA (US); Abdul Hakkim R., Cambridge, MA (US)

(73) Assignee: Neutrolis, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/497,106

(22) Filed: Oct. 30, 2023

(65) Prior Publication Data

US 2024/0191218 A1     Jun. 13, 2024

Related U.S. Application Data

(63) Continuation of application No. 17/210,129, filed on Mar. 23, 2021, now Pat. No. 11,840,712, which is a continuation of application No. 16/697,502, filed on Nov. 27, 2019, now Pat. No. 10,988,746, which is a continuation of application No. PCT/US2019/055178, filed on Oct. 8, 2019.

(60) Provisional application No. 62/846,904, filed on May 13, 2019, provisional application No. 62/808,601, filed on Feb. 21, 2019, provisional application No. 62/779,104, filed on Dec. 13, 2018, provisional application No. 62/775,563, filed on Dec. 5, 2018, provisional application No. 62/742,682, filed on Oct. 8, 2018.

(51) Int. Cl.
| | |
|---|---|
| *C12N 9/22* | (2006.01) |
| *A61K 9/00* | (2006.01) |
| *A61K 38/47* | (2006.01) |
| *C07K 14/76* | (2006.01) |
| *C12P 21/02* | (2006.01) |

(52) U.S. Cl.
CPC .............. *C12N 9/22* (2013.01); *A61K 9/0029* (2013.01); *A61K 38/47* (2013.01); *C07K 14/76* (2013.01); *C12P 21/02* (2013.01); *C12Y 301/21001* (2013.01); *C07K 2319/31* (2013.01)

(58) Field of Classification Search
CPC .......... C12N 9/22; C12N 15/81; C12N 15/62; C12N 15/85; A61K 9/0029; A61K 38/47; A61K 38/46; C07K 14/76; C07K 2319/31; C07K 2319/50; C12P 21/02; C12Y 301/21001; A61P 1/00; A61P 7/00; A61P 17/02; A61P 29/00; A61P 35/00
See application file for complete search history.

(56) References Cited

U.S. PATENT DOCUMENTS

| | | | |
|---|---|---|---|
| 6,270,989 | B1 | 8/2001 | Treco et al. |
| 6,482,626 | B2 | 11/2002 | Baker et al. |
| 6,656,685 | B2 | 12/2003 | Utermohlen et al. |
| 7,612,032 | B2 | 11/2009 | Genkin et al. |
| 8,388,951 | B2 | 3/2013 | Genkin et al. |
| 8,431,123 | B2 | 4/2013 | Genkin et al. |
| 8,535,663 | B2 | 9/2013 | Genkin et al. |
| 8,796,004 | B2 | 8/2014 | Genkin et al. |
| 8,916,151 | B2 | 12/2014 | Genkin et al. |
| 9,072,733 | B2 | 7/2015 | Genkin et al. |
| 9,149,513 | B2 | 10/2015 | Bartoov et al. |
| 9,198,957 | B2 | 12/2015 | Ratner et al. |
| 9,205,133 | B2 | 12/2015 | Dawson et al. |
| 9,248,166 | B2 | 2/2016 | Gerkin et al. |
| 9,402,884 | B2 | 8/2016 | Bums |
| 9,642,822 | B2 | 5/2017 | Wagner |
| 9,770,492 | B2 | 9/2017 | Genkin et al. |
| 9,845,461 | B2 | 12/2017 | Genkin et al. |
| 9,867,871 | B2 | 1/2018 | Jain |
| 10,617,743 | B2 | 4/2020 | Genkin et al. |
| 10,696,956 | B2 | 6/2020 | Fuchs et al. |
| 10,988,746 | B2 | 4/2021 | Fuchs et al. |
| 2004/0138156 | A1 | 7/2004 | Schneider et al. |
| 2009/0010966 | A1 | 1/2009 | Davis et al. |
| 2013/0149749 | A1 | 6/2013 | Holliger et al. |
| 2013/0236945 | A1 | 9/2013 | Song et al. |
| 2014/0199329 | A1 | 7/2014 | Wagner et al. |

(Continued)

FOREIGN PATENT DOCUMENTS

| | | |
|---|---|---|
| WO | 2011053982 A2 | 5/2011 |
| WO | 2011131772 A1 | 10/2011 |

(Continued)

OTHER PUBLICATIONS

Singh et al., Current Protein and Peptide Science 19(1):5-15, 2018.*

(Continued)

*Primary Examiner* — Delia M Ramirez

(74) *Attorney, Agent, or Firm* — Morgan, Lewis & Bockius LLP

(57) ABSTRACT

The present disclosure provides engineered human extracellular DNASE proteins (e.g., variants of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)) that are useful for treating conditions characterized by neutrophil extracellular trap (NET) accumulation and/or release. In accordance with the invention, the DNase variant has advantages for therapy and/or large-scale manufacturing.

24 Claims, 24 Drawing Sheets

Specification includes a Sequence Listing.

(56) References Cited

U.S. PATENT DOCUMENTS

| | | | |
|---|---|---|---|
| 2016/0251638 | A1 | 9/2016 | Posada et al. |
| 2016/0376366 | A1 | 12/2016 | Chang et al. |
| 2017/0196945 | A1 | 7/2017 | Wagner et al. |
| 2020/0024585 | A1 | 1/2020 | Fuchs et al. |
| 2021/0207114 | A1 | 7/2021 | Fuchs et al. |
| 2021/0277372 | A1 | 9/2021 | Fuchs et al. |
| 2022/0025343 | A1 | 1/2022 | Fuchs |

FOREIGN PATENT DOCUMENTS

| | | |
|---|---|---|
| WO | 2015066550 A1 | 5/2015 |
| WO | 2016139659 A1 | 9/2016 |
| WO | 2018015474 A1 | 1/2018 |
| WO | 2018064681 A1 | 4/2018 |
| WO | 2018134403 A1 | 7/2018 |
| WO | 2018134419 A1 | 7/2018 |
| WO | 2019036719 A2 | 2/2019 |

OTHER PUBLICATIONS

Al-Mayouf et al., Loss-of-function variant in DNASE1L3 causes a familial form of systemic lupus erythematosus, Nature Genetics, 2011, vol. 43, No. 12, pp. 1186-1188.

Andersen et al. 2014; Extending serum half-life of albumin by engineering neonatal FC receptor (FcRn) binding. Journal of Biological Chemistry. 289(19): 13492-13502.

Barnes et al. "Targeting potential drivers of COVID-19: Neutrophil extracellular traps", J. Exp. Med., 2020, vol. 217, pp. 1-7.

Baron et al., Cloning and characterization of an actin-resistant DNase I-like endonuclease secreted by macrophages, Gene, 1998, vol. 215 pp. 291-301.

Bassi et al. 2012; Regenerative therapies for diabetic microangiopathy. Experimental Diabetes Research. Article ID 916560, pp. 1-11.

Berntsson et al., "Structural insight into DNA binding and oligomerization of the multifunctional Cox protein of bacteriophage P2", Nucleic Acids Research, vol. 42, No. 4, 2014, pp. 2725-2735.

Boettcher et al. "Therapeutic targeting of extracellular DNA improves the outcome of intestinal ischemic reperfusion injury in neonatal rats," Scientific Reports, Nov. 13, 2017.

Branden et al., "Prediction, Engineering, and Design of Protein Structures", Introduction to Protein Structure, Garland Publishing Inc., New York, p. 247,1991.

Brill, et al., "Neutrophil extracellular traps promote deep vein thrombosis in mice", J Thromb Haemost. Jan. 2012 ; 10(1): 136--144.

Brinkmann, et all., "Neutrophil extracellular traps: Is immunity the second function of chromatin?", J. Cell Biol. vol. 198 No. 5 773-783.

Bruschi et al., Neutrophil extracellular traps (NET) induced by different stimuli: A comparative proteomic analysis, Plos One, 2019, pp. 1-18.

Carbonella et al., An autosomal recessive DNASE1L3-related autoimmune disease with unusual clinical presentation mimicking systemic lupus erythematosus, Lupus, 2017, vol. 26, pp. 768-772.

Chica et al., Semi-rational approaches to engineering enzyme activity: combining the benefits of directed evolution and rational design. CUM Opi. Biotechnol., 2005, vol. 16: 378-384.

CORDIS_project 628264 en, Degradation of Neutrophil Extracellular Traps and its impact on thrombolysis, https://cordis.europa.eu/project/id/628264, 2016, 3 pages.

De Meyer et al. "Extracellular Chromatin Is an Important Mediator of Ischemic Stroke in Mice," Arteriosclerosis, Thrombosis, and Vascular Biology, May 24, 2012 (May 24, 2012), vol. 32, No. 8, pp. 1884-1891. entire document.

Fuchs, et al., "Extracellular DNA traps promote thrombosis," PNAS, 2010, vol. 107, No. 36, pp. 15880-15885.

Fuchs, et al., "NET impact on deep vein thrombosis," Arterioscler Thromb Vasc Biol. Aug. 2012 ; 32(8): 1777-1783.

Hakkim et al., "Impairment of neutrophil extracellular trap degradation is associated with lupus nephritis", PNAS, vol. 107, No. 21, 2010, pp. 9813-9818.

Hattori et al. 2018; Nucleic-acid based gene therapy approaches for sepsis. European Journal of Pharmacology. 833: 403-410.

International Search Report and Written Opinion for International Application No. PCT/US2018/047084 , dated Feb. 15, 2019, 23 pages.

Jimenez-Alcazar, M, et al. Host DNases Prevent Vascular Occlusion by Neutrophil Extracellular Traps. Science. Dec. 1, 2017, vol. 358; pp. 1202-1206.

Keyel, "Dnases in health and disease", Developmental Biology, vol. 429, 2017, pp. 1-11.

Kobayashi et al., "Synchronous Growth of Pichia Pastoris for a High-Rate Production of DNaseI at Microquantities", Department of Chemical Engineering. Toyko Institute of Technology. On-Line No. 833, 2004 pp. 1-6.

Koyama, et al., "DNase y, DNase I, and caspase-activated DNase cooperate to degrade dead cells," Genes to Cells 21, 1150-1163 (2016).

Landhuis, "Spider-Man Immune Response May Promote Severe COVID-19", Sci. Am., 2020, pp. 1-7.

Napirei et al. 2009; Murine serum nucleases-contrasting effects of plasmin and heparin on the activities of DNaseI and DNaseI-lie 3 (DNase1l3). FEBS Journal. 276: 1059-1073.

Onuora, "DNASE1L3 prevents anti-DNA responses", Nature Rev. Rheumatol., 2016, vol. 12 No. 437,1 page.

Ozyakar et al., DNASE1L3 Mutations in Hypocomplementemic Urticarial Vasculitis Syndrome, Arthritis & Rheumatism, 2013, vol. 65, No. 8, pp. 2183-2189.

Parsiegla et al., The Structure of Human DNase I Bound to Magnesium and Phosphate Ions Points to a Catalytic Mechanism Common to Members of the DNase I-like Superfamily, Biochemistry, 2012, vol. 51, pp. 10250-10258.

Perini et al., "Topical application of Acheflan on rat skin injury accelerates wound healing: a histopathological, immunohistochemical and biochemical study", BMC Complementary and Alternative Medicine, 2015, vol. 15, No. 203, pp. 1-8.

Piccolo et al., "Intrapleural Tissue Plasminogen Activator and Deoxyribonuclease for Pleural Infection; An Effective and Safe Alternative to Surgery", AnnalsATS, vol. 11, No. 9, 2014 , pp. 1419-1425.

Reizis, "Project 3: The role of DNASE1L3 and its DNA substrate in lupus", National Institute of Health (NM), 2015,5 pages.

Rodriguez et al., Gen Bank accession No. 013609 Sep. 27, 2017.

Sadowski et al., "The sequence-structure relationship and protein function prediction", Current Opinion in Structural Biology 19:357-362, 2009.

Saito et al., Apoptotic DNA endonuclease (DNase-y ) gene transfer induces cell death accompanying DNA fragmentation in human glioma cells, Journal of Neuro-Oncology, 2003, vol. 63, pp. 25-31.

Seffernick, et al., "Melamine deaminase and Atrazine Chlorohydrolase: 98 Percent Identical but Functionally Different", Journal of Bacteriology, 2001, pp. 2405-2410.

Shiokawa et al. 2003; Identification of two functional nuclear localization signals in DNase gamma and their roles in its apoptotic DNase activity. Biochem. J. 376: 377-381.

Shiokawa et al., "Characterization of Human DNase I Family Endonucleases and Activation of DNase y during Apoptosis", Biochemistry 2001, 40, pp. 143-152.

Shiokawa et al. 1998; Molecular cloning and expression of a cDNA encoding an apoptotic endonuclease DNase gamma. Biochem. J. 332: 713-720.

Sisirak et al., "Digestion of Chromatin in Apoptotic Cell Microparticles Prevents Autoimmunity", Cell vol. 166, 2016 , pp. 88-101.

Tang et al., "Identification of Dehalobacter Reductive Dehalogenases that Catalyse Dechlorination of Chloroform, 1,1,1-trichloroethane and 1,1-dichloroethane", Phil Trans R Soc B, 368, 20120318, 1-10, 2013.

Val* et al., Fibrinolysis at the Interface of Thrombosis and Inflammation The Role of Neutrophil Extracellular Traps, Hungarian Scientific Research Fund, Department of Medical Biochemistry, Semmelweis University, Budapest, Hungary, 2014, p. 1-59.

(56)  References Cited

OTHER PUBLICATIONS

Wang et al., "Targeting the extracellular scavenger DNASE1L3 on SLE", J Xiangya Med, 2017, 3 pages.

Whisstock et al. Quaterly Reviews of Biophysics, 2003, "Prediction of protein function from protein sequence and structure", 36(3): 307-340.

Wilber et al., "Deoxyribonuclease I-like III Is an Inducible Macrophage Barrier to Liposomal Transfection", MolecularTherapy, vol. 6, No. 1, 2002, pp. 35-42.

Witkowski et al., "Conversion of a f3-Ketoacyl Synthase to a Malonyl Decarboxylase by Replacement of the Active-Site Cysteine with Glutamine", Biochemistry 1999, 38, pp. 11643-11650.

Benjamin Sally, "Failure to process chromatin on apoptotic microparticles in the absence of deoxyribonuclease 1 like 3 drives the development of systemic lupus erythematosus," Columbia University, (2017).

NCBI Reference Sequence: NP_004935.1, "deoxyribonuclease gamma isoform 1 precursor [*Homo sapiens*]."

* cited by examiner

FIG. 4

| Input cDNA | C-Terminal Amino Acid Sequence | Relative Amount |
|---|---|---|
| Wild-Type DNASE1L3 | K291_S305del | 54% |
| | K292_S305del | 17% |
| | S293_S305del | 29% |
| Basic Domain Deleted DNASE1L3 | F275Y F279_K280delinsVM Q282_S305delinsK | 100% |

FIG. 5

POLYANION
(e.g. Dextrane Sulfate (DS))

STEP 1 Formation of D1L3-DS complex

Scavenging of DNASE1L3 with polyanions

DNASE1-LIKE 3 or variant thereof

ANION EXCHANGE SURFACE
(e.g. resin)

STEP 2 Dissociation of D1L3-DS complex

CATION EXCHANGE SURFACE
(e.g. resin)

STEP 3 Affinity purification of DS-free D1L3

FIG. 7

Mutation of identified trypsin cleavage sites

| # | AA (P13) (SEQ ID NO: 4) | Amino Acid Substitution | P1 (SEQ ID NO:) Bulging Effect Mutation |
|---|---|---|---|
| 1 | R22 | R22A/V/S, R22H/Q/E | M21_R22delinsLK |
| 2 | R29 | R29A/V/S, R29H/Q/E | V28_S30delinsIQT |
| 3 | R51 | R51A/V/S, R51H/Q/E | N/A (conserved residue) |
| 4 | R66 | R66A/V/S, R66H/Q/E | N64_I70delinsHLTAVGK |
| 5 | R80 | R80A/V/S, R80H/Q/E | R77_I83delinsQDAPD |
| 6 | R81 | R81A/V/S, R81H/Q/E | R77_I83delinsQDAPD |
| 7 | R95 | R95A/V/S, R95H/Q/E | N/A (conserved residue) |
| 8 | K99 | R99A/V/S, R99H/Q/E | N/A (conserved residue) |
| 9 | R115 | R115A/V/S, R115H/Q/E | V113_R115delinsAVD |
| 10 | K147 | K147A/V/S, K147H/Q/E | K147_D148delinsRE |
| 11 | K163 | K163A/V/S, K163H/Q/E | K163A |
| 12 | K180 | K180A/V/S, K180H/Q/E | K180_A181delinsGL |
| 11 | R208 | R208A/V/S, R208H/Q/E | R208W |
| 12 | R212 | R212A/V/S, R212H/Q/E | R212T |
| 13 | R235 | K235A/V/S, K235H/Q/E | N/A (conserved residue) |
| 14 | R239 | K239A/V/S, K239H/Q/E | L238_R239delinsVA |
| 15 | K250 | K250A/V/S, K250H/Q/E | K250D |
| 16 | K262 | K262A/V/S, K262H/Q/E | K262G |

Selection of Amino Acid Substitution: Grantham's distance

Arg (R) / His (H): 29
Arg (R) / Glu (E): 54
Arg (R) / Gln (Q): 53

Lys (K) / His (E): 32
Lys (K) / Gln (H): 54
Lys (K): Glu (E): 56

Mutation of predicted plasmin cleavage sties

| # | AA in D1B (SEQ ID NO: 4) | Amino Acid Substitution | D1 (SEQ ID NO: 1) Binding Blk-1 Mutation |
|---|---|---|---|
| 1 | K180 | K180A, K180H/Q/E | K180_A181delinsGL |
| 2 | K200 | K200A, K200H/Q/E | P198_A201delinsRPSQ |
| 3 | K259 | K259A, K259H/Q/E | A259A |
| 4 | R285 | R285A, R285H/Q/E | N/A (absent in D1) |

Description of mutated plasmin cleavage sites in D1L3:

- Mutation 1: K180_A181delinsGL
- Mutation 2: P198_A201delinsRPSQ
- Mutation 3: K259A
- Mutation 4: R285A

FIG. 11

Mutation of identified plasmin cleavage sites

| # | AA (P1) (SEQ ID NO: A) | Amino Acid Substitution | DI (SEQ ID NO: 1) Binding Base Mutation |
|---|---|---|---|
| 1 | R22 | R22H/Q/E | M21_R22delinsLK |
| 2 | R29 | R29H/Q/E | V28_S30delinsIQT |
| 3 | K45 | K45H/Q/E | N/A (conserved residue) |
| 4 | K47 | K47H/Q/E | K47_K50delinsQILS |
| 5 | K74 | K74H/Q/E | M72_K74delinsLDN |
| 6 | R81 | R81H/Q/E | R77_I83delinsQDAPD |
| 7 | R92 | R92H/Q/E | S91_R92delinsEP |
| 8 | K107 | K107H/Q/E | K107_L110delinsRPDQ |
| 9 | K176 | K176H/Q/E | K176_R178delinsQEK |
| 10 | R212 | R212H/Q/E | R212T |
| 11 | K226 | R226H/Q/E | V225_S228delinsATP |
| 12 | K227 | K227H/Q/E | V225_S228delinsATP |
| 13 | K250 | K250H/Q/E | K250D |
| 14 | K259 | K259H/Q/E | K259A |
| 15 | K262 | K262H/Q/E | K262G |

Selection of Amino Acid Substitution:
Grantham's distance

Arg (R) / His (H): 29
Arg (R) / Glu (E): 54
Arg (R) / Gln (Q): 53

Lys (K) / His (E): 32
Lys (K) / Gln (H): 54
Lys (K): Glu (E): 56

FIG. 14

Mutation of identified plasmin cleavage sites

| # | AA in DIL3 (SEQ ID NO: 4) | Amino Acid Substitution | D1 (SEQ ID NO: 1) Building Block Mutation |
|---|---|---|---|
| 1 | C24 | C24A/S/G | C24_S25delinsAA |
| 2 | C52 | C52A/S/G | C52Y |
| 3 | C68 | C68A/S/G | N64_I70delinsHLTAVGK |
| 4 | C194 | C194A/S/G | N/A (conserved residue) |
| 5 | C231 | C231A/S/G | N/A (conserved residue) | cGMP-Expression System:
*Pichia pastoris*

Expression Vector:

*FIG. 18*

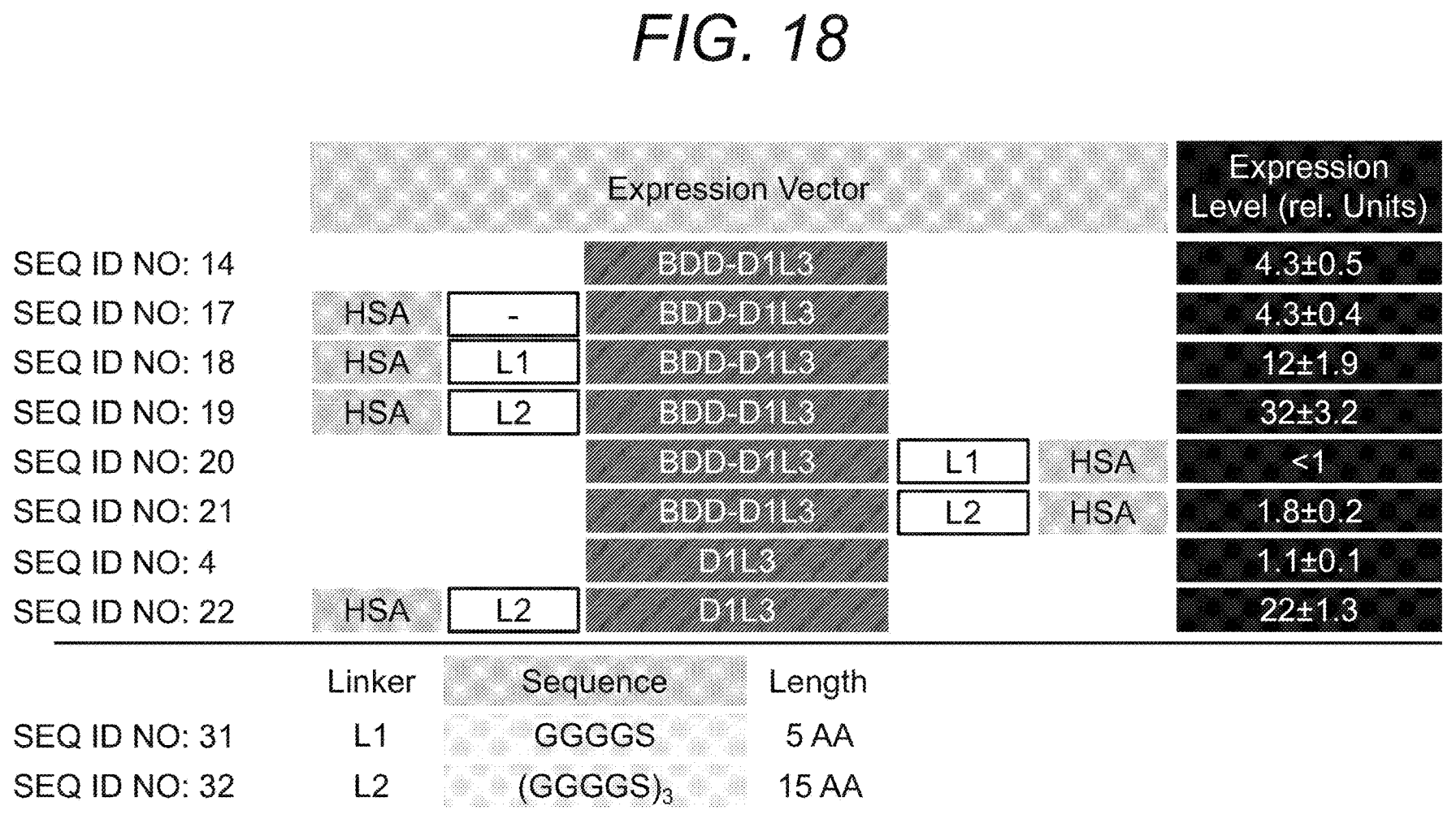

| SEQ ID NO | | Expression Vector | | | | Expression Level (rel. Units) |
|---|---|---|---|---|---|---|
| SEQ ID NO: 14 | HSA | - | BDD-D1L3 | | | 4.3±0.5 |
| SEQ ID NO: 17 | HSA | L1 | BDD-D1L3 | | | 4.3±0.4 |
| SEQ ID NO: 18 | HSA | L2 | BDD-D1L3 | | | 12±1.9 |
| SEQ ID NO: 19 | | | BDD-D1L3 | | | 32±3.2 |
| SEQ ID NO: 20 | | | BDD-D1L3 | L1 | HSA | <1 |
| SEQ ID NO: 21 | | | BDD-D1L3 | L2 | HSA | 1.8±0.2 |
| SEQ ID NO: 4 | | | D1L3 | | | 1.1±0.1 |
| SEQ ID NO: 22 | HSA | L2 | D1L3 | | | 22±1.3 |

| Linker | Sequence | Length |
|---|---|---|
| SEQ ID NO: 31 | L1 | GGGGS | 5 AA |
| SEQ ID NO: 32 | L2 | (GGGGS)₃ | 15 AA |

*FIG. 19*

| SEQ ID NO: | | Expression Vector | | | Expression Level (rel. Units) |
|---|---|---|---|---|---|
| SEQ ID NO: 22 | HSA | L2 | D1L3 | | 17±5.5 |
| SEQ ID NO: 23 | HSA | L3 | D1L3 | | 22±6.9 |
| SEQ ID NO: 24 | HSA | L4 | D1L3 | | 11±4.9 |

| | Linker | Sequence | Length | Property |
|---|---|---|---|---|
| SEQ ID NO: 32 | L2 | (GGGGS)$_3$ | 15 | flexible |
| SEQ ID NO: 33 | L3 | (AP)$_7$ | 14 | rigid |
| SEQ ID NO: 34 | L4 | A(EAAAK)$_2$A | 12 | rigid |

Expression Vector:

Factor XIIa Cleavable Linker:

ENGINEERED DNASE ENZYMES FOR THROMBOSIS THERAPY

RELATED APPLICATIONS

The present application claims the benefit of, and priority to, U.S. Provisional Application Nos.: 62/742,682 filed Oct. 8, 2018; 62/775,563 filed Dec. 5, 2018; 62/779,104 filed Dec. 13, 2018; U.S. Pat. No. 62,808,601 filed Feb. 21, 2019; and 62/846,904 filed May 13, 2019, the contents of which are hereby incorporated by reference in their entireties.

FIELD OF THE INVENTION

This invention relates to the field of engineered DNASE enzymes.

SEQUENCE LISTING

The instant application contains a Sequence Listing which has been submitted in XML format via EFS-Web and is hereby incorporated by reference in its entirety. Said XML copy, created on Oct. 30, 2023, is named NTR-004C3_119601-5004_Sequence_Listing.xml and is 71,534 bytes in size.

BACKGROUND

Inflammation is an essential host response to control invading microbes and heal damaged tissues. Uncontrolled and persistent inflammation causes tissue injury in a plethora of inflammatory disorders. Neutrophils are the predominant leukocytes in acute inflammation. During infections, neutrophils generate neutrophil extracellular traps (NETs), lattices of DNA-filaments decorated with toxic histones and enzymes that immobilize and neutralize bacteria. However, inappropriately released NETs may harm host cells due to their cytotoxic, proinflammatory, and prothrombotic activity.

DNASE1 (D1) forms along with DNASE1-LIKE 1 (D1L1), DNASE1-LIKE 2 (D1L2) and DNASE1-LIKE 3 (D1L3), the DNASE1-protein family, a group of homologous secreted DNase enzymes. DNASE2A and DNASE2B form an additional group of homologous extracellular DNase enzymes. DNASE1- and DNASE2-protein family members are evolutionary conserved and expressed in various species, including humans. Recombinant human DNASE1- and DNASE2-protein family members provide drug candidates for NET-associated diseases. While D1 has been developed for some therapeutic applications in patients, the conditions for large-scale manufacturing of the other members of the DNASE1-protein family have not been described. Furthermore, the physical, enzymatic, and pharmacokinetic properties of these enzymes are not ideal for clinical applications. Thus, there is a need for defining a manufacturing process for D1L1, D1L2, and D1L3 enzymes, and for engineering DNases for use in therapy, including for degrading NETs.

SUMMARY OF THE DISCLOSURE

The present invention provides engineered human extracellular DNASE proteins (e.g., variants of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)) that are useful for treating conditions characterized by extracellular DNA, extracellular chromatin, and neutrophil extracellular trap (NET) accumulation and/or release. In accordance with aspects of the invention, the DNase variants described herein are more suitable for therapy and/or more amenable to large-scale manufacturing. In some embodiments, the DNase variants described herein have benefits for medical therapy, including systemic therapy. Such benefits include slower drug elimination, e.g., increased circulatory half-life (e.g., serum half-life), an extended duration of pharmacodynamic activity, high chromatin-degrading activity, and protease resistance.

In some aspects, the invention provides a D1L3 variant, wherein the D1L3 variant has one or more of increased protein stability, slower drug elimination and increased duration of pharmacodynamic activity, resistance to proteolytic degradation, higher production levels with in vitro expression systems, better suitability for purification, and not substantially less, the same, or better chromatin and/or NET-degrading activity as compared to wild-type D1L3 Isoform 1 enzyme of SEQ ID NO:4 or wild-type D1L3 Isoform 2 enzyme of SEQ ID NO:5.

In some embodiments, the D1L3 variant is a fusion protein that comprises an amino acid sequence that is at least 80% identical to the mature enzyme defined by SEQ ID NO:4 or SEQ ID NO:5, an albumin amino acid sequence at the N-terminus of the mature enzyme, and optionally a linking amino acid sequence between the albumin amino acid sequence (the albumin domain) and the D1L3 amino acid sequence (the D1L3 domain). In these embodiments, the D1L3 exhibits slower elimination (e.g., improved circulatory half-life or serum half-life) and an extended duration of pharmacodynamic activity, including for systemic therapy. In some embodiments, the fusion of albumin with linking sequence to the D1L3 domain does not substantially impact chromatin-degrading activity of the enzyme (e.g., a measured using an in vitro assay) as compared to the enzyme without an albumin fusion.

In these embodiments, the D1L3 domain of the fusion protein has a deletion of all or part of the C-terminal basic domain that is present in the wild-type D1L3 enzyme. Deletion or inactivation of the C-terminal basic domain substantially improves chromatin degrading activity. That is, removal of the C-terminal basic domain (BD) activates the wild-type D1L3 enzyme for degrading chromatin.

In some embodiments, the D1L3 variant has one or more building block substitutions from D1. For example, the D1L3 variant may have the building block substitution of Q282_S305delinsK, which includes a deletion of the C-terminal basic domain, which domain is absent in D1. In some embodiments, the D1L3 variant has an amino acid substitution at the position corresponding to position 101 of SEQ ID NO:4. The substitution can be Arg based on the corresponding building block from D1, or in some embodiments is Lys. Substitutions at this position can enhance chromatin-degrading activity of a D1L3 variant.

The linker where present may be a flexible linker, a rigid linker, or a physiologically-cleavable linker, such as a protease-cleavable linker. For example, the linker may be a hydrophilic amino acid sequence, and may be predominately constructed from amino acids selected from Gly, Ala, Ser, Thr, and Pro. In some embodiments, the variant is a flexible linker that is predominately glycine and serine residues (e.g., $(G_yS)_n$ linkers, where y is from 1 to 5, and n is from 1 to 20). In some embodiments, the linker is an α-helical linker. In some embodiments, the linker has at least 15 amino acids, or at least 25 amino acids. In various embodiments, longer linkers of at least 15 amino acids can provide improvements in yield upon expression in mammalian and non-mammalian expression systems, such as CHO cells or *Pichia pastoris*. Further, and surprisingly, longer linker sequences showed improved chromatin-degrading activity in an in vitro chromatin-degrading assay, as compared to shorter linker sequences.

In various embodiments, the D1L3 variant comprises the amino acid sequence of any one of SEQ ID NOS: 17 to 30, in each case optionally having from one to twenty amino acid modifications independently selected from insertions, deletions, or substitutions. These sequences provide exemplary fusion proteins between D1L3 (or D1L3 variants) with albumin sequences, including with various linker designs. In some embodiments, the amino acid modifications are in the D1L3 domain, the albumin domain, or both domains. In some embodiments, the variant has the amino acid sequence of SEQ ID NO: 19, SEQ ID NO: 22, SEQ ID NO: 26, SEQ ID NO: 27, SEQ ID NO: 28, SEQ ID NO: 29, or SEQ ID NO: 30. In these embodiments, the D1L3 variant comprises, in order from N-terminus to C-terminus: an albumin amino acid sequence, an intermediate or long flexible linker, and a D1L3 amino acid sequence (i.e., including D1L3 variants). SEQ ID NO: 28 further comprises an albumin fusion at the C-terminus through a long flexible peptide linker.

In other embodiments, the linker is cleavable by a protease, such as a coagulation pathway protease, such as activated Factor XII. In certain embodiments, the linker contains amino acid sequence of Factor XI and/or prekallikrein. In other embodiments, the linker includes a peptide sequence that is targeted for cleavage by a neutrophil specific protease, such as neutrophil elastase, cathepsin G, or proteinase 3.

In some aspects, the invention provides variants of extracellular DNASE enzymes engineered to have advantages in manufacturing, providing for production of the recombinant enzyme suitable for use in therapy. In various embodiments, the invention provides a recombinant D1, D1L1, D1L2, and D1L3 variant comprising one or more amino acid substitutions in cysteine residues (or PEGylation of Cys residues) resulting in reduced intra- and inter-molecular cross-linking via disulfide bridges during protein expression.

In other aspects, the invention provides variants of extracellular DNASE enzymes engineered to have advantages in protease resistance, for improving in vivo exposure, e.g., slowing elimination, e.g. extending half-life (e.g., serum half-life), and extending duration of pharmacodynamic activity, as well as reducing proteolysis during recombinant enzyme production. This disclosure identifies, for example, D1L3 residues that are sensitive to proteolysis by plasmin, thrombin, and/or trypsin, as well as residues (e.g., paired basic amino acids) that are sensitive to proteases produced by mammalian and non-mammalian cell lines. Engineered mutation of these residues can confer these advantages in protease resistance.

In other aspects, the invention provides a method for recombinant production of extracellular DNASE proteins, including variants thereof described herein. In some embodiments, the method employs a non-mammalian expression system, e.g., a eukaryotic non-mammalian expression system, such as *Pichia pastoris*. In some embodiments, the *Pichia pastoris* encodes the DNase enzyme with its native signal peptide allowing for secretion from host cells. In some embodiments, the expression system is a mammalian cell expression system, such as Chinese Hamster Ovary (CHO) cells.

In some embodiments, the recombinant expression system has a deletion or inactivation of one or more proteases that cleave at paired basic amino acids. Exemplary enzymes include Furin (expressed by CHO cells) and Aspartic proteinase 3 (Ysp1) and Kexin (Kex2) expressed by *Pichia pastoris*. In some embodiments, these enzymes are not genetically deleted or inactivated, but their activity is inhibited with a protease inhibitor during recombinant protein production.

In some embodiments, the growth medium for the non-mammalian expression system or mammalian expression system is supplemented with polyanions such as dextran sulfate, heparins, ferric citrate, and EDTA. In further embodiments, the growth medium of *Pichia pastoris* or other expression system is supplemented with dextran sulfate that has an average molecular weight of between 5 kDa and 100 kDa. For example, the polyanion may be added to the culture in an amount sufficient to complex with the recombinant protein produced. In some embodiments, the recombinant extracellular DNASE proteins and variants thereof from the culture medium of non-mammalian expression system or mammalian expression system, are purified through a method that includes the dissociation of recombinant extracellular DNASE proteins and variants from polyanions such as dextran sulfate, heparins, and EDTA.

In other aspects, the invention provides isolated polynucleotides encoding the D1, D1L1, D1L2, or D1L3 variants, as well as vectors and host cells. Polynucleotides may be encoding mRNA or DNA. Host cells can be cells of a recombinant expression system, including bacterial or eukaryotic, whether non-mammalian such as *Pichia pastoris*, or mammalian such as CHO cells. In other embodiments, the host cell can be delivered for DNASE therapy. For example, the invention in some embodiments provides host cells, e.g., human cells, e.g., white blood cells, modified to secrete one or more of the extracellular DNASE proteins described herein, and intended for administration as a therapeutic agent.

The invention further provides pharmaceutical compositions comprising the extracellular DNASE protein or variant thereof as described herein, or optionally the polynucleotide or the vector as described, and a pharmaceutically acceptable carrier. The pharmaceutical composition may be formulated for any administration route.

In other aspects, the invention provides a method for treating a subject in need of extracellular DNA degradation, extracellular chromatin degradation, extracellular trap (ET) degradation and/or neutrophil extracellular trap (NET) degradation, by administering a therapeutically effective amount of the extracellular DNASE or variant thereof or composition described herein.

Other aspects and embodiments of the invention will be apparent from the following detailed description.

DESCRIPTION OF FIGURES

FIG. 4 shows C-terminal amino acid sequences of recombinantly expressed wild-type D1L3 in *Pichia pastoris* to identify frequent cleavage sites. Amino acid sequencing of purified wild-type D1L3 identified three C-terminal deletion mutants: K291_S305del, K292_S305del, and S293_S305del. The C-terminus of wild-type D1L3 was not detected. In parallel, the chromatin degrading activity in the different concentrations of purified protein was analyzed and compared to purified DNASE1 (D1) and the Basic Domain Deleted DNASE1L3 (BDD-D1L3) with a F275Y/F279_K280delinsVM/Q282_S305delinsK mutation. The figure shows DNA analyzed by agarose gel electrophoresis.

FIG. 5 shows that the addition of dextran sulfate to CHO medium improves protein yield. Stable pools of CHO cells expressing wild-type D1L3 were incubated in standard CHO medium or CHO medium supplemented with dextran sulfate. Supernatants were analyzed by Western Blot (WB) using an anti-DNASE1L3 antibody. The figure shows that D1L3 expresses poorly in CHO cells with low yield. Addition of dextran sulfate increases the yield, but does not prevent production fragmentation. \

FIG. 6A shows that polyanions, such as dextran sulfate (DS), form a complex with D1L3. The D1L3-DS-complex prevents the interaction and scavenging of D1L3 by negatively charged surfaces during the production process. FIG. 6B and FIG. 6C show the two-step purification process of D1L3 from DS-D1L3-complexes.

FIG. 7 lists trypsin cleavage site mutation strategies to limit D1L3 degradation.

FIG. 8 is an alignment of human D1 (SEQ ID NO: 1) and human D1L3 (SEQ ID NO: 4) amino acid sequences, with plasmin sensitive KR residues shown.

FIG. 9 illustrates plasmin cleavage site mutation strategies to limit D1L3 degradation.

FIG. 11 lists plasmin cleavage sites based on plasmin digestion and shows mutation strategies to limit D1L3 degradation.

FIG. 12A illustrates a simple expression vector for D1L3 expression using the native secretory signal peptide. Supernatants of stable pools were analyzed by Western Blot using an anti-DNASE1L3 antibody, and FIG. 12B shows the presence of high molecular weight aggregates under non-reducing conditions, which are resolved under reducing conditions.

FIG. 14 lists the cysteine residues in D1L3, and shows mutation strategies to limit high molecular weight aggregates during protein expression.

FIG. 16A shows that the N-terminus of D1L3 was led by the alpha-mating factor (aMF) pre-pro secretion leader from *Saccharomyces cerevisiae*. FIG. 16B shows that the secretory signal from αMF resulted in glycosylation and non-processing of the signal peptide.

FIG. 17A shows the fusion construct with αMF, human serum albumin (HSA), linker sequence, and D1L3. FIG. 17B shows that the fusion construct is not glycosylated in *P. pastoris* expression system, and FIG. 17C shows that the fusion construct retains chromatin-degrading activity.

FIG. 18 illustrates the expression levels human serum albumin (HSA) fusion constructs of Basic Domain Deleted-DNASE1L3 (BDD-D1L3) or wild-type DNASE1L3 (D1L3) in *Pichia pastoris*. The HSA is fused either to the N- or C-terminus of BDD-D1L3 or D1L3. Two linker sequences, L1 and L2, were placed between HSA and BDD-D1L3 or D1L3.

FIG. 19 illustrates the expression levels human serum albumin (HSA) fusion constructs of wild-type DNASE1L3 (D1L3) in *Pichia pastoris*. The HSA is fused to the N-terminus of D1L3. Three different linker sequences (L2, L3, L4) were placed between HSA and D1L3.

FIG. 21A shows that Dnase1$^{-/-}$ Dnase1l3$^{-/-}$ mice injected with SEQ ID NO: 14 and SEQ ID NO: 19 show similar chromatin degrading activity in serum. FIG. 21B shows that SEQ ID NO: 19 has a circulation half-life of 3.3 days in mice expressing the human FcRn receptor.

7

D1L3) produced in *Pichia pastoris*. The HSA is fused to the N-terminus and C-terminus of BDD-D1L3. Two different linker sequences (L7 and L8) were placed between HSA and BDD-D1L3.

Figures 23A, 23B:
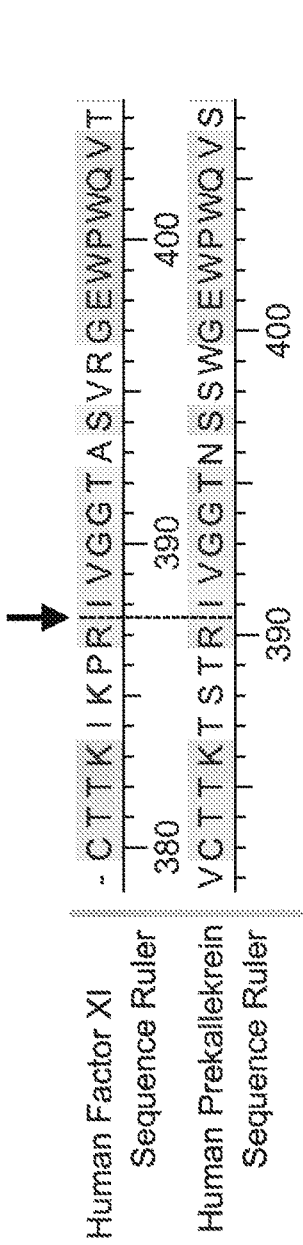

FIGS. 23A-B illustrate the design of cleavable linker sequences. FIG. 23A shows a fusion construct with HSA and a linker. FIG. 23B shows a linker cleavable by Factor XIIa. The sequences of a linker containing a human Factor XI sequence (SEQ ID NO: 42) and a linker containing a human prekallekrein (SEQ ID NO: 44) are shown.

Figure 24:
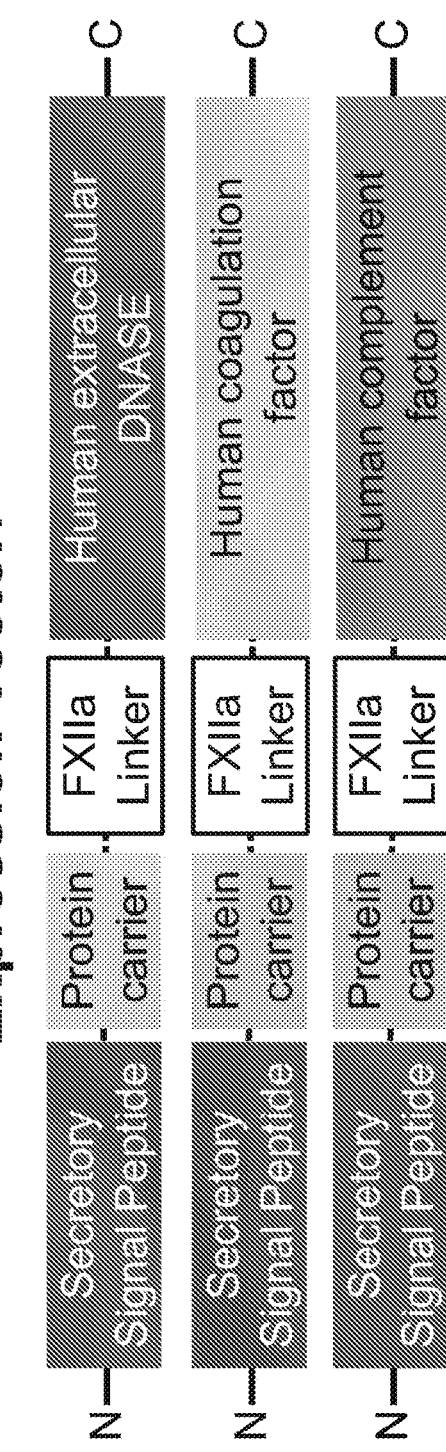

FIG. 24 illustrates other constructs that employ Factor XIIa cleavable linkers for half-life extended fusion proteins, including for human extracellular DNases, human coagulation factors, and human complement factors.

DESCRIPTION OF THE INVENTION

The present invention provides candidates of engineered human extracellular DNASE proteins (e.g., variants of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)) that are useful for treating conditions characterized by extracellular DNA, extracellular chromatin, and neutrophil extracellular trap (NET) accumulation and/or release. In accordance with aspects of the invention, the DNase variants described herein are more suitable and/or effective for therapy and/or are more amenable to large-scale manufacturing. In some embodiments, the DNase variants described herein have benefits for systemic therapy. Such benefits include longer exposure (e.g., slower elimination, longer circulatory half-life), extended duration of pharmacodynamic action, improved chromatin-degrading activity, and protease resistance.

Definitions

As used herein and in the claims, the singular forms "a," "an," and "the" include the singular and the plural reference unless the context clearly indicates otherwise. Thus, for example, a reference to "an agent" includes a single agent and a plurality of such agents.

The term "chromatinase" refers to a class of deoxyribonuclease enzyme that exhibits more than a negligible ability to cut, cleave or digest chromatin, i.e., DNA associated with one or more histone proteins. Human DNASE1L3 is a chromatinase. Generally, the various DNASE1L3 variants disclosed herein are chromatinases. Not all DNASE enzymes are chromatinases. For example, human DNASE1 has essentially no ability to cut, cleave, or digest chromatin and is not a chromatinase.

As used herein with reference to a drug, "half-life" refers to the elimination half-life of the concentration of the drug in an animal, as measured in a matrix of interest, e.g., serum or plasma. The skilled person will understand that not all drugs exhibit first-order kinetics or do so during all phases of elimination. In such cases, the skilled person will understand that the terms "half-life extension" or "extended half-life" are expressions that refer to a slower rate of elimination.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, "neutrophil extracellular trap" and the acronym "NET" refer to a network of extracellular fibers comprising nuclear contents, e.g., DNA bound to histone proteins that are released from an immune cell, typically a neutrophil, in a programmed fashion.

Unless otherwise specified, a "nucleotide sequence or nucleic acid encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "about" and "approximately" include an amount that is ±10% of an associated numerical value.

The term "extracellular DNASE" refers to extracellular DNASE proteins of the DNASE1- and DNASE2-family (e.g., DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2). DNASE2A (D2A), and DNASE2B (D2B)).

In some aspects and embodiments, the extracellular DNASE or variant thereof is fused, optionally by means of an interposed linker, to a half-life extending moiety, such as albumin, transferrin, an Fc, or elastin-like protein, or a variant thereof. See, e.g., U.S. Pat. No. 9,458,218, which is hereby incorporated by reference in its entirety. In some embodiments, the extracellular DNASE or variant thereof is dimerized by an immunoglobulin hinge region. For example, the engineered enzymes described herein may also include an Fc-fusion domain (e.g., a hinge and CH2 domains and CH3 domains of an immunoglobulin). In some embodiments, the DNASE (e.g., D1L3 variant) is fused to an albumin amino acid sequence or domain, e.g., human albumin or a fragment or variant thereof. See, for example, WO 2015/066550 and U.S. Pat. No. 9,221,896, which are hereby incorporated by reference in their entirety. Albumin can be joined to the DNASE, optionally with an interposed linker, at the N-terminus and/or the C-terminus of the engineered extracellular DNASE or variant thereof. An exemplary albumin amino acid sequence is provided by SEQ ID NO: 39. In some embodiments. D1L3 and D1, or variants as described herein, are together dimerized by an Fc hinge region, creating a dimeric molecule with synergistic functional properties for degrading NETs. In some embodiments, the extracellular DNASE or variant thereof is fused at the N-terminus to an albumin amino acid sequence, through a peptide linker. The peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length. In still other embodiments, the linker is an organic molecule, group, polymer (e.g., PEG), or chemical moiety that is covalently coupled to the extracellular DNASE and half-life extending moiety (e.g., albumin).

In some aspects, the invention provides a D1L3 variant, wherein the D1L3 variant has one or more of increased protein stability, increased pharmacokinetic exposure and duration of pharmacodynamic activity, resistance to proteolytic degradation, higher production levels with in vitro expression systems, better suitability for purification, and not substantially less, the same, or better chromatin and/or NET-degrading activity as compared to wild-type D1L3 Isoform 1 enzyme of SEQ ID NO:4 or wild-type D1L3 Isoform 2 enzyme of SEQ ID NO:5. As used herein, unless stated to the contrary, the term "D1L3" includes either Isoform 1 or Isoform 2.

The DNA- and/or chromatin- and/or NET-degrading activity of an enzyme, e.g. a D1L3 variant, can be measured in vitro, for example by incubation of the enzyme with DNA, chromatin, or NETs, obtained, e.g., from purified nuclei, DNA, or ex vivo blood or neutrophils induced to form NETs. Alternatively, the DNA- and/or chromatin- and/or NET-degrading activity of an enzyme, e.g. a D1L3 variant, can be measured in vivo, for example by administering the enzyme to a subject, wherein the subject produces or is induced to produce extracellular DNA, chromatin, or NETs, and measuring the effect of the enzyme on concentrations of DNA, chromatin, or NET levels in a matrix, e.g. serum, preferably with a parallel negative control, or by temporally comparing the concentrations before and after administration of the enzyme.

In some embodiments, the D1L3 variant has approximately the same chromatin- and/or NET-degrading activity as compared to wild-type D1L3 Isoform 1 enzyme of SEQ ID NO:4 or wild-type D1L3 Isoform 2 enzyme of SEQ ID NO:5. In some embodiments, D1L3 variant has higher chromatin- and/or NET-degrading activity as compared to wild-type D1L3 Isoform 1 enzyme of SEQ ID NO:4 or wild-type D1L3 Isoform 2 enzyme of SEQ ID NO:5.

In some embodiments, the D1L3 variant is a fusion protein comprising an albumin domain, an optional linker, and a D1L3 domain. In some embodiments, the albumin domain and optional linker are located on the N-terminal side of the D1L3 domain. In some embodiments, the albumin domain and optional linker are located on the C-terminal side of the D1L3 domain. In all such embodiments, the optional linker is interposed between the albumin domain and the D1L3 domain.

In some embodiments, the albumin amino acid sequence or domain of the fusion protein is at least about 75%, or at least about 80%, or at least about 85%, at least 90%, at least 95%, at least 97%, at least 98%, or at least 99% identical to the reference albumin sequence defined by SEQ ID NO: 39. In some embodiments, the albumin amino acid sequence or domain comprises or consists of the reference albumin sequence defined by SEQ ID NO:39. In various embodiments, the albumin amino acid sequence binds to the neonatal Fc receptor (FcRn), e.g., human FcRn. The albumin amino acid sequence may be a variant of wild-type HSA (e.g., as represented by SEQ ID NO: 39). In various embodiments, albumin variants may have from one to twenty, or from one to ten amino acid modifications independently selected from deletions, substitutions, and insertions with respect to SEQ ID NO: 39. In some embodiments, the albumin amino acid sequence is any mammalian albumin amino acid sequence.

In some embodiments, the albumin amino acid sequence or domain is a fragment of full-length albumin, as represented by SEQ ID NO: 39. The term "fragment," when used in the context of albumin, refers to any fragment of full-length albumin or a variant thereof (as described above) that extends the half-life of a DNASE enzyme to which it is fused or conjugated, relative to the corresponding non-fused DNASE. In some embodiments, a fragment of an albumin can refer to an amino acid sequence comprising a fusion of multiple domains of albumin (see, e.g., WO2011/124718), such as domains I and III, and domains II and III. Generally, a fragment of albumin has at least about 100 amino acids or at least about 200 or at least about 300 amino acids of the full-length sequence. In various embodiments, the albumin fragment maintains the ability to bind human FcRn.

In some embodiments, the D1L3-like domain of the fusion protein is at least about 85%, or at least about 90%, or at least about 95%, at least about 97%, or at least about 98%, or at least about 99% identical to the mature D1L3 enzyme reference sequence defined by SEQ ID NO:4 or SEQ ID NO:5. In some embodiments, the D1L3 domain comprises or consists of the reference sequence defined by SEQ ID NO:4 or SEQ ID NO:5. In some embodiments, the reference sequence does not include the C-terminal basic domain of SEQ ID NO: 4 or 5 defined by the C-terminal 23 amino acids.

In some embodiments, the fusion protein comprises an D1L3 domain, wherein the amino acid sequence of the D1L3 domain is at least about 80% identical to the mature enzyme defined by SEQ ID NO:4 or SEQ ID NO:5. The fusion protein can further comprise the albumin amino acid sequence or domain at the N-terminus of the mature enzyme, and a linking amino acid sequence between the albumin amino acid sequence and the amino acid sequence of the mature enzyme. In some embodiments, the D1L3 domain comprises an amino acid sequence that is at least about 90% identical to the mature enzyme reference sequence defined by SEQ ID NO:4 or SEQ ID NO:5. In some embodiments, the reference sequence does not include the C-terminal basic domain of SEQ ID NO: 4 or 5 defined by the C-terminal 23 amino acids. The fusion protein comprising the D1L3 domain exhibits improved circulatory half-life and duration of pharmacodynamic effect, including for systemic therapy. In addition, the fusion of albumin with linking sequence does not substantially impact (or in some embodiments does not have any negative impact on) chromatin-degrading activity as determined using an in vitro chromatin-degrading assay, as compared to the variant without an albumin fusion.

When referring to sequence identity with wild-type DNase enzymes, and unless stated otherwise, sequences refer to mature enzymes lacking the signal peptide. Further, unless stated otherwise, amino acid positions are numbered with respect to the full-translated DNase sequence, including signal peptide, for clarity. Accordingly, for example, reference to sequence identity to the enzyme of SEQ ID NO:4 (human D1L3. Isoform 1) refers to a percent identity with the mature enzyme having M21 at the N-terminus. Similarly, reference to sequence identity to the enzyme of SEQ ID NO:1 (human D1) refers to a percent identity with the mature enzyme having L23 at the N-terminus.

In some embodiments, the D1L3 has a deletion of all or part of the C-terminal basic domain. The C-terminal basic domain is defined as the C-terminal 23 amino acids of SEQ ID NO:4 or SEQ ID NO:5. Deletion or inactivation of the C-terminal basic domain of D1L3 substantially improves chromatin degrading activity. See FIGS. 1, 2, and 4. In some embodiments, the D1L3 variant has a deletion of C-terminal basic domain amino acids, such as at least 5 amino acids, or in some embodiments at least 10 amino acids, or in some embodiments at least 15 amino acids, or in some embodiments at least amino acids of the C-terminal basic domain. In some embodiments, the D1L3 variant has a deletion of the entire C-terminal basic domain defined by the C-terminal 23 amino acids of SEQ ID NO:4 or SEQ ID NO:5. Exemplary BD deletions include Q282_S305delinsK (see SEQ ID NO: 9), S305delinsK (see SEQ ID NO: 10), K292_S305del (see SEQ ID NO: 11), and S293_S305del (see SEQ ID NO: 12). In some embodiments, the C-terminus of the D1L3 domain (having a BD deletion) has from 1 to 10 or from 1 to 5 amino acids at the C-terminus that do not align with the C-terminal BD, and which do not negatively impact chromatin degrading activity in an in vitro assay.

In some embodiments, the D1L3 variant is an engineered fusion protein comprising: a DNASE1L3 domain of a sequence selected from SEQ ID NO:8 through SEQ ID NO:16: a linker of a sequence selected from SEQ ID NO:31 through SEQ ID NO:38; and an albumin domain having the sequence of SEQ ID NO:39 or a variants or fragment as described. In some embodiments, the D1L3 variant has one or more building block substitutions from D1, which are described in PCT/US2018/04708, which is hereby incorporated by reference.

In some embodiments, the D1L3 sequence or domain contains a building block substitution from D1, which can be selected from one or more of: M21_R22delinsLK, C24 S25delinsAA, V28_S30delinsIQT, S34T, Q36_V44delinsMSNATLVSY, K47_K50delinsQILS, C52Y, I55_M58delinsIALVQE, I60_K61 delinsVR, N64_I70delinsHLTAVGK, M72_K74delinsLDN, R77_I83 delinsQDAPD, N86H, I89V, S91_R92delinsEP, T97S, Q101R, A103L, L105V, K107_L110delinsRPDQ, V113_R115delinsAVD, H118Y, H120D, Y122_A127delinsGCEPCGN, V129T, S131N, F135_V136delinsAI, W138R, Q140_H143delinFSRF, A145_D148delinsEVRE, V150A, I152V, T156 T157delinsAA, E159 S161delinsGDA, K163A, E167A, V169_E170delins YD, T173L, K176_R178delinsQEK, K180_A181 delinsGL, N183_F186delinsDVML, P198_A201 delinsRPSQ, K203_N204delinsSS, R208W, D210S, R212T, V214Q, G218P, Q220_E221delinsSA, V225_S228delinsATP, N230H, L238_R239delinsVA, Q241 S246delinsMLLRGA, K250D, N252_V254delinsALP, D256N, K259A, K262G, T264_E267delinsSDQL, L269_V271delinsQAI, F275Y, F279_K280delinsVM, Q282_S205delinsK, wherein each of the foregoing substitutions is numbered with respect to SEQ ID NO: 4.

For example, the D1L3 variant may have the building block substitution from D1 of Q282_S305delinsK, which includes a deletion of the C terminal basic domain, which is absent in D1. In some embodiments, the D1L3 enzyme has an amino acid substitution at the position corresponding to position 101 of SEQ ID NO:4. The substitution can be Arg based on the corresponding building block from D1, or in some embodiments is Lys. Substitutions at this position can enhance chromatin-degrading activity of D1L3. Other substitutions at this position will likely show similar properties.

Linkers where present can be selected from flexible, rigid, and cleavable peptide linkers. Flexible linkers are predominately or entirely composed of small, non-polar or polar residues such as Gly, Ser and Thr. An exemplary flexible linker comprises $(Gly_ySer)_n$ linkers, where y is from 1 to 10 (e.g., from 1 to 5), and n is from 1 to about 10, and in some embodiments, is from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is $A(EAAAK)_nA$, where n is as defined above (e.g., from 1 to 10, or 2 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 31 to 38.

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise $S(GGS)_4GSS$ (SEQ ID NO: 36). $S(GGS)_9GS$ (SEQ ID NO: 37), $(GGS)_9GS$ (SEQ ID NO: 39). In some embodiments, the linker has at least 10 amino acids, or at least 15 amino acids, or at least 20 amino acids, or at least 25 amino acids. For example, the linker may have a length of from 15 to 30 amino acids. In various embodiments, longer linkers of at least 15 amino acids can provide improvements in yield upon expression in *Pichia pastoris*. See FIG. 20. Further, and surprisingly, longer linker sequences showed improved chromatin-degrading activity, as compared to shorter linker sequences. See FIG. 20.

In various embodiments, D1L3 variant is a fusion protein comprising the amino acid sequence of any one of SEQ ID NOS: 17 to 30. In other embodiments, the D1L3 variant is a fusion protein comprising the amino acid sequence of any one of SEQ ID NOS: 17 to 30 and having from one to twenty or from one to ten, or from one to five amino acid modifications independently selected from amino acid insertions, deletions, or substitutions with respect to the reference sequence selected from SEQ ID NOS: 17 to 30. In some embodiments, the amino acid modifications are in the D1L3 domain, the albumin domain, or in both domains of the fusion protein. In some embodiments, the variant has the amino acid sequence of SEQ ID NO: 19, SEQ ID NO: 22, SEQ ID NO: 26, SEQ ID NO: 27, SEQ ID NO: 28, SEQ ID NO: 29, or SEQ ID NO: 30. In these embodiments, the albumin amino acid sequence is fused at the N-terminus or N-terminal side of D1L3 (or variant) through an intermediate or long flexible linker.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 42) and/or prekallikrein (SEQ ID NO: 44 or 45) or a physiologically cleavable fragment thereof. In selected embodiments, the linker amino acid sequence from Factor XI contains all or parts of SEQ ID NO: 42 (e.g., parts of SEQ ID NO:42, including modifications of SEQ ID NO:42 that allow for cleavage by Factor XIIa). In some embodiments, the linker amino acid sequence from prekallikrein contains all or parts of SEQ ID NO: 44 (e.g., parts of SEQ ID NO: 44, including modifications of SEQ ID NO: 44 that allow for cleavage by Factor XIIa). In other embodiments, the linker includes a peptide sequence that is targeted for cleavage by a neutrophil specific protease, such as neutrophil elastase, cathepsin G, and proteinase 3.

Some exemplary embodiments of D1L3 fusion proteins comprise a combination of three amino acid sequences that can be independently selected from sequences disclosed herein, and such sequences arranged in order from N-terminus to C-terminus;

Fusion 1: SEQ ID NO:4, SEQ ID NO:31, SEQ ID NO:39;

Fusion 2: SEQ ID NO:5, SEQ ID NO:31, SEQ ID NO:39;

Fusion 3: SEQ ID NO:8, SEQ ID NO:31, SEQ ID NO:39;

Fusion 4: SEQ ID NO:9, SEQ ID NO:31, SEQ ID NO:39;

Fusion 5: SEQ ID NO: 10, SEQ ID NO:31, SEQ ID NO:39;

Fusion 6: SEQ ID NO: 11, SEQ ID NO:31, SEQ ID NO:39;

Fusion 7: SEQ ID NO: 12 SEQ ID NO:31, SEQ ID NO:39;

Fusion 8: SEQ ID NO: 13, SEQ ID NO:31, SEQ ID NO: 39;

Fusion 9: SEQ ID NO: 14, SEQ ID NO:31, SEQ ID NO:39;

Fusion 10: SEQ ID NO: 15, SEQ ID NO:31, SEQ ID NO:39;

Fusion 11: SEQ ID NO: 16, SEQ ID NO:31, SEQ ID NO:39;

Fusion 12: SEQ ID NO:4, SEQ ID NO:32, SEQ ID NO:39;

Fusion 13: SEQ ID NO:5, SEQ ID NO:32, SEQ ID NO:39;

Fusion 14: SEQ ID NO:8, SEQ ID NO:32, SEQ ID NO:39;

Fusion 15: SEQ ID NO:9, SEQ ID NO: 32, SEQ ID NO:39;

Fusion 16: SEQ ID NO: 10, SEQ ID NO:32, SEQ ID NO:39;

Fusion 17: SEQ ID NO: 11, SEQ ID NO:32, SEQ ID NO:39;

Fusion 18: SEQ ID NO: 12 SEQ ID NO:32, SEQ ID NO:39;

Fusion 19: SEQ ID NO: 13, SEQ ID NO:32, SEQ ID NO:39;

Fusion 20: SEQ ID NO: 14, SEQ ID NO:32, SEQ ID NO:39;

Fusion 21: SEQ ID NO: 15, SEQ ID NO:32, SEQ ID NO:39;

Fusion 22: SEQ ID NO: 16, SEQ ID NO:32, SEQ ID NO:39;

Fusion 23: SEQ ID NO:4, SEQ ID NO:33, SEQ ID NO:39;

Fusion 24: SEQ ID NO:5, SEQ ID NO:33, SEQ ID NO:39;

Fusion 25: SEQ ID NO:8, SEQ ID NO:33, SEQ ID NO:39;

Fusion 26: SEQ ID NO:9, SEQ ID NO:33, SEQ ID NO:39;

Fusion 27: SEQ ID NO: 10, SEQ ID NO:33, SEQ ID NO:39;

Fusion 28: SEQ ID NO: 11, SEQ ID NO:33, SEQ ID NO:39;

Fusion 29: SEQ ID NO: 12 SEQ ID NO:33, SEQ ID NO:39;

Fusion 30: SEQ ID NO: 13, SEQ ID NO:33, SEQ ID NO:39;

Fusion 31: SEQ ID NO: 14, SEQ ID NO:33, SEQ ID NO:39;

Fusion 32: SEQ ID NO: 15, SEQ ID NO:33, SEQ ID NO:39;

Fusion 33: SEQ ID NO: 16, SEQ ID NO:33, SEQ ID NO:39;

Fusion 34: SEQ ID NO:4, SEQ ID NO:34, SEQ ID NO:39;

Fusion 35: SEQ ID NO:5, SEQ ID NO:34, SEQ ID NO:39;

Fusion 36: SEQ ID NO:8, SEQ ID NO:34, SEQ ID NO:39;

Fusion 37: SEQ ID NO:9, SEQ ID NO:34, SEQ ID NO:39;

Fusion 38: SEQ ID NO: 10, SEQ ID NO:34, SEQ ID NO:39;

Fusion 39: SEQ ID NO: 11, SEQ ID NO:34, SEQ ID NO:39;

Fusion 40: SEQ ID NO: 12 SEQ ID NO:34, SEQ ID NO:39;

Fusion 41: SEQ ID NO: 13, SEQ ID NO:34, SEQ ID NO:39;

Fusion 42: SEQ ID NO: 14, SEQ ID NO:34, SEQ ID NO:39;

Fusion 43: SEQ ID NO: 15, SEQ ID NO:34, SEQ ID NO:39;

Fusion 44: SEQ ID NO: 16, SEQ ID NO:34, SEQ ID NO:39;

Fusion 45: SEQ ID NO:4, SEQ ID NO:35, SEQ ID NO:39;

Fusion 46: SEQ ID NO:5, SEQ ID NO:35, SEQ ID NO:39;

Fusion 47: SEQ ID NO:8, SEQ ID NO:35, SEQ ID NO:39;

Fusion 48: SEQ ID NO:9, SEQ ID NO:35, SEQ ID NO:39;

Fusion 49: SEQ ID NO: 10, SEQ ID NO:35, SEQ ID NO:39;

Fusion 50: SEQ ID NO: 11, SEQ ID NO:35, SEQ ID NO:39;

Fusion 51: SEQ ID NO: 12 SEQ ID NO:35, SEQ ID NO:39;

Fusion 52: SEQ ID NO: 13, SEQ ID NO:35, SEQ ID NO:39;

Fusion 53: SEQ ID NO: 14, SEQ ID NO:35, SEQ ID NO:39;

Fusion 54: SEQ ID NO: 15, SEQ ID NO:35, SEQ ID NO:39;

Fusion 55: SEQ ID NO: 16, SEQ ID NO:35, SEQ ID NO:39;

Fusion 56: SEQ ID NO:4, SEQ ID NO:36, SEQ ID NO:39;

Fusion 57: SEQ ID NO:5, SEQ ID NO:36, SEQ ID NO:39;

Fusion 58: SEQ ID NO:8, SEQ ID NO:36, SEQ ID NO:39;

Fusion 59: SEQ ID NO:9, SEQ ID NO:36, SEQ ID NO:39;

Fusion 60: SEQ ID NO: 10, SEQ ID NO:36, SEQ ID NO:39;

Fusion 61: SEQ ID NO: 11, SEQ ID NO:36, SEQ ID NO:39;

Fusion 62: SEQ ID NO: 12 SEQ ID NO:36, SEQ ID NO:39;

Fusion 63: SEQ ID NO: 13, SEQ ID NO:36, SEQ ID NO:39;

Fusion 64: SEQ ID NO: 14, SEQ ID NO:36, SEQ ID NO:39;

Fusion 65: SEQ ID NO: 15, SEQ ID NO:36, SEQ ID NO:39;

Fusion 66: SEQ ID NO: 16, SEQ ID NO:36, SEQ ID NO:39;

Fusion 67: SEQ ID NO:4, SEQ ID NO:37, SEQ ID NO:39;

Fusion 68: SEQ ID NO:5, SEQ ID NO:37, SEQ ID NO:39;

Fusion 69: SEQ ID NO:8, SEQ ID NO:37, SEQ ID NO:39;

Fusion 70: SEQ ID NO:9, SEQ ID NO:37, SEQ ID NO:39;

Fusion 71: SEQ ID NO: 10, SEQ ID NO:37, SEQ ID NO:39;

Fusion 72: SEQ ID NO: 11, SEQ ID NO:37, SEQ ID NO:39;

Fusion 73: SEQ ID NO: 12 SEQ ID NO:37, SEQ ID NO:39;

Fusion 74: SEQ ID NO: 13, SEQ ID NO:37, SEQ ID NO:39;

Fusion 75: SEQ ID NO: 14, SEQ ID NO:37, SEQ ID NO:39;

Fusion 76: SEQ ID NO: 15, SEQ ID NO:37, SEQ ID NO:39;

Fusion 77: SEQ ID NO: 16, SEQ ID NO:37, SEQ ID NO:39;

Fusion 78: SEQ ID NO:4, SEQ ID NO:38, SEQ ID NO:39;

Fusion 79: SEQ ID NO:5, SEQ ID NO:38, SEQ ID NO:39;

Fusion 80: SEQ ID NO:8, SEQ ID NO:38, SEQ ID NO:39;

Fusion 81: SEQ ID NO:9, SEQ ID NO:38, SEQ ID NO:39;

Fusion 82: SEQ ID NO: 10, SEQ ID NO:38, SEQ ID NO:39;

Fusion 83: SEQ ID NO: 11, SEQ ID NO:38, SEQ ID NO:39;

Fusion 84: SEQ ID NO: 12 SEQ ID NO:38, SEQ ID NO:39;

Fusion 85: SEQ ID NO: 13, SEQ ID NO:38, SEQ ID NO:39;

Fusion 86: SEQ ID NO: 14, SEQ ID NO:38, SEQ ID NO:39;

Fusion 87: SEQ ID NO: 15, SEQ ID NO:38, SEQ ID NO:39;

Fusion 88: SEQ ID NO: 16, SEQ ID NO:38, SEQ ID NO:39;

Fusion 89: SEQ ID NO:4, SEQ ID NO:42, SEQ ID NO:39;

Fusion 90: SEQ ID NO:5, SEQ ID NO:42, SEQ ID NO:39;

Fusion 91: SEQ ID NO:8, SEQ ID NO:42, SEQ ID NO:39;

Fusion 92: SEQ ID NO:9, SEQ ID NO:42, SEQ ID NO:39;

Fusion 93: SEQ ID NO: 10, SEQ ID NO:42, SEQ ID NO:39;

Fusion 94: SEQ ID NO: 11, SEQ ID NO:42, SEQ ID NO:39;

Fusion 95: SEQ ID NO: 12 SEQ ID NO:42, SEQ ID NO:39;

Fusion 96: SEQ ID NO: 13, SEQ ID NO:42, SEQ ID NO:39;

Fusion 97: SEQ ID NO: 14, SEQ ID NO:42, SEQ ID NO:39;

Fusion 98: SEQ ID NO: 15, SEQ ID NO:42, SEQ ID NO:39;

Fusion 99: SEQ ID NO: 16, SEQ ID NO:42, SEQ ID NO:39

Fusion 100: SEQ ID NO:4, SEQ ID NO:43, SEQ ID NO:39;

Fusion 101: SEQ ID NO:5, SEQ ID NO:43, SEQ ID NO:39;

Fusion 102: SEQ ID NO:8, SEQ ID NO:43, SEQ ID NO:39;

Fusion 103: SEQ ID NO:9, SEQ ID NO:43, SEQ ID NO:39;

Fusion 104: SEQ ID NO: 10, SEQ ID NO:43, SEQ ID NO:39;

Fusion 105: SEQ ID NO: 11, SEQ ID NO:43, SEQ ID NO:39;

Fusion 106: SEQ ID NO: 12 SEQ ID NO:43, SEQ ID NO:39;

Fusion 107: SEQ ID NO: 13, SEQ ID NO:43, SEQ ID NO:39;

Fusion 108: SEQ ID NO: 14, SEQ ID NO:43, SEQ ID NO:39;

Fusion 109: SEQ ID NO:15, SEQ ID NO:43, SEQ ID NO:39;

Fusion 110: SEQ ID NO: 16, SEQ ID NO:43, SEQ ID NO:39;

Fusion 111: SEQ ID NO:4, SEQ ID NO:44, SEQ ID NO:39;

Fusion 112: SEQ ID NO:5, SEQ ID NO:44, SEQ ID NO:39;

Fusion 113: SEQ ID NO:8, SEQ ID NO:44, SEQ ID NO:39;

Fusion 114: SEQ ID NO:9, SEQ ID NO:44, SEQ ID NO:39;

Fusion 115: SEQ ID NO: 10, SEQ ID NO:44, SEQ ID NO:39;

Fusion 116: SEQ ID NO: 11, SEQ ID NO:44, SEQ ID NO:39;

Fusion 117: SEQ ID NO: 12 SEQ ID NO:44, SEQ ID NO:39;

Fusion 118: SEQ ID NO: 13, SEQ ID NO:44, SEQ ID NO:39;

Fusion 119: SEQ ID NO: 14, SEQ ID NO:44, SEQ ID NO:39;

Fusion 120: SEQ ID NO: 15, SEQ ID NO:44, SEQ ID NO:39;

Fusion 121: SEQ ID NO: 16, SEQ ID NO:44, SEQ ID NO:39;

Fusion 122: SEQ ID NO:4, SEQ ID NO:45, SEQ ID NO:39;

Fusion 123: SEQ ID NO:5, SEQ ID NO:45, SEQ ID NO:39;

Fusion 124: SEQ ID NO: 8, SEQ ID NO:45, SEQ ID NO:39;

Fusion 125: SEQ ID NO:9, SEQ ID NO:45, SEQ ID NO:39;

Fusion 126: SEQ ID NO: 10, SEQ ID NO:45, SEQ ID NO:39;

Fusion 127: SEQ ID NO: 11, SEQ ID NO:45, SEQ ID NO:39;

Fusion 128: SEQ ID NO: 12 SEQ ID NO:45, SEQ ID NO:39;

Fusion 129: SEQ ID NO: 13, SEQ ID NO:45, SEQ ID NO:39;

Fusion 130: SEQ ID NO: 14, SEQ ID NO:45, SEQ ID NO:39;

Fusion 131: SEQ ID NO: 15, SEQ ID NO:45, SEQ ID NO:39;

Fusion 132: SEQ ID NO: 16, SEQ ID NO:45, SEQ ID NO:39;

In some embodiments, the fusion protein is synthesized with a signal peptide. The signal peptide may be removed during secretion from the host cell. Exemplary signal peptides are shown SEQ ID NOS: 4 to 16 and SEQ ID NOS: 44 to 46. In some embodiments, the fusion protein is the mature protein, that is, lacking a signal peptide.

In various embodiments, the fusion protein is selected from fusion proteins 1 to 132, and the selected fusion protein may optionally have up to 20 (or up to 10) amino acid modifications independently selected from amino acid deletions, insertions, and substitutions.

In some aspects, the invention provides variants of extracellular DNASE enzymes engineered to have advantages in manufacturing, providing for production of the recombinant enzyme suitable for use in therapy, and which can optionally be used in connection with fusion protein embodiments (including albumin fusion embodiments) as already described. In various embodiments, the invention provides a recombinant D1, D1L1, D1L2, and D1L3 variant comprising one or more amino acid substitutions or deletions of cysteine residues resulting in reduced intra- and inter-molecular cross-linking via disulfide bridges during protein expression. For example, the DNase variant may lack one, two, or three cysteine residues present in the wild-type sequence (e.g., one, two, or three cysteine residues are deleted), or has one or more of such cysteine(s) substituted with other amino acid(s). In some embodiments, the one or more cysteine residues are substituted with an amino acid independently selected from Ala, Gly, and Ser, or one or more of the cysteine residues are substituted as part of a building block substitution. In some embodiments, the one or more cysteine residues that are substituted is/are not conserved between other members of the D1 protein family (e.g., D1, D1L1, D1L2, and D1L3). In some embodiments, the engineered enzyme comprises or further comprises at least one building block substitution from another member of the D1 protein family and/or other point mutation that results in increased protein stability, increased resistance towards degradation by proteases, increased bioavailability, and substantially the same or better DNA and/or chromatin and/or NET-degrading activity (in vitro or in vivo) as compared to the wild-type enzyme. In some embodiments, the substitutions and/or modifications include, among other modifications, only a single modification in cysteine residues. In some embodiments, removal of a single cysteine residue is sufficient for significant advantages in manufacturing.

In other aspects, the invention provides variants of extracellular DNASE enzymes engineered to have advantages in protease resistance, for improving in vivo half-life as well as reducing proteolysis during recombinant enzyme production. This disclosure identifies, for example, D1L3 residues that are sensitive to proteolysis by plasmin, thrombin, and/or trypsin, as well as residues (e.g., paired basic amino acids) that are sensitive to proteases produced by mammalian and non-mammalian cell lines.

The recombinant extracellular DNASE variants described herein may have a combination of point mutations including substitutions in cysteine residues, substitutions in protease-sensitive residues, and/or may comprise one or more block substitutions. Building Block Protein Engineering (BBPE) is described in PCT/US18/47084 and U.S. 62/800,790, the disclosures of which are hereby incorporated by reference. BBPE involves providing a protein-protein alignment of donor and recipient extracellular DNASE enzyme and identifying variable amino acid sequences for transfer ("building block"). The variable amino acid(s) are flanked by one or more conserved amino acids in the donor and recipient extracellular DNASE enzymes (upstream and downstream of the building block). These building blocks can be swapped between recipient and donor proteins, to produce a chimeric enzyme.

In other aspects, the invention provides a method for recombinant production of extracellular DNASE proteins, including variants thereof described herein. In some embodiments, the method employs a non-mammalian expression system, such as *Pichia pastoris*. In some embodiments, the *Pichia pastoris* encodes the DNase enzyme with the native signal peptide allowing for secretion from host cells. In some embodiments, the expression system is a mammalian cell expression system, such as Chinese Hamster Ovary (CHO) cells. In some embodiments, by removing cysteine residues that are unnecessary for activity, the invention avoids inter-molecular and intra-molecular disulfide bonds that otherwise form and hinder recombinant production. In some embodiments, substantial reductions in erroneous inter-molecular and intra-molecular disulfide bonds can be achieved with the substitution of a single cysteine residue.

In some embodiments, the recombinant expression system has a deletion or inactivation of one or more proteases that cleave at paired basic amino acids. Exemplary enzymes include Furin (expressed by CHO cells) and Aspartic proteinase 3 (Ysp1) and Kexin (Kex2) expressed by *Pichia pastoris*. In some embodiments, these enzymes are not genetically deleted or inactivated, but their activity is inhibited with a protease inhibitor during recombinant protein production.

In some embodiments, the growth medium for the non-mammalian expression system or mammalian expression system is supplemented with polyanions such as dextran sulfate, heparins, ferric citrate, and EDTA. In further embodiments, the growth medium of *Pichia pastoris* or other expression system is supplemented with dextran sulfate that has an average molecular weight of between 5 kDa and 100 kDa. In some embodiments, the dextran sulfate has an average molecular weight that is about 10 kDa or less, or about 20 kDa or less, or about 30 kDa or less, or about 40 kDa or less, or about 50 kDa or less, or about 75 kDa or less, or about 100 kDa or less. In various embodiments, the polyanion is added to the culture in an amount sufficient to complex with the recombinant protein produced.

In some embodiments, the recombinant extracellular DNASE proteins and variants thereof from the culture medium of non-mammalian expression system or mammalian expression system, are purified through a method that includes the dissociation of recombinant extracellular DNASE proteins and variants from polyanions such as dextran sulfate, heparins, EDTA. In certain embodiments, the purification method includes strong anion exchange resins such as triethylaminoethyl. In some embodiments, the extracellular DNASE protein produced according to the method is D1L3 or a variant thereof.

Accordingly, in some embodiments the invention provides a D1L3 variant comprising an amino acid sequence that is at least 80% identical to the enzyme defined by SEQ ID NO: 4 (human D1L3, Isoform 1) or SEQ ID NO: 5 (human D1L3, Isoform 2), and having one or more substitutions of cysteine residues and/or one or more substitutions of amino acids that are sensitive to proteolysis, e.g., in vivo proteolysis. In some embodiments, the D1L3 protein variant comprises one or more additional modifications that result in increased protein stability (e.g., protease resistance), higher production levels with in vitro expression systems, and/or not substantially less, the same, or better DNA and/or chromatin and/or NET-degrading activity as compared to wild-type D1L3 protein of SEQ ID NO:4 or SEQ ID NO: 5. For example, the D1L3 variant may comprise at least one additional building block substitution or point mutation disclosed in PCT/US2018/47084 (which is hereby incorporated by reference in its entirety), or may include one or more substitutions described herein for increasing protease resistance.

In some embodiments, the D1L3 variant has a substitution of Cys 68, which is optionally substituted with an amino acid selected from Ala. Ser, and Gly. In some embodiments, the variant comprises the substitution N64_I70 delinsHL-TAVGK. In some embodiments, the sequence HLTAVGK can be further modified by one, two, or three substitutions, deletions, and/or insertions (collectively), with the proviso that a Cys residue is not included. In some embodiments, the D1L3 variant comprises an amino acid sequence that has at least about 85%, at least about 90%, at least about 95%, or at least about 98% identity to the reference SEQ ID NO:4 or SEQ ID NO: 5.

In some embodiments, the invention provides a D1L3 enzyme having a polyethylene glycol (PEG) moiety conjugated at the position corresponding to Cys 68, which is believed to be an unpaired cysteine. In some embodiments, the D1L3 variant has a PEG conjugation to the amino acid corresponding to C194. In these embodiments, the PEG moiety will provide a half-life extension property, while avoiding disulfide scrambling and/or protein misfolding. In some embodiments, the PEG moiety is conjugated through maleimide chemistry, which can be conducted under mild conditions. Other conjugation chemistries are known and may be used, such as vinyl sulfone, dithyopyridine, and iodoacetamide activation chemistries. The PEG moiety can be linear or branched, and can be generally in the range of 10 kDa to 40 kDa, or in the range of 20 to 30 kDa.

Alternatively, or in addition, the invention provides a D1L3 variant comprising one or more substituted arginine and/or lysine residues resulting in increased protease resistance. In some embodiments, the D1L3 variant has a substitution at one or more positions corresponding to K180, K200, K259, and/or R285 of SEQ ID NO:4. In accordance with this disclosure, such lysine and arginine residues are identified as potential protease-sensitive sites. Thus, one or more (e.g., 1, 2, 3, or 4) of these residues may be modified with a non-charged residue, such as a residue independently selected from Ala, Gly, Leu, Ile, Val, Thr, Ser, and Pro. In some embodiments, protease-sensitive lysine or arginine residues are substituted as part of a building block substitution. For example, the D1L3 variant may comprise one or more substitutions selected from: K180_A181 delinsGL, P198_A201 delinsRPSQ, and K259A. In some embodiments, the D1L3 variant comprises one or both substitutions: K180_A181delinsGL, and/or P198_A201 delinsRPSQ, either of which are optionally modified by one or two amino acid substitutions, deletions, or insertions, with the proviso that the building block substitution is not modified by substitution or insertion with an R or K residue. In some embodiments, the D1L3 variant has increased resistance to proteolysis by one or more proteases selected from plasmin, thrombin, and/or trypsin.

Alternatively or in addition, the D1L3 variant comprises one or more mutations of a paired basic residue. In some embodiments, the paired basic residue corresponds to a position selected from K50/R51, R80/R81, K114/R115, K199/K200, K226/K227, K291/K292, R297/K298/K299, and K303/R304 of SEQ ID NO:4. In some embodiments, the D1L3 variant has one or more substitutions selected from a substitution corresponding to R114T, R114A, R114D, R114Q, K227S, and K227E of SEQ ID NO:4. In some embodiments, the one or more mutations of a paired basic residue include an amino acid substitution corresponding to R51K, R81K, R115K, and R304K. In some embodiments, the paired basic residue is substituted using a corresponding building block substitution. In accordance with these embodiments, the D1L3 variant will be more resistant to proteases expressed by the recombinant protein expression system (e.g., CHO and *Pichia pastoris*).

In some aspects, the invention provides a DNase 1 (D1) variant comprising an amino acid sequence that is at least 80% identical to the enzyme defined by SEQ ID NO: 1, with one or more substitutions of cysteine residues. In some embodiments, the D1 protein variant has one or more additional modifications resulting in increased protein stability, higher production levels with in vitro expression systems, and/or not substantially less, the same, or better DNA and/or chromatin and/or NET-degrading activity as compared to wild-type D1 protein of SEQ ID NO:1. For example, the D1 variant may comprise at least one additional building block substitution or point mutation disclosed in PCT/US2018/47084, which is hereby incorporated by reference in its entirety.

In some embodiments, the D1 variant has a substitution of one or both of C123 and C126, and which is/are optionally substituted with Ala, Ser, and Gly. In some embodiments, the D1 variant comprises the substitution G122_N128delinsYQGDA. In some embodiments, the D1 variant comprises an amino acid sequence that has at least 85%, at least 90%, at least 95%, or at least 98% identity to SEQ ID NO: 1.

In some embodiments, the invention provides a D1 enzyme having a PEG moiety conjugated at the position corresponding to C123 and/or C126. In these embodiments, the PEG moiety will provide a half-life extension property, while avoiding disulfide scrambling and/or protein misfolding. In some embodiments, the PEG moiety is conjugated through maleimide chemistry, which can be conducted under mild conditions. Other conjugation chemistries are known and may be used, such as vinyl sulfone, dithyopyridine, and iodoacetamide activation chemistries. The PEG moiety can be linear or branched, and can be generally in the range of 10 kDa to 40 kDa, or in the range of 20 to 30 kDa.

In other aspects, the invention provides a D1L1 variant comprising an amino acid sequence that is at least 80% identical to the enzyme defined by SEQ ID NO: 2, with one or more substituted cysteine residues. The cysteine residue(s) are optionally non-conserved within the D1 family (e.g., C22 and/or C50), and are optionally substituted with Gly, Arg, or Ser, or are substituted as part of a building block substitution. In some embodiments, the D1L1 variant comprises an amino acid sequence that has at least 85%, at least 90%, at least 95%, or at least 98% identity to SEQ ID NO: 2.

In some embodiments, the invention provides a D1L1 enzyme having a PEG moiety conjugated at the position corresponding to C22 and/or C50. In these embodiments, the PEG moiety will provide a half-life extension property, while avoiding disulfide scrambling and/or protein misfolding. In some embodiments, the PEG moiety is conjugated through maleimide chemistry, which can be conducted under mild conditions. Other conjugation chemistries are known and may be used, such as vinyl sulfone, dithyopyridine, and iodoacetamide activation chemistries. The PEG moiety can be linear or branched, and can be generally in the range of 10 kDa to 40 kDa, or in the range of 20 to 30 kDa.

In some aspects, the invention provides a D1L2 variant comprising an amino acid sequence that is at least 80% identical to the enzyme defined by SEQ ID NO: 3, with one or more substituted cysteine residues. The cysteine residues may be non-conserved within the D1 family (e.g., C43), and is/are optionally substituted with Gly, Arg, or Ser, or are substituted as part of a building block substitution. In some embodiments, the D1L2 variant comprises an amino acid sequence that has at least 85%, at least 90%, at least 95%, or at least 98% identity to SEQ ID NO: 3.

In some embodiments, the invention provides a D1L2 enzyme having a PEG moiety conjugated at the position corresponding to C43. In these embodiments, the PEG moiety will provide a half-life extension property, while avoiding disulfide scrambling and/or protein misfolding. In some embodiments, the PEG moiety is conjugated through maleimide chemistry, which can be conducted under mild conditions. Other conjugation chemistries are known and may be used, such as vinyl sulfone, dithyopyridine, and iodoacetamide activation chemistries. The PEG moiety can be linear or branched, and can be generally in the range of 10 kDa to 40 kDa, or in the range of 20 to 30 kDa.

In other aspects, the invention provides isolated polynucleotides encoding the D1, D1L1. D1L2, or D1L3 variants disclosed herein, as well as vectors and host cells. Host cells can be cells of any expression system, including bacterial or eukaryotic, whether non-mammalian such as *Pichia pastoris*, or mammalian such as CHO cells.

In some embodiments, delivery of polynucleotides is used for therapy. Encoding polynucleotides can be delivered as mRNA or as DNA constructs using known procedures, e.g., electroporation or cell squeezing, and/or vectors (including viral vectors), mRNA polynucleotides can include known modifications (mmRNA) to avoid activation of the innate immune system. See WO 2014/028429, which is hereby incorporated by reference in its entirety. In some embodiments, the polynucleotide is delivered to the body of a subject. In some embodiments, the polynucleotides is delivered into a cell in vitro, and the cell is delivered to the body of a subject. The cell can be, for example, a white blood cell (e.g., a T cell or macrophage), an endothelial cell, an epithelial cell, a hepatocyte, or a stem cell.

In other aspects, the invention provides a method for producing an extracellular DNASE variant described herein. The method comprises culturing cells expressing a polynucleotide encoding the extracellular DNASE, and recovering the recombinant DNase protein. The cells may be prokaryotic or eukaryotic. In some embodiments, the DNase is expressed using a non-mammalian expression system, which is optionally *Pichia pastoris* or *Saccharomyces* spp. In some embodiments, a mammalian expression system, such as CHO cells, is employed.

The invention further provides pharmaceutical compositions comprising the extracellular DNASE or variant thereof as described herein, or optionally the polynucleotide or the vector as described, and a pharmaceutically acceptable carrier.

A vector generally comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Exemplary vectors include autonomously replicating plasmids or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The pharmaceutical composition may be formulated for any administration route, including topical, parenteral, or pulmonary administration. In various embodiments, the composition is formulated for intradermal, intramuscular, intraperitoneal, intraarticular, intravenous, subcutaneous, intraarterial, oral, sublingual, pulmonary, or transdermal administration. In some embodiments, the composition is formulated for intravenous or subcutaneous administration.

In other aspects, the invention provides a method for treating a subject in need of extracellular DNA degradation, extracellular chromatin degradation, extracellular trap (ET) degradation and/or neutrophil extracellular trap (NET) degradation. The method comprises administering a therapeutically effective amount of the extracellular DNASE or variant thereof or composition described herein. Exemplary indications where a subject is in need of extracellular DNA or chromatin degradation (including ET or NET degradation) are disclosed in PCT/US18/47084, the disclosure of which is hereby incorporated by reference. In some embodiments, the invention provides a method for treating a subject in need thereof, the method comprising administering a therapeutically effective amount of a protein that is represented by any one of the sequences SEQ ID NO:8 to SEQ ID NO:30.

In each instance where a method for treating a subject is described, the invention likewise provides the use of one or more of the extracellular DNASE proteins for the treatment or prevention of diseases associated with ETs and/or NETs.

In various embodiments, the present invention provides a method for treating, preventing, or managing diseases or conditions characterized by the presence or accumulation of NETs. Such diseases or conditions include, but are not limited to, diseases associated with chronic neutrophilia, neutrophil aggregation and leukostasis, thrombosis and vascular occlusion, ischemia-reperfusion injury, surgical and traumatic tissue injury, an acute or chronic inflammatory reaction or disease, an autoimmune disease, cardiovascular disease, metabolic disease, systemic inflammation, inflammatory diseases of the respiratory tract, renal inflammatory diseases, inflammatory diseases related to transplanted tissue (e.g. graft-versus-host disease) and cancer (including leukemia).

In certain embodiments, the present invention pertains to the treatment of diseases or conditions characterized by deficiency of D1L3, or a deficiency of D1. In some cases, the subject has a mutation (e.g., a loss of function mutation) in the Dnase1l3 gene or the Dnase1 gene. Such subjects can manifest with an autoimmune disease (e.g., systemic lupus erythematosus (SLE) (including lupus nephritis), scleroderma or systemic sclerosis, rheumatoid arthritis, inflammatory bowel disease (including Crohn's disease and ulcerative colitis), and urticarial vasculitis). In some cases, the subject has an acquired inhibitor of D1 (e.g., anti-DNase1-antibody and actin) and/or D1L3 (e.g., anti-Dnase1l3-antibody). Such subjects can also have an autoimmune or inflammatory disease (e.g., SLE, systemic sclerosis).

In some embodiments, the subject has or is at risk of NETs occluding ductal systems. For example, the DNASE enzymes disclosed herein can be administered to a subject to treat pancreatitis, cholangitis, conjunctivitis, mastitis, dry eye disease, obstructions of vas deferens, or renal diseases.

In some embodiments, the subject has or is at risk of NETs accumulating on endothelial surfaces (e.g. surgical adhesions), the skin (e.g. wounds/scarring), or in synovial joints (e.g. gout and arthritis, e.g., rheumatoid arthritis). The DNASE enzymes described herein can be administered to a subject to treat a condition characterized by an accumulation of NETs on an endothelial surface such as, but not limited to, a surgical adhesion.

Other diseases and conditions associated with NETs, which the DNASE enzymes disclosed herein may be used to treat or prevent, include: ANCA-associated vasculitis, asthma, chronic obstructive pulmonary disease, a neutrophilic dermatosis, dermatomyositis, burns, cellulitis, meningitis, encephalitis, otitis media, pharyngitis, tonsillitis, pneumonia, endocarditis, cystitis, pyelonephritis, appendicitis, cholecystitis, pancreatitis, uveitis, keratitis, disseminated intravascular coagulation, acute kidney injury, acute respiratory distress syndrome, shock liver, hepatorenal syndrome, myocardial infarction, stroke, ischemic bowel, limb ischemia, testicular torsion, preeclampsia, eclampsia, and solid organ transplant (e.g., kidney, heart, liver, and/or lung transplant). Furthermore, the DNASE enzymes disclosed herein can be used to prevent a scar or contracture, e.g., by local application to skin, in an individual at risk thereof, e.g., an individual with a surgical incision, laceration, or burn.

In various embodiments, the subject has a disease that is or has been treated with wild-type Dnases, including D1 and streptodornase. Such diseases or conditions include thrombosis, stroke, sepsis, lung injury, atherosclerosis, viral infection, sickle cell disease, myocardial infarction, ear infection, wound healing, liver injury, endocarditis, liver infection, pancreatitis, primary graft dysfunction, limb ischemia reperfusion, kidney injury, blood clotting, alum-induced inflammation, hepatorenal injury, pleural exudations, hemothorax, intrabiliary blood clots, post pneumatic anemia, ulcers, otolaryngological conditions, oral infections, minor injuries, sinusitis, post-operative rhinoplasties, infertility, bladder catheter, wound cleaning, skin reaction test, pneumococcal meningitis, gout, leg ulcers, cystic fibrosis, Kartegener's syndrome, asthma, lobar atelectasis, chronic bronchitis, bronchiectasis, lupus, primary ciliary dyskinesia, bronchiolitis, empyema, pleural infections, cancer, dry eyes disease, lower respiratory tract infections, chronic hematomas, Alzheimer's disease, and obstructive pulmonary disease.

Other aspects and embodiments of the invention will be apparent from the following examples.

EXAMPLES

Nearly 70% of all biologics are produced using Chinese Hamster Ovary (CHO) cells. Indeed, wild-type DNASE1 (D1; dornase alpha) is typically produced in CHO cells. Despite significant advantages in cell line development and large-scale production using CHO cells, there still remains a significant challenge in the production of Dnase enzymes due to a considerable degree of variability and no reliable methods for predicting or modeling cell growth characteristics. Importantly, CHO cells were not able to stably produce hyperactive variants of D1, which prevented their clinical manufacturing, and prior to the present disclosure, the manufacturing properties of other DNASE1-protein family members, including DNASE1-LIKE 3 (D1L3), were unknown.

Using CHO and microbial expression systems, several challenges were identified in manufacturing of D1L3, including low production yield, proteolytic degradation, protein misfolding, and erroneous or undesired glycosylation. This disclosure provides technical solutions to these and other challenges in manufacturing, which also can improve the therapeutic properties of D1L3.

Example 1: Expression and Characterization of D1L3 with Basic Domain Deletion (BDD) in Chinese Hamster Ovarian (CHO) Cells and in *Pichia pastoris*

DNASE1 and DNASE1L3 preferentially cleave protein-free DNA and DNA-histone-complexes (i.e, chromatin), respectively. Previous studies suggest that a basic domain (BD) at the C-terminus of DNASE1L3, which is absent in DNASE1, is responsible for the distinct substrate specificities of both enzymes (Sisirak et al., Cell, 2016; Keyel, Developmental Biology, 2017).

A protein engineering technology, termed Building Block Protein Engineering is described in PCT/US18/47084 and U.S. 62/800,790, the disclosures of which are hereby incorporated by reference in their entireties. This approach can be applied to members of the DNASE1 and DNASE2-protein family. The method is based on the following steps: providing a protein-protein alignment of donor and recipient Dnase enzymes; identifying variable amino acid sequences for transfer, the variable amino acids being flanked by one or more conserved amino acids in the donor and recipient Dnase enzymes; substituting the variable amino acids of the recipient Dnase with the variable amino acids of the donor Dnase to create a chimeric Dnase; and recombinantly producing the chimeric Dnase.

To characterize the amino acids that are responsible for chromatin-degrading activity ("chromatinase" activity), wild-type D1L3 was substituted with building block substitutions from D1, as disclosed in PCT/US2018/047084. The building block substitutions to D1L3 are selected from human D1 and result in variants of human D1L3, which feature the following mutations: M21_R22delinsLK, C24 S25delinsAA, V28_S30delinsIQT, S34T, Q36_V44delinsMSNATLVSY, K47_K50delinsQILS, C52Y, I55_M58delinsIALVQE, I60_K61delinsVR, N64_I70 delinsHLTAVGK, M72_K74delinsLDN, R77_I83 delinsQDAPD, N86H, I89V, S91_R92delinsEP, T97S, Q101R, A103L, L105V, K107_L110delinsRPDQ, V113_R115delinsAVD, H118Y, H120D, Y122_A127delinsGCEPCGN, V129T, S131N, F135_V136delinsAI, W138R, Q140_H143delinFSRF, A145_D148delinsEVRE, V150A, I152V, T156_T157delinsAA, E159_S161delinsGDA, K163A, E167A, V169_E170delinsYD, T173L, K176_R178delinsQEK, K180_A181delinsGL, N183_F186delinsDVML, P198_A201delinsRPSQ, K203_N204delinsSS, R208W, D210S, R212T, V214Q, G218P, Q220_E221delinsSA, V225_S228delinsATP, N230H, L238_R239delinsVA, Q241_S246delinsMLLRGA, K250D, N252_V254delinsALP, D256N, K259A, K262G, T264_E267delinsSDQL, L269_V271delinsQAI, F275Y, F279_K280delinsVM, Q282_S205delinsK with respect to SEQ ID NO: 4.

Figure 1:
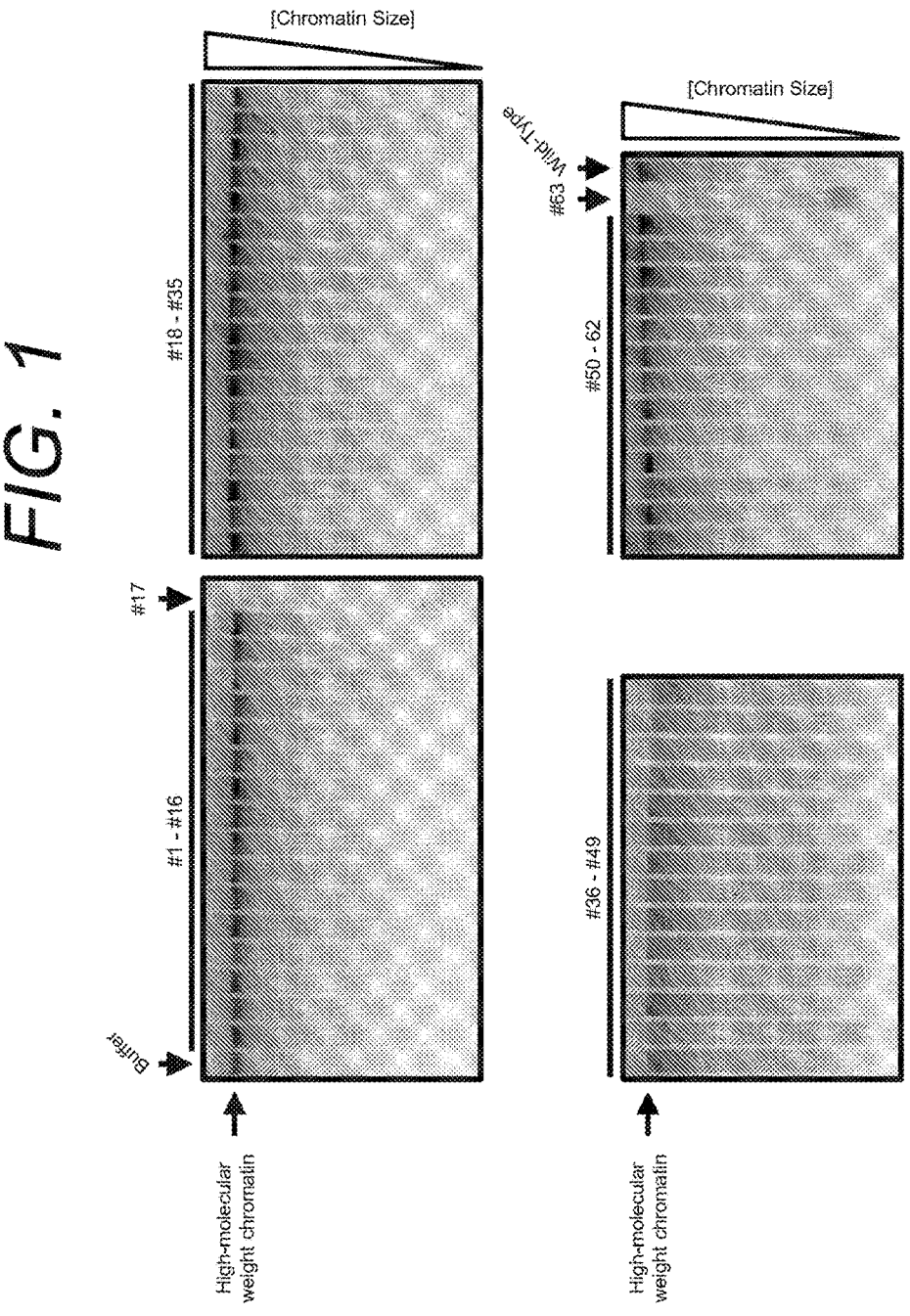
FIG. 1 illustrates that the mutations Q101R and Q282_S305delinsK in SEQ ID NO: 4 increase the activity to degrade high-molecular weight chromatin of DNASE1L3. CHO cells were transiently transfected with wild-type DNASE1L3 or DNASE1L3 with building block substitutions. Supernatants of transfected cells were incubated with purified nuclei (high-molecular weight chromatin) or buffer. DNA was isolated and analyzed by agarose gel electrophoresis. The figure shows the agarose gel stained with a DNA dye.
Figure 2:
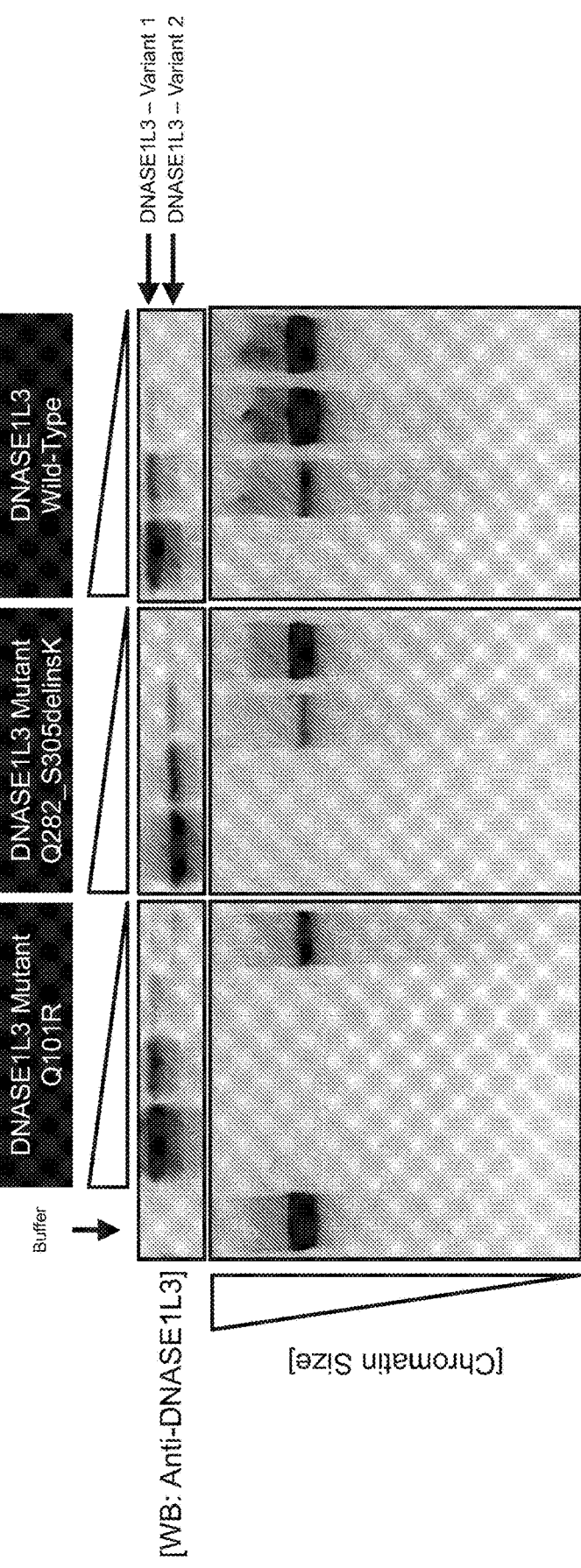
FIG. 2 shows that the characterization of two DNASE1L3 variants. Different concentrations of supernatants of CHO cell that were transfected with wild-type DNASE1L3 or DNASE1L3 with a Q101R or Q282_S305delinsK mutation were analyzed by Western Blot (WB) using an anti-DNASE1L3 antibody. A larger (variant 1) and a smaller (variant 2) bands were detected in samples with wild-type DNASE1L3 and the Q101R mutant. Only the smaller band (variant 2) was shown in samples with the Q282_S305delinsK mutant. In parallel, the chromatin degrading activity in the different concentrations of supernatants was analyzed. The figure shows DNA analyzed by agarose gel electrophoresis. Both, Q101R or Q282_S305delinsK mutations, increased the chromatin degrading activity compared to wild-type DNASE1L3.
Figure 3:
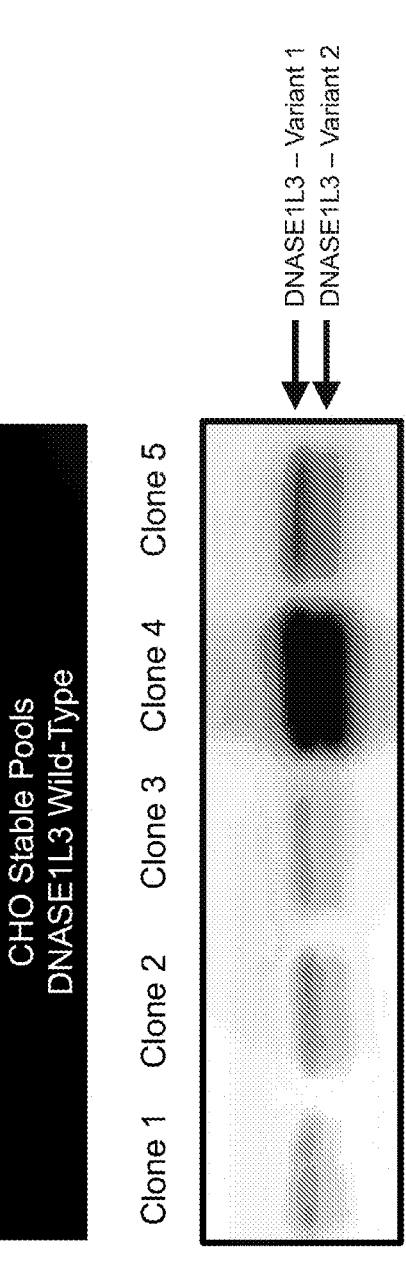
FIG. 3 illustrates the presence of DNASE1L3 variant 1 and 2 in supernatants of CHO cell that were stably transfected with wild-type DNASE1L3. Samples were analyzed by Western Blot (WB) using an anti-DNASE1L3 antibody. A larger (variant 1) and a smaller (variant 2) bands were detected in 5 clones.

These 63 D1L3 variants were screened for loss or gain of chromatin-degrading activity. In brief, D1L3 variants were transiently expressed in CHO cells using an in vitro expression vector. Culture supernatants were collected and tested for chromatin-degrading activity using purified nuclei as a source of chromatin. As shown in FIG. 1, the building block substitutions #17 and #63 from D1 significantly improved the degradation of high-molecular weight (HMW) chromatin to small fragments, when compared to wild-type D1L3. Building block substitution #7 causes a missense mutation Q101R, which replaces glutamine at position 101 with arginine (SEQ ID NO: 8). Building block substitution #63 causes the mutation Q282_S305delinsK, which deletes the full C-terminal BD of D1L3 from amino acid position 283 to 305 and replaces glutamine (Q) at position 282 with lysine (SEQ ID NO: 9). Next, we performed Western Blot analysis of the supernatants to detect the expression levels of wild-type D1L3 and both mutants (FIG. 2). To our surprise, we detected two D1L3 variants of different size in samples with wild-type D1L3 and the Q101R mutant. Samples with the Q282_S305delinsK contained only the smaller D1L3 variant. The data suggest that the BD of wild-type D1L3 is spontaneously removed (e.g., proteolyzed) during expression or post-secretion in CHO cells. The two D1L3 variants were also detected in supernatants from CHO cells that stably express WT-D1L3 (FIG. 3). Of note, the Basic Domain Deleted-D1L3 (BDD-D1L3) showed substantially increased chromatinase activity, when compared to wild-type D1L3.

Next, we tested *Pichia pastoris* as an alternative, microbial expression system to CHO cells. We generally observed higher expression levels with BDD-D1L3, when compared to wild-type D1L3. Here, we purified and characterized wild-type D1L3 and BDD-D1L3 from *Pichia pastoris* fermentation supernatants (FIG. 4). Unexpectedly, we observed that wild-type D1L3 was proteolytically truncated within the BD at the amino acid positions K291, K291, or S293, leading to a heterogenous mix of D1L3 variants after purification. Unlike wild-type D1L3, expression of BDD-D1L3 due to three building block substitutions (F275Y, F279_K280delinsVM, Q282_S205delinsK) generated a pure protein.

Next, we compared the chromatinase activity of both D1L3 purifications. We observed that the heterogenous mix of D1L3 variants with BD truncations at positions K291, K291, or S293 had approximately 10-fold lower chromatinase activity compared to the D1L3 variant with a full BD deletion due to F275Y/F279_K280delinsVM/Q282_S205delinsK. Collectively, the data illustrate that the proteolytic cleavage of the BD can occur naturally in microbial and mammalian expression systems (i.e. CHO and *P. pastoris*), and removal of the BD appears to activate D1L3 activity to degrade chromatin.

Example 2: Expression of D1L3 in CHO Cells in Bioreactors

Figure 5:
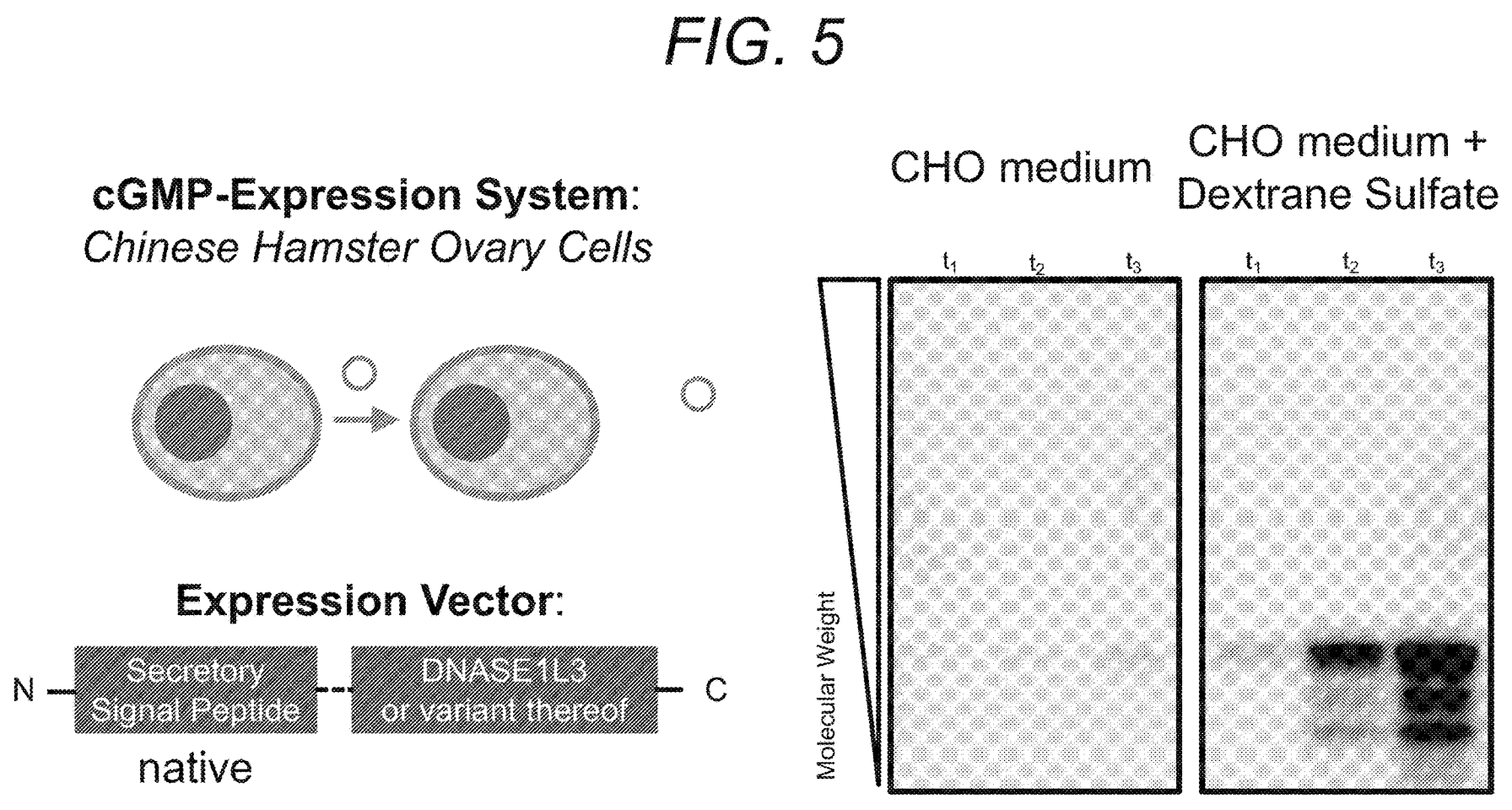

Disclosed herein is the development of stable CHO cell lines producing wild-type D1L3 (SEQ ID NO: 4). The cell lines were cultured in bioreactors using standard CHO culture medium. Specifically, FIG. 5 shows a Western Blot of human D1L3 expressed and secreted by CHO cells in a bioreactor under cGMP-compatible conditions. Samples were collected at different time points (t1-t3). Only minor levels of D1L3 and D1L3 fragments were detected. The data suggest that low production yield of D1L3 is a challenge in manufacturing of D1L3.

As disclosed herein, high production levels of wild-type D1L3 were achieved by the addition of polyanions to the culture medium. Such polyanions can comprise one or more of heparin, dextran sulfate, ferric citrate, and ethylenediaminetetraacetic acid, and represent the biologically active ingredient in "anti-cell clumping reagents". Specifically, we added dextran sulfate to the CHO culture medium and observed a strong increase in D1L3 as well as D1L3 fragments (FIG. 5). The data illustrate that polyanions increased production yield of D1L3, but did not prevent proteolytic degradation.

Figures 6A, 6B, 6C:
FIGS. 6A-C illustrate the use of anion exchange surface and cation exchange surface for affinity purification of dextran sulfate-complexed D1L3.

FIG. 6A shows that polyanions, such as dextran sulfate (DS), form a complex with D1L3. The D1L3-DS-complex prevents the interaction and scavenging of D1L3 by negatively charged surfaces during the production process. Such negatively charged surfaces include, but are not limited to, the cell surface of production cells (e.g. CHO cells, *Pichia pastoris, Saccharomyces* spp.), DNA exposed by dying cells, and bioreactor surfaces. FIG. 6B and FIG. 6C show the two-step purification process of D1L3 from DS-D1L3-complexes. As shown in FIG. 6, the first step aims to dissociate the DS-D1L3 complex. The dissociation can be achieved by incubating the DS-D1L3 complex with strong anion exchange surfaces, which bind DS and thus liberate D1L3. Specifically, the purification process can include the passage of culture medium containing the DS-D1L3 through a chromatography column that is filled with a strong anion exchange resin followed by the collection of the flow through, which contains the DS-free D1L3. The second step of the purification process is shown in FIG. 6C and includes the affinity purification of D1L3 from the DS-free flow through via the application of a strong cation exchange resin. In conclusion, the production yield of D1L3 can be substantially increased through the addition of polyanions, such as dextran sulfate.

Example 3: Engineering D1L3 for Protease Resistance

Wild-type D1L3 contains 50 arginine and lysine residues, which makes the enzyme particularly susceptible to proteases like trypsin, thrombin, and plasmin. In this example, trypsin and plasmin cleavage sites were identified in D1L3. The sites can be mutated to generated protease-resistance variants of D1L3.

In brief, purified D1L3 was digested with trypsin. D1L3 fragments were isolated, and the amino acid sequence of the fragments determined using combinations of liquid chromatography (LC) and mass spectrometry (MS). It was identified that trypsin cleaved D1L3 at the following arginine and lysine residues: R22, R29, R51, R66, R80, R81, R95, K99, R115, K147, K163, K180, R208, R212, R235, R239, K250, and K262. These arginine and lysine residues can be substituted with small amino acids such as alanine, valine, and serine or with amino acids that have similar properties according to the Grantham's distance score (e.g. histidine, glutamine, and glutamate; FIG. 7). D1, which is protease resistant, features arginine and lysine residues corresponding to R51, R95, K99, and R235, suggesting that these residues are not primarily responsible for proteolytic degradation of D1L3.

Building Block Protein Engineering was applied to transfer the following Building Blocks from D1 to replace Building Blocks of D1L3 that contain the trypsin cleavage sites (FIG. 7): R22 (Mutation: M21_R22delinsLK), R29 (V28_S30delinsIQT), R66 (N64_I170 delinsHLTAVGK), R80 (R77_I83 delinsQDAPD), R81 (R77_I83 delinsQDAPD), R115 (V113_R115delinsAVD), K163 (K163A), K180 (K180)_A181 delinsGL), R208 (R208W) MR212 (R212T), R239 (L238_R239delinsVA), K250) (K250D), and K262 (K262G).

Plasmin is a plasma protease that is generated by activation of its zymogen plasminogen. Plasminogen activator inhibitor 1 (PAI-1) inhibits the activation of plasmin. Interestingly, PAI-1 increases the enzymatic activity of D1L3 in serum, suggesting that plasmin may proteolytically inactivate D1L3. However, the plasmin cleavage sites in D1L3 have not been identified.

Figure 8:
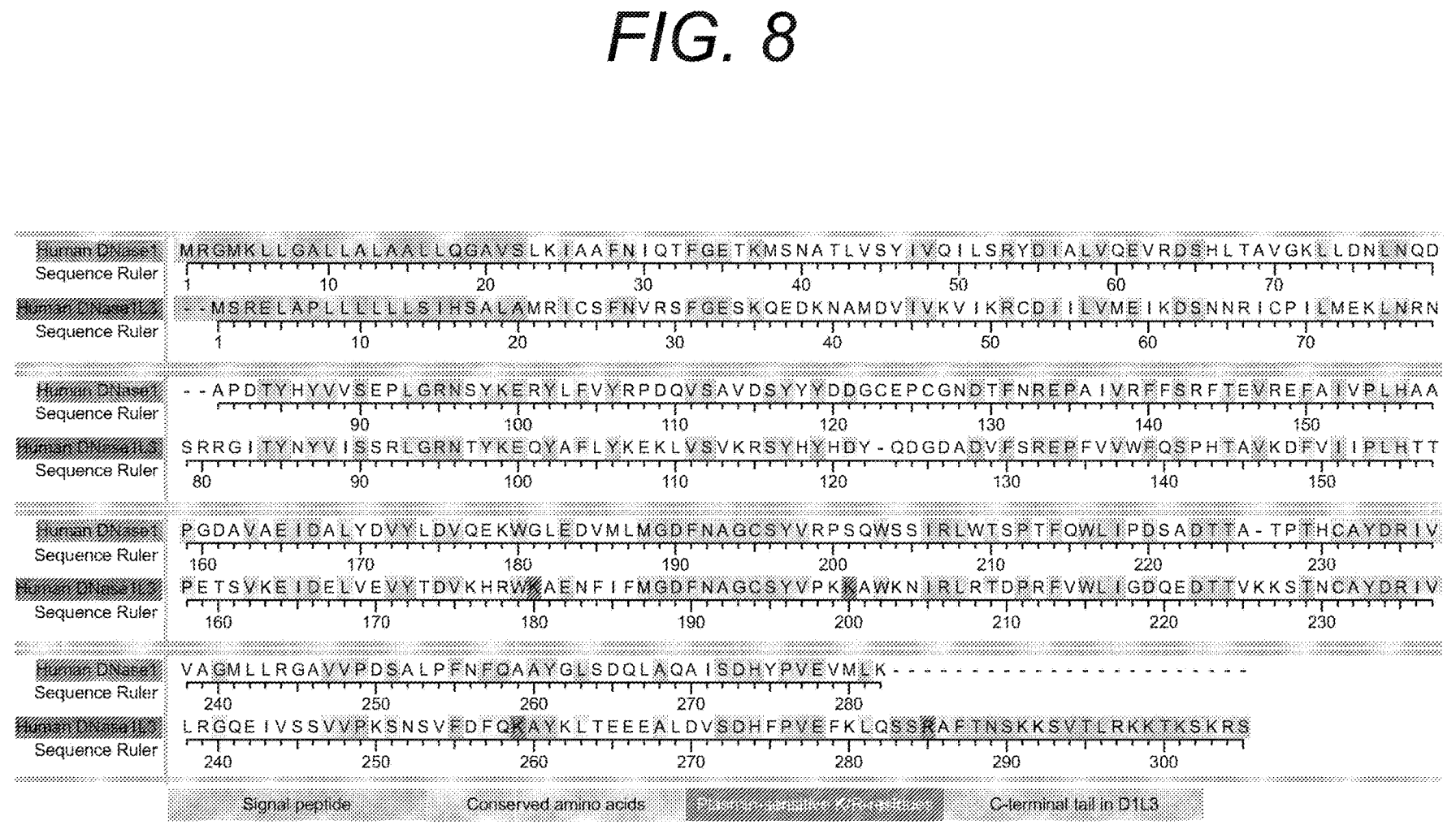
Figure 10:
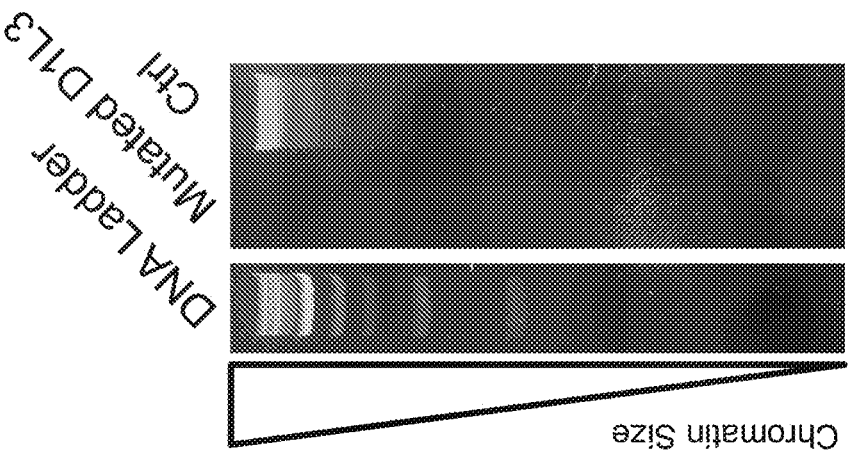
FIG. 10 shows that D1L3 with plasmin cleavage sites mutated retains enzymatic activity. Supernatants from cells that were transiently transfected DNASE1L3 containing mutations in four putative plasmid cleavage sites (K180_A181delinsGL, P198_A201delinsRPSQ, K259A, R285A) were incubated with purified nuclei (high-molecular weight chromatin) or buffer. DNA was isolated and analyzed by agarose gel electrophoresis. The figure shows the agarose gel stained with a DNA dye.

In silico analysis showed that the amino acid combination lysine-alanine (KA) or arginine-alanine (RA) is believed to be preferably cleaved by the protease plasmin or proteases that have plasmin-like activity. D1L3 contains a total of four putative plasmin-cleavage sites (FIG. 8): (Site 1) K180/A181 (K160/A161 without signal peptide), (Site 2) K200/A201 (K180/A181 without signal peptide), (Site 3) K259/A260) (K239/A240) without signal peptide), and (Site 4) R285/A286 (R270/A250 without signal peptide). Using a paired alignment of D1 and D1L3, we found that none of the plasmin cleavage sites are present in D1 (FIG. 8). The data are in line with the fact that D1 activity is resistant to inactivation by serum proteases, such as thrombin and plasmin. Building Block Protein Engineering was applied to transfer the following Building Blocks from D1 to replace Building Blocks of D1L3 that contain the plasmin cleavage sites (FIG. 9): (Site 1) K180_A181delinsGL, (Site 2) P198_A201delinsRPSQ, and (Site 3) K259A. R285/A286 (Site 4) is located in a C-terminal extension that is absent in D1. Consequently, we generated a D1L3 variant in which all four putative plasmin cleavage sites were mutated: K180_A181delinsGL, P198_A201delinsRPSQ. K259A, and R285A. Next, we analyzed chromatin degradation by the D1L3 variant and observed potent chromatin degrading activity in the mutated D1L3 (FIG. 10). Collectively, the data show that four arginine and lysine residues, K180, K200, K259, and R285, can be mutated to reduce the risk of proteolytic degradation without compromising enzymatic activity.

Next, purified D1L3 was digested with purified plasmin. D1L3 fragments were isolated, and the amino acid sequence of the fragments determined using combinations of LC and MS. We identified that plasmin cleaved D1L3 at the following arginine and lysine residues: R22, R29, K45, K47, K74, R81, R92, K107, K176, R212, R226, R227, K250, K259, and K262. These arginine and lysine residues can be substituted with small amino acids such as alanine, valine, and serine or with amino acids that have similar properties according to the Grantham's distance score (e.g. histidine, glutamine, and glutamate; FIG. 11). D1, which is protease resistant, features a lysine residue corresponding to K45, suggesting that this residue is not primarily responsible for proteolytic degradation of D1L3 by plasmin. Building Block Protein Engineering was applied to transfer the following Building Blocks from D1 to replace Building Blocks of D1L3 that contain the trypsin cleavage sites in silico (FIG. 11): R22 (Mutation: M21_R22delinsLK), R29 (V28_S30delinsIQT), K47 (K47_K50delinsQILS), K74 (M72_K74delinsLDN), R81 (R77_I83 delinsQDAPD), R92 (S91_R92delinsEP), K107 (K107_L110delinsRPDQ), K176 (K176_R178delinsQEK), R212 (R212T), K226 (V225_S228delinsATP), K227 (V225_S228delinsATP), K250 (K250D), K259 (K259A), and K262 (K262G).

Finally, recombinantly expressed wild-type D1L3 was isolated and its C-terminus sequenced. Three different amino acid sequences were identified ending in S290 (SEQ ID NO: 10), K291 (SEQ ID NO: 11), and K292 (SEQ ID NO: 12), respectively (FIG. 4. Example 1). The data identify lysine residues 291 and 292 as prominent proteolytic cleavage sites of D1L3 during large-scale manufacturing.

Example 4: Engineering D1L3 to Avoid Degradation

We observed fragmentation of D1L3 after heterologous expression in *Pichia pastoris*. Analysis of the fragments characterized paired basic amino acids, arginine (R) and lysine (K) residues, as proteolytic cleavage sites. A similar degradation pattern was observed after expressing D1L3 in CHO cells. These observations suggest that *Pichia pastoris* and CHO cells share homologous proteases that cleave D1L3 at paired basic amino acids, and although the effect was more significant in CHO cells.

It was determined that the paired basic amino acid cleaving enzyme (PACE) contributed to the DNASE1L3 fragmentation. PACE, also known as Furin (Uniprot ID: P09958), is expressed in humans and mammals. *Pichia pastoris* expresses two enzymes, which target paired basic amino acids, namely Aspartic proteinase 3 (Gene: Ysp1; Uniprot ID: P32329) and Kexin (Gene: Kex2; Uniprot ID: P13134). Thus, DNASE1L3 and DNASE1L3 variants can be expressed in *Pichia pastoris* and in CHO cells in which Furin, Aspartic proteinase 3, and Kexin is pharmacologically inhibited or genetically depleted.

In addition, mutations of paired basic amino acids in DNASE1L3 and DNASE1L3 variants enable their expression in CHO and *Pichia pastoris* with reduced fragmentation. Analysis of DNASE1L3 fragments identified feature paired basic amino acid at positions: K50/R51, R80/R81, K114/R115, K199/K200, K226/K227, K291/K292, R297/K298/K299, and K303/R304 in SEQ ID NO: 2.

As disclosed U.S. Provisional Patent Application No. 62/800,790 (which is hereby incorporated by reference in its entirety), DNASE1L3 from other species feature amino acid substitutions at these cleavage sites, including R114T (Mouse), R114A (Rat), R114D (Guinea pig), R114Q (Cow), K227S (Dog), and K227E (Elephant). These amino acid substitutions can be applied to human DNASE1L3 to render the enzyme resistant to proteolytic degradation, including during expression in CHO cells and *Pichia pastoris*.

Kexin preferably cleaves after KR and RR residues. DNASE1L3 features at K50/R51, R80/R81, K114/R115, and K303/R304 are 4 KEX2-cleavage sites. Amino acid substitutions of these residues render DNASE1L3 resistant to KEX2 and enable the expression of DNASE1L3 and DNASE1L3 variants in *Pichia pastoris* and in CHO cells. These amino acid substitutions can be conservative, e.g. R51K, R81K, R115K, and R304K.

Example 5: Engineering D1L3 Variants to Prevent High-Molecular Weight Aggregates During cGMP-compatible expression of D1L3 in CHO cells (FIG. 12A), the accumulation of high-molecular weight aggregates of D1L3 was observed, pointing towards an additional challenge for clinical manufacturing D1L3. The high molecular weight aggregates were observed by a much lower extent in *Pichia pastoris*.

Figures 12A, 12B:
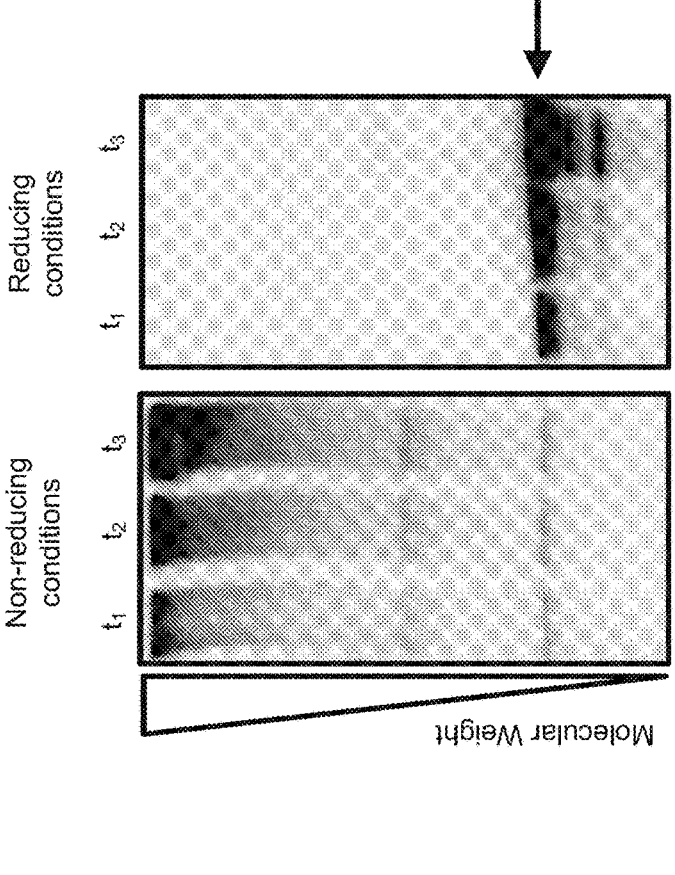
FIGS. 12A-B show that D1L3 has a propensity to misfold when expressed in CHO cells.

The application of reducing conditions to proteins of bioreactor material dissolved D1L3 aggregates. The data illustrate that D1L3 aggregate formation is caused by intra- and/or inter-molecular cross-linking via disulfide bridges during protein expression. Specifically, as shown in FIG. 12B, the gel was run under non-reducing conditions and shows the accumulation of high-molecular weight aggregates of D1L3 over time. The gel was run under reducing conditions and no aggregates were detected. The data illustrate that erroneous intra- and inter-molecular disulfide bonds cause misfolding of human D1L3 under manufacturing conditions.

Figure 13:
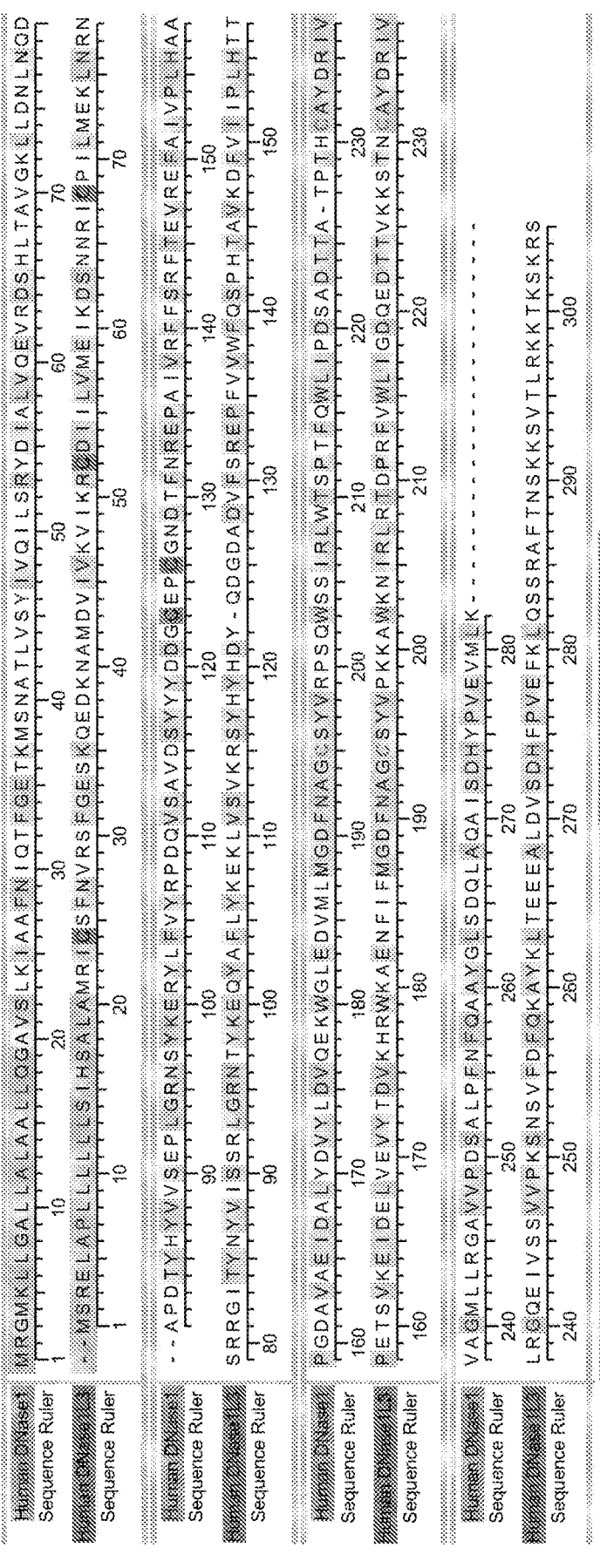
FIG. 13 is an alignment of human D1 (SEQ ID NO: 1) and human D1L3 (SEQ ID NO: 4) amino acid sequences, with conserved and non-conserved cysteine residues shown.

FIG. 13 shows an amino acid sequence alignment of human D1 (SEQ ID NO: 1) and human D1L3 (SEQ ID NO: 4). The signal peptide, conserved amino acids, variable amino acids, non-conserved cysteine residues, and conserved cysteine residues are highlighted. Mutations in non-conserved cysteine residues will reduce the possibilities of intra- and inter-molecular disulfide bonds during protein expression. Analysis of the amino acid sequence of D1L3 (SEQ ID NO: 4) showed the presence of five cysteine (C) residues: C24, C52, C68, C194, and C231 (FIG. 14), The cysteine residues C194 and C231 are conserved among all members of the DNASE1-protein family and form disulfide bonds that are required for enzymatic activity of DNASE1. The function of cysteine residues in D1L3 were not known prior to the present disclosure. Accordingly, as disclosed herein, mutation of these cysteine residues reduces the cross-linking via disulfide bridges and thus increases the yield of protein production.

Figure 15:
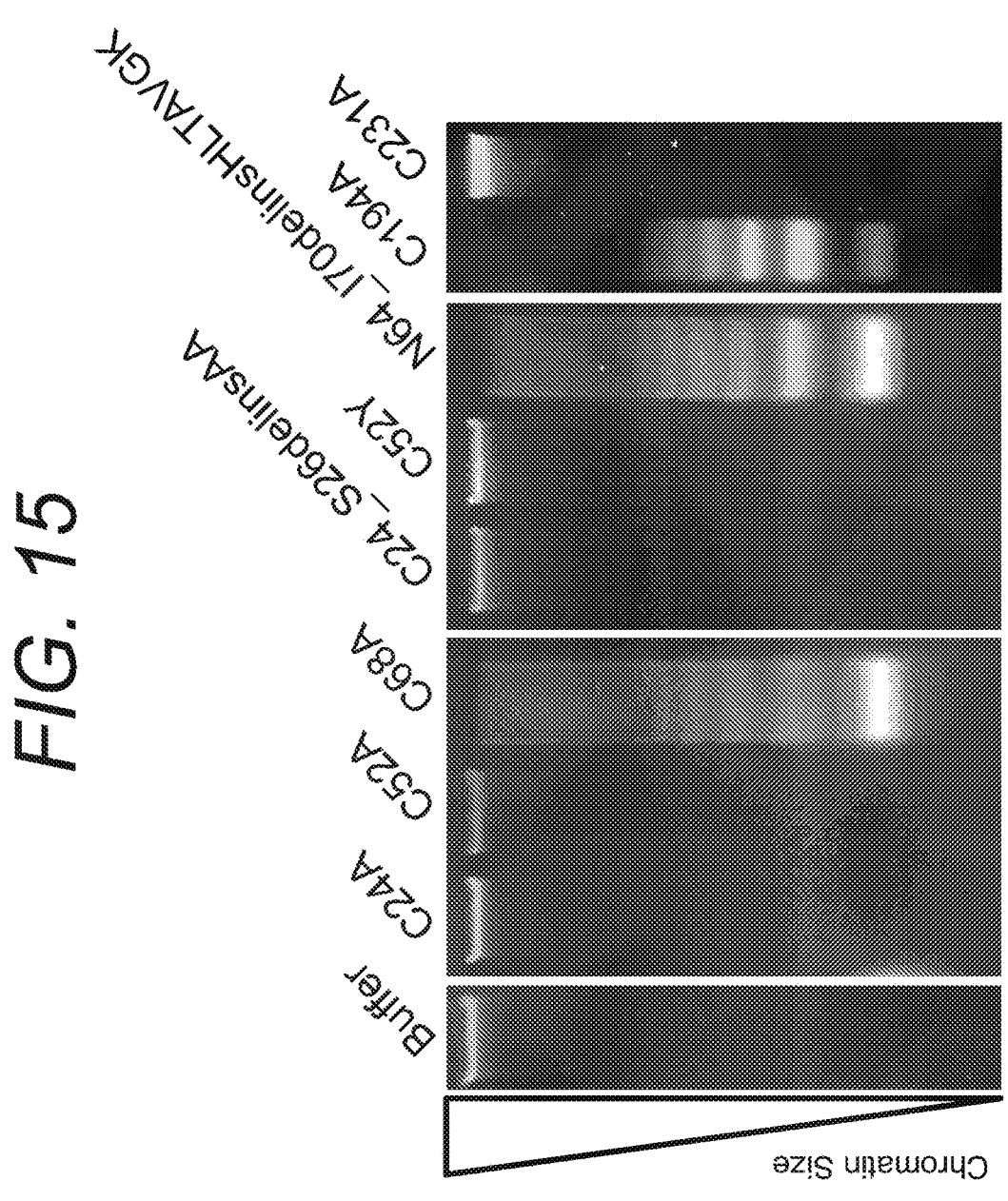
FIG. 15 shows that C68A and C194A mutation in D1L3 does not impact chromatin degrading activity. The mutations C24A and C52A abrogated chromatin-degrading activity. Supernatants from cells that were transiently transfected with mutated DNASE1L3 variants were incubated with purified nuclei or buffer. DNA was isolated and analyzed by agarose gel electrophoresis. The figure shows the agarose gel stained with a DNA dye.

Cysteine residues can be substituted with other small amino acids, namely alanine (A), serine (S), and glycine (G), among others. Such substitutions cause the following amino acid mutations C24A/S/G, C52A/S/G, C68A/S/G, C194A/S/G, and C231A/S/G. In addition, Building Blocks that comprise the conserved cysteine residues can be replaced by Building Blocks from a donor DNase of the DNASE1-protein family (e.g. D1 and D1L3). The following Building Blocks from D1 were used to replace the Building Blocks of D1L3 that contain the non-conserved cysteine residues C24, C52, and C68: C24_S25delinsAA, C52Y, and N64_I70 delinsHLTAVGK. The chromatin degrading activity of D1L3 variants was quantified, as described in PCT/US18/4708. Both conventional amino acids substitutions (C24A, C52A) and building block substitutions (C24_S25delinsAA, C52Y) caused a complete absence of chromatin degradation, indicating that C24 and C52 are required for D1L3 activity (FIG. 15). Importantly, mutation of cysteine C68, either by conventional amino acid substitution [C68A, (SEQ ID NO: 13)] or by BB mutation (N64_I70 delinsHLTAVGK), resulted in a D1L3 variant with chromatin degrading activity (FIG. 15). Amino acid sequence alignment showed that cysteine C68 is not conserved among other DNASE1-protein family members, supporting the notion that C68 is not required for enzymatic activity. Furthermore, it was observed that the amino acid substitution of highly conserved cysteine C194 with alanine (C194A), but not the mutation of the highly conserved cysteine C231 with alanine (C231A), resulted in an enzymatically active D1L3 variant (FIG. 15). Thus, cysteine C68 and C194 can be mutated to reduce the risk of erroneous disulfide bonds during D1L3 production.

A similar approach can be applied to mutate the non-conserved cysteine residues in the other members of the DNase1 protein family: D1. DNase1-like 1 (D1L1) and DNase1-like 2 (D1L2). D1 has two non-conserved cysteine: C123 and C126. D1L1 shows two non-conserved cysteine residues (C22, C50) that correspond to C24 and C52 in D1L2 has only one non-conserved cysteine residues: C43. Mutation of non-conserved cysteine residues of members of the DNASE1 protein family will reduce cross-linking via erroneous disulfide bridges during protein expression and thus allow for manufacturing of D1, D1L1, D1L2, and D1L3 for therapeutic applications.

Example 6: Construction and Expression of D1L3 and Albumin-D1L3 Fusion Proteins in *Pichia pastoris*

Figures 16A, 16B:
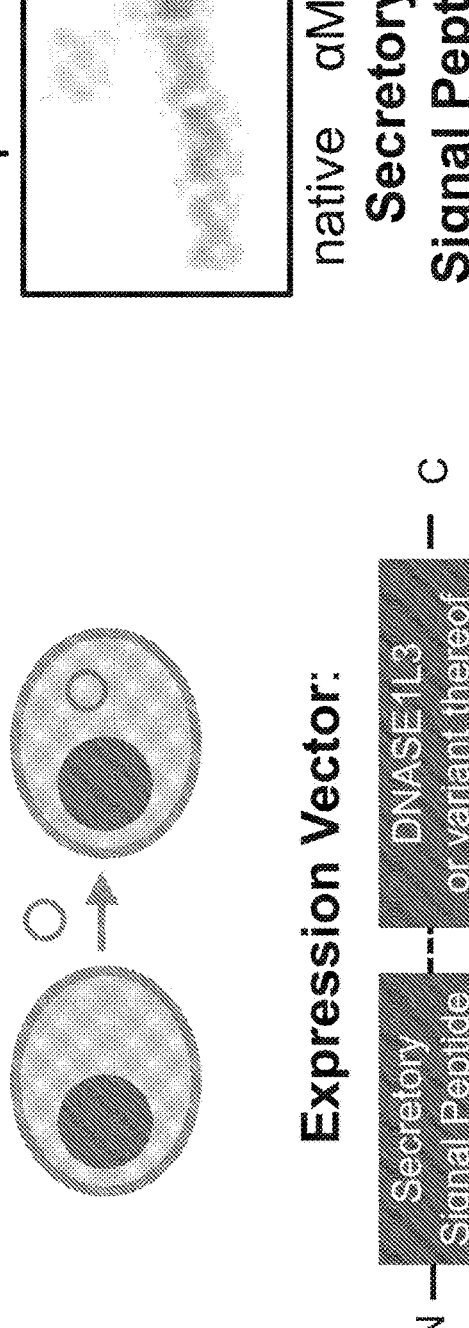
FIGS. 16A-B illustrate the expression of D1L3 in *Pichia pastoris* using either the native secretory signal or α-mating factor from *Saccharomyces cerevisiae* (αMF).
Figures 17A, 17B, 17C:
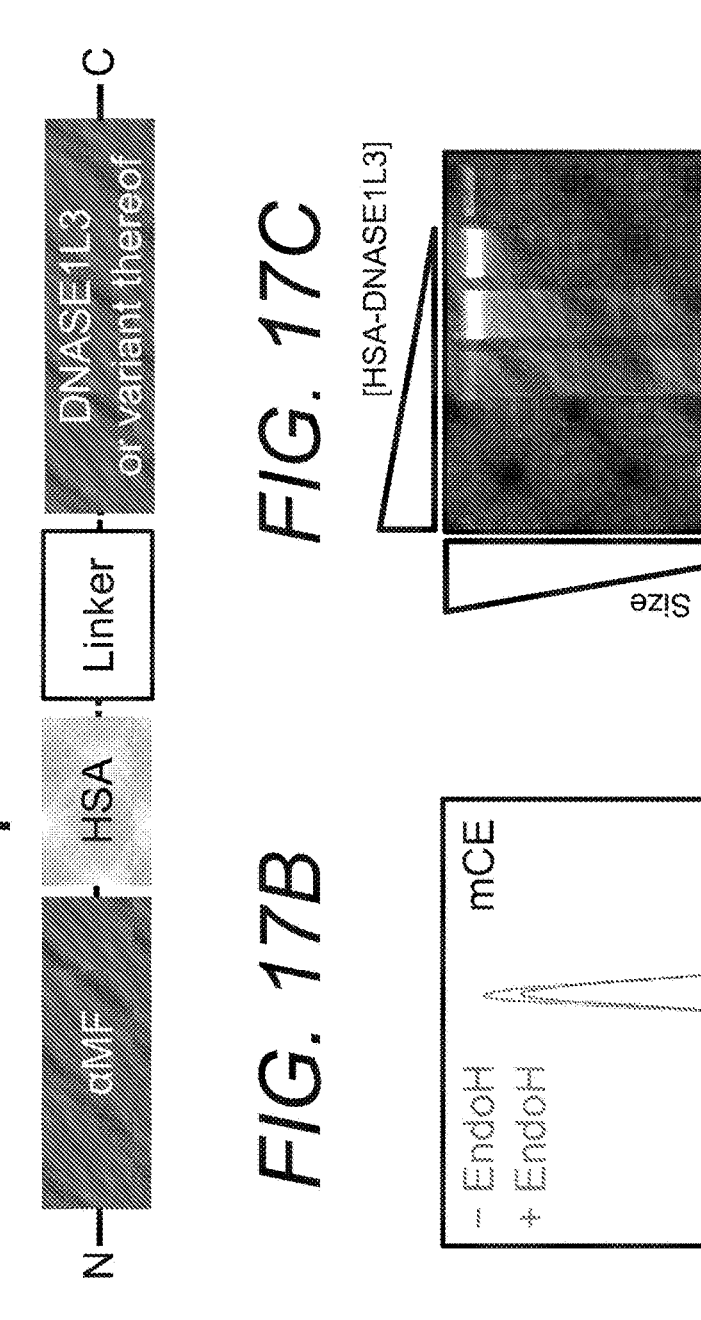
FIGS. 17A-C illustrate that a fusion construct of αMF, human serum albumin (HSA), linker sequence, and D1L3 is not glycosylated in *P. pastoris* expression system, and retains chromatin-degrading activity.

*Pichia pastoris* expression of recombinant human extracellular DNASES, including D1L3, was tested. As shown in FIG. 16A, the N-terminus of D1L3 was led by the alpha-mating factor (aMF) pre-pro secretion leader from *Saccharomyces cerevisiae* (SEQ ID NO: 46), a common tool for heterologous protein expression in *Pichia pastoris*. As disclosed herein, the combination of aMF with D1L3 caused the unexpected non-processing of aMF due to glycosylation (FIG. 16B). The glycosylation of the D1L3 protein prevents the use of *P. pastoris* for clinical manufacturing of D1L3. D1L3 was properly processed, when N-terminus was led by native secretory signal peptide of D1L3 [FIG. 16B, (SEQ ID NO: 48)]. Importantly, aMF increased D1L3 expression 3-5-fold, when compared to the native signal peptide of D1L3. We therefore tested the processing of D1L3-fusion proteins. In pilot studies, an N-terminal fusion of aMF and human serum albumin [HSA, (SEQ ID NO: 39)] to D1L3 was generated (FIG. 17A). Some variants contained linker peptide [e.g. (GSSSS)$_3$] between HSA and D1L3. As shown in FIG. 17B and FIG. 17C, expression of the fusion protein in *P. pastoris* generated a non-glycosylated and enzymatically active D1L3. Furthermore, the expression levels were 5-10-fold increased, when compared to native secretory signal peptide-driven expression of D1L3. Collectively, the data illustrate that fusion of D1L3 to albumin enables manufacturing in *Pichia pastoris*.

Based on these pilot studies, various HSA fusion constructs of wild-type D1L3 and BDD-D113 were designed and screened for expression levels of target protein (SEQ ID NOS: 17 to 28). As shown in FIG. 18, we observed that the N-terminal fusion of human serum albumin (SEQ ID: NO: 17) to a BDD-D113 variant (SEQ ID NO: 16) did not substantially increase the expression levels. However, of note, we did detect a strong increase in expression levels when we inserted a flexible linker composed of glycine (G) and serine (S) residues between HSA and BDD-D1L3. Furthermore, the length of the linker sequence correlated with increased expression. For example, while 12±1.9 relative Units of expression were obtained with a 5 amino acid linker (SEQ ID NO: 18), and with a 15 amino acid linker (SEQ ID NO: 19) expression was 32±3.2 relative Units, an approximately 7.5-fold improvement over the HSA-fusion without a linker. Furthermore, the N-terminal location was critical for the improved expression levels because C-terminal fusion of the linker-HSA constructs were expressed at low levels (SEQ ID NO: 20, SEQ ID NO: 21). Of note, the N-terminal fusion of HSA via a flexible linker also robustly increased the expression of wild-type D1L3 (SEQ ID NO: 22), approximately 20-fold over native D1L3 (SEQ ID NO: 4). In conclusion, the fusion of HSA via a linker to the N-terminus enable the production of D1L3 as well as BDD-D1L3 variants.

Next, we tested whether the nature of the linker sequence was critical for the improvement of D1L3 expression. We tested two additional sequences. APAPAPAPAPAPAP (SEQ ID NO: 33, 14 amino acids, rigid linker) and AEAAAKEAAAKA (SEQ ID NO: 34, 12 amino acids, rigid helical linker). As shown in FIG. 19, in both test constructs (SEQ ID NO: 23, SEQ ID NO: 24), we observed a strong increase in expression, but the rigid helical linker did not achieve similar strong expression levels as observed for GGGGSGGGGSGGGGS linker. Thus, the length and the acid composition of the linker impacted levels of D1L3 expression.

Figure 20:
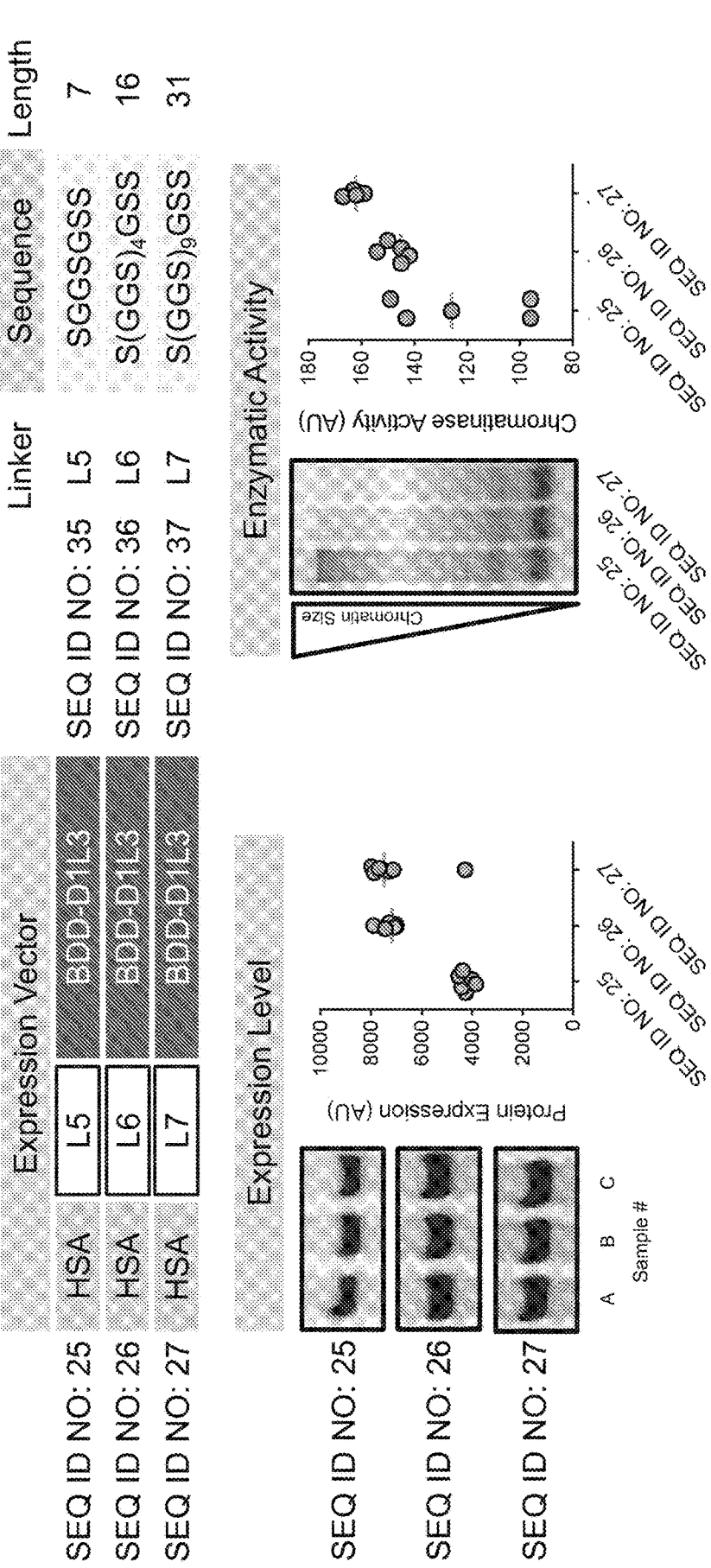
FIG. 20 illustrates the expression levels and chromatin degrading activity of human serum albumin (HSA) fusion constructs of Basic Domain Deleted-DNASE1L3 (BDD-D1L3) produced in *Pichia pastoris*. The HSA is fused to the N-terminus of BDD-D1L3. Three different linker sequences (L5, L6, L7) were placed between HSA and D1L3.

Next, we analyzed the relationship between linker length, expression level, and enzymatic activity. For these tests, designed expression vectors comprising N-terminal fusion of HSA with a GS-linker to the BDD-D1L3 variants (SEQ ID NO: 25 to 27). Three different linker lengths were tested SGGSGSS [7 amino acids, (SEQ ID NO: 35)]. SGGSGGSGGSGGSGSS [16 amino acids, (SEQ ID NO: 36)], and SGGSGGSGGSGGSGGSGGSGGSGGSGSS [31 amino acids, (SEQ ID NO: 37)]. As shown in FIG. 20, we observed that elongation of the linker sequence from 7 amino acids to 16 amino acids resulted in an increase in expression level. Further elongation from 16 to 31 amino acids did not increase protein expression but increased the enzymatic activity as detected by the degradation of HMW-chromatin into LMW-chromatin. Biologics fused to albumin fusion often show a reduced activity because albumin sterically hinders the interaction with substrates and ligands. Thus, peptide linkers can be used to increase the distance between albumin and the fusion protein or peptide. However, the observation that insertion of a linker sequence between HSA and D1L3 simultaneously improves enzymatic activity and expression levels was unexpected.

Figure 21B:
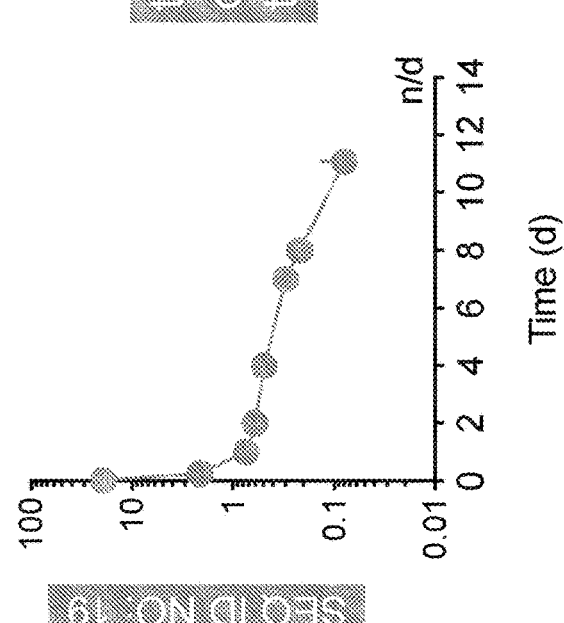
FIGS. 21A-B show the serum chromatin degrading activity and circulation half-life of albumin D1L3 fusion proteins.
Figure 21A:
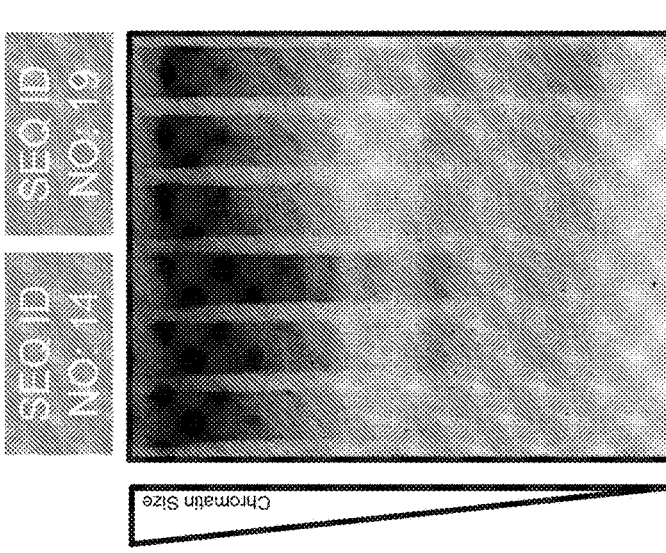

We compared the chromatin degrading activity of BDD-D1L3 (SEQ ID NO: 14) with its albumin-fusion counterpart (SEQ ID NO: 19). In brief, Dnase1$^{-/-}$ Dnase1l3$^{-/-}$ mice were injected with SEQ ID NO:4 or SEQ ID NO:19. Serum was collected 15 minutes post injection. As shown in FIG. 21A, we observed similar serum chromatin degrading activity in both animals. Importantly, the fusion of albumin to the N-terminus of D1L3 and other human extracellular DNASES provides a half-life extended DNASE therapeutics. As disclosed herein, we determined the half-life of SED ID NO: 19, an HSA-BDD-D1L3 fusion protein with a flexible, GS-linker of 15 amino acids, in a commercially available rodent model. The animal model is characterized by the transgenic expression of the human FcRn, which is responsible for long half-life of albumin in circulation. While unconjugated D1L3 (e.g. SEQ ID NO: 4) has a very short half-life in circulation (<30 minutes), the albumin fusion extended the half-life to 3.3 days, thereby substantially improving systemic exposure, while also conferring rapid absorption with a t$_{max}$ of 5 minutes (FIG. 21B). Collectively, the data demonstrate the N-terminal fusion of HSA to D1L3 via a linker sequence not only facilitates the manufacturing, but also improves the in vivo pharmacokinetic properties of D1L3.

Figure 22:
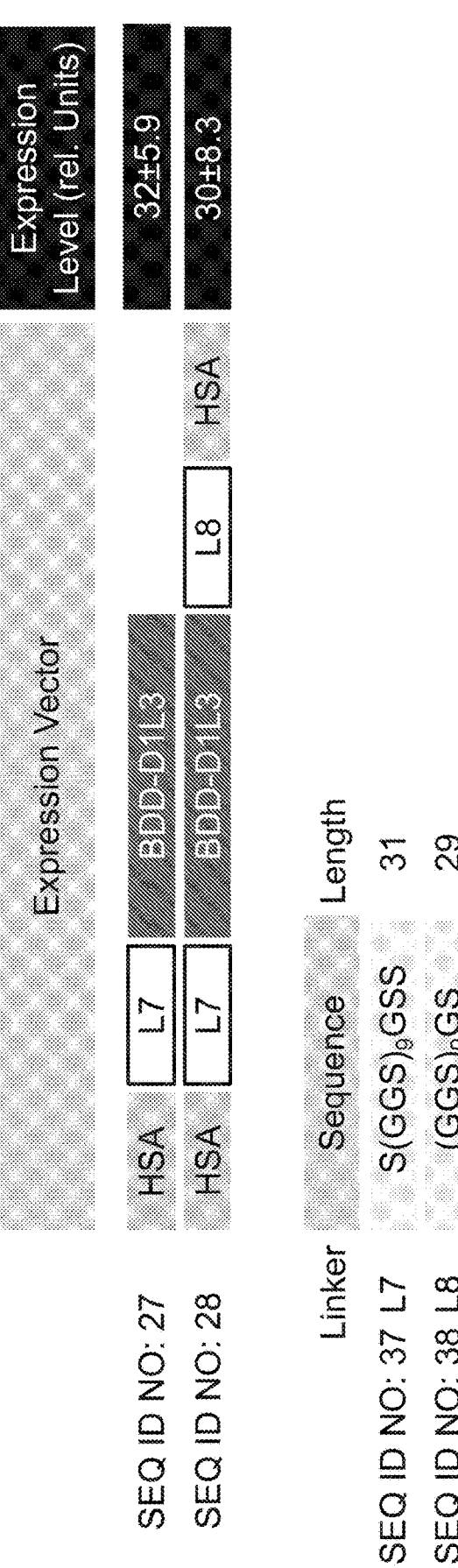
FIG. 22 illustrates the expression levels and chromatin degrading activity of human serum albumin (HSA) fusion constructs of Basic Domain Deleted-DNASE1L3 (BDD-

Finally, we tested the dual fusion of HSA to the N- and C-terminus of D1L3. First, we analyzed the C-terminus of D1L3 for potential attachment sites. We identified two serine residues at position 283 and 284, which provide a flexible connection of the BD (RAFTNSKKSVTLRKKTKSKRS) to the core body of D1L3. Thus, we deleted the BD and chose to attach HSA via a flexible GS-linker (SEQ ID NO: 38) to S284. As shown in FIG. 22, fusion of HSA to the N- and C-terminus of BDD-D1L3 (SEQ ID NO: 28) maintained the high expression levels that were observed with N-terminal HSA fusion (SEQ ID NO: 27).

Example 7: Design of Cleavable Linker Sequences

The findings disclosed herein have implications beyond manufacturing. For example, D1L3 variants with C-terminal amino acid deletions, which retain their enzymatic activity to degrade chromatin and/or NETs, as exemplified by SEQ ID NO: 9 to SEQ ID NO: 12, can be used for D1L3 therapy. In addition, the site-specific alkylation of an unpaired cysteine thiol is commonly used to generate half-life extended biologics for therapeutic applications. Specifically, the non-essential cysteines C68 and C194 of D1L3 can be used for site specific PEGylation (PEG, polyethylene glycol). Furthermore, D1L3 variants that are resistant to inactivation by plasmin, due to mutations such as K180_A181delinsGL, P198_A201delinsRPSQ, K259A, and R285A, are expected to have an improved half-life and thus efficacy in therapeutic applications.

Importantly, the fusion of albumin to the N-terminus of D1L3 and other human extracellular DNASES provides a half-life extended DNASE therapeutic (FIG. 23A). Several linker sequences were used to reduce the steric inhibition of D1L3 by albumin. In addition, a physiologically cleavable peptide linker was developed. The linker peptide was designed to be cleared when the fusion protein is in close proximity to neutrophil extracellular traps (NETs). Peptide sequences that are targeted by neutrophil specific proteases, such as neutrophil elastase, cathepsin G, and proteinase 3, are candidates for the cleavable linker sequence.

A cleavable linker sequence was developed that is cleaved intravascularly and thus optimal for intravenously and intraarterially applied DNASE therapeutics. To design the peptide, we considered that NETs have the capacity to activate blood clotting factors, in particular the clotting factor XII (FXII). Activated FXII (FXIIa) has two major substrates: clotting factor XI (FXI, SEQ ID NO: 40) and prekallikrein (PK, SEQ ID NO: 41). An amino acid sequence alignment showed that the FXIIa cleavage site is conserved in FXI and PK (FIG. 23B). In FXI, the cleavage site is between arginine 387 and isoleucine 388. In PK, the cleavage site is between arginine 390 and isoleucine 391. Indeed, FXI and PK are homologous proteins. As disclosed herein, we designed several linker peptides that contain all or parts of the FXI sequence position 380 to position 403 (SEQ ID NO: 42, SEQ ID NO: 43) or of the PK sequence position 383 to position 406 (SEQ ID NO: 44).

Finally, the FXIIa-cleavable linker can be used for manufacturing half-life extended version of other biologics (FIG. 24), including, but not limited to, variants of other extracellular DNASE, human coagulation factors (e.g. Factor VII, Factor VIII, and Factor IX), and complement factors (e.g. Factor H).

All patents and patent publications cited herein are hereby incorporated by reference in their entireties.

```
Wild-Type Human DNASES
DNASE1 (NP_005212.2): Signal Peptide, Mature Protein:
                                                    SEQ ID NO: 1
MRGMKLLGALLALAALLQGAVSLKIAAFNIQTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTENREPAIVRFFSRFTEVREFAIVPLHAAPGDAVAEIDALYDVYL

DVQEKWGLEDVMLMGDFNAGCSYVRPSQWSSIRLWTSPTFQWLIPDSADTTATPTHCA

YDRIVVAGMLLRGAVVPDSALPENFQAAYGLSDQLAQAISDHYPVEVMLK

DNASE1-LIKE 1 (NP_006721.1): Signal Peptide; Mature Protein:
                                                    SEQ ID NO: 2
MHYPTALLFLILANGAQAFRICAFNAQRLTLAKVAREQVMDTLVRILARCDIMVLQEV

VDSSGSAIPLLLRELNRFDGSGPYSTLSSPQLGRSTYMETYVYFYRSHKTQVLSSYVY

NDEDDVFAREPFVAQFSLPSNVLPSLVLVPLHTTPKAVEKELNALYDVFLEVSQHWQS

KDVILLGDFNADCASLTKKRLDKLELRTEPGFHWVIADGEDTTVRASTHCTYDRVVLH
```

-continued

GERCRSLLHTAAAFDEPTSFQLTEEEALNISDHYPVEVELKLSQAHSVQPLSLTVLLL

LSLLSPQLCPAA

DNASE1-LIKE 2 (NP_001365.1): <u>Signal Peptide</u>, Mature Protein:

SEQ ID NO: 3

<u>MGGPRALLAALWALEAAGTAAL</u>RIGAFNIQSFGDSKVSDPACGSIIAKILAGYDLALV

QEVRDPDLSAVSALMEQINSVSEHEYSFVSSQPLGRDQYKEMYLFVYRKDAVSVVDTY

LYPDPEDVESREPFVVKFSAPGTGERAPPLPSRRALTPPPLPAAAQNLVLIPLHAAPH

QAVAEIDALYDVYLDVIDKWGTDDMLFLGDFNADCSYVRAQDWAAIRLRSSEVEKWLI

PDSADTTVGNSDCAYDRIVACGARLRRSLKPQSATVHDFQEEFGLDQTQALAISDHFP

VEVTLKFHR

DNASE1-LIKE 3; Isoform 1 (NP_004935.1): <u>Signal Peptide</u>, Mature Protein:

SEQ ID NO: 4

<u>MSRELAPLLLLLLSIHSALAM</u>RICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVFSREPFVVWFQSPHTAVKDEVIIPLHTTPETSVKEIDELVEVYTD

VKHRWKAENFIFMGDENAGCSYVPKKAWKNIRLRTDPRFVWLIGDQEDTTVKKSTNCA

YDRIVLRGQEIVSSVVPKSNSVFDFQKAYKLTEEEALDVSDHFPVEFKLQSSRAFTNS

KKSVTLRKKTKSKRS

DNASE1-LIKE 3, Isoform 2 (NP_001243489.1): <u>Signal Peptide</u>; Mature Protein:

SEQ ID NO: 5

<u>MSRELAPLLLLLLSIHSALAM</u>RICSFNVRSFGESKQEDKNAMDVIVKVIKRCDIILVM

EIKDSNNRICPILMEKLNREKLVSVKRSYHYHDYQDGDADVESREPFVVWFQSPHTAV

KDFVIIPLHTTPETSVKEIDELVEVYTDVKHRWKAENFIFMGDENAGCSYVPKKAWKN

IRLRTDPRFVWLIGDQEDTTVKKSTNCAYDRIVLRGQEIVSSVVPKSNSVEDFQKAYK

LTEEEALDVSDHFPVEFKLQSSRAFTNSKKSVTLRKKTKSKRS

DNASE2A (O00115): <u>Signal Peptide</u>; Mature Protein:

SEQ ID NO: 6

MIPLLLAALLCVPAGALTCYGDSGQPVDWFVVYKLPALRGSGEAAQRGLQYKYLDESS

GGWRDGRALINSPEGAVGRSLQPLYRSNTSQLAFLLYNDQPPQPSKAQDSSMRGHTKG

VLLLDHDGGFWLVHSVPNFPPPASSAAYSWPHSACTYGQTLLCVSFPFAQFSKMGKQL

TYTYPWVYNYQLEGIFAQEFPDLENVVKGHHVSQEPWNSSITLTSQAGAVFQSFAKFS

KFGDDLYSGWLAAALGTNLQVQFWHKTVGILPSNCSDIWQVLNVNQIAFPGPAGPSFN

STEDHSKWCVSPKGPWTCVGDMNRNQGEEQRGGGTLCAQLPALWKAFQPLVKNYQPCN

GMARKPSRAYKI

DNASE2B (Q8WZ79): <u>Signal Peptide</u>; Mature Protein:

SEQ ID NO: 7

<u>MKQKMMARLLRTSFALLFLGLFGVLGAA</u>TISCRNEEGKAVDWFTFYKLPKRQNKESGE

TGLEYLYLDSTTRSWRKSEQLMNDTKSVLGRTLQQLYEAYASKSNNTAYLIYNDGVPK

PVNYSRKYGHTKGLLLWNRVQGFWLIHSIPQFPPIPEEGYDYPPTGRRNGQSGICITF

KYNQYEAIDSQLLVCNPNVYSCSIPATFHQELIHMPQLCTRASSSEIPGRLLTTLQSA

QGQKFLHFAKSDSFLDDIFAAWMAQRLKTHLLTETWQRKRQELPSNCSLPYHVYNIKA

IKLSRHSYFSSYQDHAKWCISQKGTKNRWTCIGDLNRSPHQAFRSGGFICTQNWQIYQ

AFQGLVLYYESCK

-continued

Human DNASE1L3 variants
DNASE1-LIKE 3, Q101R (Signal Peptide; Mature Protein)

SEQ ID NO: 8

MSRELAPLLLLLLLSIHSALAMRICSFNVRSFGESKQEDKNAMDVIVKVIKRCDIILVM

EIKDSNNRICPILMEKLNRNSRRGITYNYVISSRLGRNTYKERYAFLYKEKLVSVKRS

YHYHDYQDGDADVESREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVEDFQKAYKLTEEEALDVSDHFPVEFKLQSSRAFTNS

KKSVTLRKKTKSKRS

DNASE1L3, Q282_S305delinksK (Signal Peptide; Mature Protein):

SEQ ID NO: 9

MSRELAPLLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVEDFQKAYKLTEEEALDVSDHFPVEFKLK

DNASE1L3, S305delinsK (Signal Peptide; Mature Protein):

SEQ ID NO: 10

MSRELAPLLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWGLENFIFMGDFNAGCSYVRPSQWKNIRLRTDPRFVWLIGDQEDTTVKKSTNCA

YDRIVLRGQEIVSSVVPKSNSVFDFQAAYKLTEEEALDVSDHFPVEFKLQSSRAFTNS

DNASE1L3, K292_S305del (Signal Peptide; Mature Protein):

SEQ ID NO: 11

MSRELAPLLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDEVIIPLHTTPETSVKEIDELVEVYTD

VKHRWGLENFIFMGDENAGCSYVRPSQWKNIRLRTDPRFVWLIGDQEDTTVKKSTNCA

YDRIVLRGQEIVSSVVPKSNSVFDFQAAYKLTEEEALDVSDHFPVEFKLQSSRAFTNS

K

DNASE1L3, S293_S305del (Signal Peptide; Mature Protein):

SEQ ID NO: 12

MSRELAPLLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWGLENFIFMGDENAGCSYVRPSQWKNIRLRTDPRFVWLIGDQEDTTVKKSTNCA

YDRIVLRGQEIVSSVVPKSNSVFDFQAAYKLTEEEALDVSDHFPVEFKLQSSRAFTNS

KK

DNASE1L3, C68A (Signal Peptide; Mature Protein):

SEQ ID NO: 13

MSRELAPLLLLLLLSIHSALAMRICSFNVRSFGESKQEDKNAMDVIVKVIKRCDIILVM

EIKDSNNRIAPILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVEDFQKAYKLTEEEALDVSDHFPVEFKLQSSRAFTNS

KKSVTLRKKTKSKRS

-continued

DNASE1L3, F275Y/F279_K280delinsVM/Q282_S305delinsK (Signal Peptide;
Mature Protein):

SEQ ID NO: 14

MSRELAPLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDEVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHYPVEVMLK

DNASE1L3, S283_S305del (Signal Peptide; Mature Protein):

SEQ ID NO: 15

MSRELAPLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVEDFQKAYKLTEEEALDVSDHFPVEFKLQ

DNASE1L3, R285_S305del (Signal Peptide; Mature Protein):

SEQ ID NO: 16

MSRELAPLLLLLLSIHSALAMRICSFNVRSFGESKQEDKNAMDVIVKVIKRCDIILVM

EIKDSNNRICPILMEKLNREKLVSVKRSYHYHDYQDGDADVFSREPFVVWFQSPHTAV

KDFVIIPLHTTPETSVKEIDELVEVYTDVKHRWKAENFIFMGDENAGCSYVPKKAWKN

IRLRTDPRFVWLIGDQEDTTVKKSTNCAYDRIVLRGQEIVSSVVPKSNSVEDFQKAYK

LTEEEALDVSDHFPVEFKLQSS

Albumin Fusions with DNASE1L3 and Variants
Albumin - DNASE1L3 Variant - Fusion Protein. (Albumin, DNASE1L3 Variant):

SEQ ID NO: 17

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLMRICSFNVRSFGESKQEDKNAMDVIVKVIKRCDIILVMEIKDSNNRICPILME

KLNRNSRRGITYNYVISSRLGRNTYKEQYAFLYKEKLVSVKRSYHYHDYQDGDADVFS

REPFVVWFQSPHTAVKDFVIIPLHTTPETSVKEIDELVEVYTDVKHRWKAENFIFMGD

FNAGCSYVPKKAWKNIRLRTDPRFVWLIGDQEDTTVKKSTNCAYDRIVLRGQEIVSSV

VPKSNSVFDFQKAYKLTEEEALDVSDHYPVEVMLK

Albumin - DNASE1L3 Variant - Fusion Protein. (Albumin, DNASE1L3 Variant):

SEQ ID NO: 18

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

-continued

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLGGGGSMRICSFNVRSFGESKQEDKNAMDVIVKVIKRCDIILVMEIKDSNNRIC

PILMEKLNRNSRRGITYNYVISSRLGRNTYKEQYAFLYKEKLVSVKRSYHYHDYQDGD

ADVFSREPFVVWFQSPHTAVKDFVIIPLHTTPETSVKEIDELVEVYTDVKHRWKAENF

IFMGDFNAGCSYVPKKAWKNIRLRTDPRFVWLIGDQEDTTVKKSTNCAYDRIVLRGQE

IVSSVVPKSNSVFDFQKAYKLTEEEALDVSDHYPVEVMLK

Albumin - DNASE1L3 Variant - Fusion Protein. (Albumin, DNASE1L3 Variant):

SEQ ID NO: 19

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLGGGGSGGGGSGGGGSMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVFSREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHYPVEVMLK

DNASE1L3 Variant - Albumin - Fusion Protein. (Albumin, DNASE1L3 Variant):

SEQ ID NO: 20

MRICSFNVRSFGESKQEDKNAMDVIVKVIKRCDIILVMEIKDSNNRICPILMEKLNRN

SRRGITYNYVISSRLGRNTYKEQYAFLYKEKLVSVKRSYHYHDYQDGDADVFSREPFV

VWFQSPHTAVKDFVIIPLHTTPETSVKEIDELVEVYTDVKHRWKAENFIFMGDFNAGC

SYVPKKAWKNIRLRTDPRFVWLIGDQEDTTVKKSTNCAYDRIVLRGQEIVSSVVPKSN

SVFDFQKAYKLTEEEALDVSDHYPVEVMLKGGGGSDAHKSEVAHRFKDLGEENFKALV

LIAFAQYLQQCPFEDHVKLVNEVTEFAKTCVADESAENCDKSLHTLFGDKLCTVATLR

ETYGEMADCCAKQEPERNECFLQHKDDNPNLPRLVRPEVDVMCTAFHDNEETFLKKYL

YEIARRHPYFYAPELLFFAKRYKAAFTECCQAADKAACLLPKLDELRDEGKASSAKQR

LKCASLQKFGERAFKAWAVARLSQRFPKAEFAEVSKLVTDLTKVHTECCHGDLLECAD

DRADLAKYICENQDSISSKLKECCEKPLLEKSHCIAEVENDEMPADLPSLAADFVESK

DVCKNYAEAKDVFLGMFLYEYARRHPDYSVVLLLRLAKTYETTLEKCCAAADPHECYA

KVFDEFKPLVEEPQNLIKQNCELFEQLGEYKFQNALLVRYTKKVPQVSTPTLVEVSRN

LGKVGSKCCKHPEAKRMPCAEDYLSVVLNQLCVLHEKTPVSDRVTKCCTESLVNRRPC

FSALEVDETYVPKEFNAETFTFHADICTLSEKERQIKKQTALVELVKHKPKATKEQLK

AVMDDFAAFVEKCCKADDKETCFAEEGKKLVAASQAALGL

DNASE1L3 Variant - Albumin - Fusion Protein. (Albumin, DNASE1L3 Variant):

SEQ ID NO: 21

MRICSFNVRSFGESKQEDKNAMDVIVKVIKRCDIILVMEIKDSNNRICPILMEKLNRN

SRRGITYNYVISSRLGRNTYKEQYAFLYKEKLVSVKRSYHYHDYQDGDADVFSREPFV

VWFQSPHTAVKDFVIIPLHTTPETSVKEIDELVEVYTDVKHRWKAENFIFMGDENAGC

SYVPKKAWKNIRLRTDPRFVWLIGDQEDTTVKKSTNCAYDRIVLRGQEIVSSVVPKSN

SVFDFQKAYKLTEEEALDVSDHYPVEVMLKGGGGSGGGGSGGGGSDAHKSEVAHRFKD

LGEENFKALVLIAFAQYLQQCPFEDHVKLVNEVTEFAKTCVADESAENCDKSLHTLFG

DKLCTVATLRETYGEMADCCAKQEPERNECFLQHKDDNPNLPRLVRPEVDVMCTAFHD

NEETFLKKYLYEIARRHPYFYAPELLFFAKRYKAAFTECCQAADKAACLLPKLDELRD

EGKASSAKQRLKCASLQKFGERAFKAWAVARLSQRFPKAEFAEVSKLVTDLTKVHTEC

CHGDLLECADDRADLAKYICENQDSISSKLKECCEKPLLEKSHCIAEVENDEMPADLP

SLAADFVESKDVCKNYAEAKDVELGMFLYEYARRHPDYSVVLLLRLAKTYETTLEKCC

AAADPHECYAKVEDEFKPLVEEPQNLIKQNCELFEQLGEYKFQNALLVRYTKKVPQVS

TPTLVEVSRNLGKVGSKCCKHPEAKRMPCAEDYLSVVLNQLCVLHEKTPVSDRVTKCC

TESLVNRRPCFSALEVDETYVPKEFNAETFTFHADICTLSEKERQIKKQTALVELVKH

KPKATKEQLKAVMDDFAAFVEKCCKADDKETCFAEEGKKLVAASQAALGL

Albumin - DNASE1L3 - Fusion Protein. (Albumin, DNASE1L3):

SEQ ID NO: 22

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVELGMELYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLGGGGSGGGGSGGGGSMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVFSREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHFPVEFKLQSSRAFTNS

KKSVTLRKKTKSKRS

Albumin - DNASE1L3 - Fusion Protein. (Albumin, DNASE1L3):

SEQ ID NO: 23

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

-continued

KLVTDLTKVHTECCHGDLLECADDRADLAKYICENQDSISSKLKECCEKPLLEKSHCI

AEVENDEMPADLPSLAADFVESKDVCKNYAEAKDVELGMELYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLAPAPAPAPAPAPAPMRICSFNVRSFGESKQEDKNAMDVIVKVIKRCDIILVME

IKDSNNRICPILMEKLNRNSRRGITYNYVISSRLGRNTYKEQYAFLYKEKLVSVKRSY

HYHDYQDGDADVFSREPFVVWFQSPHTAVKDFVIIPLHTTPETSVKEIDELVEVYTDV

KHRWKAENFIFMGDFNAGCSYVPKKAWKNIRLRTDPRFVWLIGDQEDTTVKKSTNCAY

DRIVLRGQEIVSSVVPKSNSVFDFQKAYKLTEEEALDVSDHFPVEFKLQSSRAFTNSK

KSVTLRKKTKSKRS

Albumin - DNASE1L3 - Fusion Protein. (Albumin, DNASE1L3):

SEQ ID NO: 24

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLAEAAAKEAAAKAMRICSFNVRSFGESKQEDKNAMDVIVKVIKRCDIILVMEIK

DSNNRICPILMEKLNRNSRRGITYNYVISSRLGRNTYKEQYAFLYKEKLVSVKRSYHY

HDYQDGDADVFSREPFVVWFQSPHTAVKDFVIIPLHTTPETSVKEIDELVEVYTDVKH

RWKAENFIFMGDFNAGCSYVPKKAWKNIRLRTDPRFVWLIGDQEDTTVKKSTNCAYDR

IVLRGQEIVSSVVPKSNSVFDFQKAYKLTEEEALDVSDHFPVEFKLQSSRAFTNSKKS

VTLRKKTKSKRS

Albumin - DNASE1L3 Variant - Fusion Protein. (Albumin, DNASE1L3 Variants):

SEQ ID NO: 25

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGSSMRICSFNVRSFGESKQEDKNAMDVIVKVIKRCDIILVMEIKDSNNR

ICPILMEKLNRNSRRGITYNYVISSRLGRNTYKEQYAFLYKEKLVSVKRSYHYHDYQD

GDADVFSREPFVVWFQSPHTAVKDFVIIPLHTTPETSVKEIDELVEVYTDVKHRWKAE

NFIFMGDFNAGCSYVPKKAWKNIRLRTDPRFVWLIGDQEDTTVKKSTNCAYDRIVLRG

QEIVSSVVPKSNSVFDFQKAYKLTEEEALDVSDHFPVEFKLQ

Albumin - DNASE1L3 Variant - Fusion Protein. (Albumin, **DNASE1L3
Variant**):

SEQ ID NO: 26

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGGSGSS**MRICSFNVRSFGESKQEDKNAMDVIVKVIKRCDIILV

MEIKDSNNRICPILMEKLNRNSRRGITYNYVISSRLGRNTYKEQYAFLYKEKLVSVKR

SYHYHDYQDGDADVFSREPFVVWFQSPHTAVKDFVIIPLHTTPETSVKEIDELVEVYT

DVKHRWKAENFIFMGDFNAGCSYVPKKAWKNIRLRTDPRFVWLIGDQEDTTVKKSTNC

AYDRIVLRGQEIVSSVVPKSNSVFDFQKAYKLTEEEALDVSDHFPVEFKLQ**

Albumin - DNASE1L3 Variant - Fusion Protein. (Albumin, **DNASE1L3
Variant**):

SEQ ID NO: 27

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVELGMELYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGGSGGSGGSGGSGSS**MRICSFNVRSFGESKQEDKNAM

DVIVKVIKRCDIILVMEIKDSNNRICPILMEKLNRNSRRGITYNYVISSRLGRNTYKE

QYAFLYKEKLVSVKRSYHYHDYQDGDADVFSREPFVVWFQSPHTAVKDFVIIPLHTTP

ETSVKEIDELVEVYTDVKHRWKAENFIFMGDFNAGCSYVPKKAWKNIRLRTDPRFVWL

IGDQEDTTVKKSTNCAYDRIVLRGQEIVSSVVPKSNSVFDFQKAYKLTEEEALDVSDH

FPVEFKLQ**

-continued

Albumin - DNASE1L3 Variant - Albumin - Fusion Protein. (Albumin, DNASE1L3 Variant):

SEQ ID NO: 28

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVELGMELYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGGSGGSGGSGGSGGSGGSGSSMRICSFNVRSFGESKQEDKNAM

DVIVKVIKRCDIILVMEIKDSNNRICPILMEKLNRNSRRGITYNYVISSRLGRNTYKE

QYAFLYKEKLVSVKRSYHYHDYQDGDADVFSREPFVVWFQSPHTAVKDFVIIPLHTTP

ETSVKEIDELVEVYTDVKHRWKAENFIFMGDFNAGCSYVPKKAWKNIRLRTDPRFVWL

IGDQEDTTVKKSTNCAYDRIVLRGQEIVSSVVPKSNSVFDFQKAYKLTEEEALDVSDH

FPVEFKLQSSGGSGGSGGSGGSGGSGGSGGSGGSGGSGGSGSDAHKSEVAHRFKDLGEENF

KALVLIAFAQYLQQCPFEDHVKLVNEVTEFAKTCVADESAENCDKSLHTLFGDKLCTV

ATLRETYGEMADCCAKQEPERNECFLQHKDDNPNLPRLVRPEVDVMCTAFHDNEETFL

KKYLYEIARRHPYFYAPELLFFAKRYKAAFTECCQAADKAACLLPKLDELRDEGKASS

AKQRLKCASLQKFGERAFKAWAVARLSQRFPKAEFAEVSKLVTDLTKVHTECCHGDLL

ECADDRADLAKYICENQDSISSKLKECCEKPLLEKSHCIAEVENDEMPADLPSLAADE

VESKDVCKNYAEAKDVELGMFLYEYARRHPDYSVVLLLRLAKTYETTLEKCCAAADPH

ECYAKVFDEFKPLVEEPQNLIKQNCELFEQLGEYKFQNALLVRYTKKVPQVSTPTLVE

VSRNLGKVGSKCCKHPEAKRMPCAEDYLSVVLNQLCVLHEKTPVSDRVTKCCTESLVN

RRPCFSALEVDETYVPKEFNAETFTFHADICTLSEKERQIKKQTALVELVKHKPKATK

EQLKAVMDDFAAFVEKCCKADDKETCFAEEGKKLVAASQAALGL

Albumin - DNASE1L3 Isoform 2 - Fusion Protein. (Albumin, DNASE1L3 Isoform 2):

SEQ ID NO: 29

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGGSGGSGGSGGSGGSGGSGSSMRICSFNVRSFGESKQEDKNAM

-continued

DVIVKVIKRCDIILVMEIKDSNNRICPILMEKLNREQYAFLYKEKLVSVKRSYHYHDY

QDGDADVFSREPFVVWFQSPHTAVKDFVIIPLHTTPETSVKEIDELVEVYTDVKHRWK

AENFIFMGDFNAGCSYVPKKAWKNIRLRTDPRFVWLIGDQEDTTVKKSTNCAYDRIVL

RGQEIVSSVVPKSNSVFDFQKAYKLTEEEALDVSDHFPVEFKLQSSRAFTNSKKSVTL

RKKTKSKRS

Albumin - DNASE1L3 Isoform 2 Variant - Fusion Protein. (Albumin,
DNASE1L3 Isoform 2 ):

SEQ ID NO: 30

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVELGMELYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGGSGGSGGSGGSGGSGGSGGSGGSGSSMRICSFNVRSFGESKQEDKNAM

DVIVKVIKRCDIILVMEIKDSNNRICPILMEKLNREQYAFLYKEKLVSVKRSYHYHDY

QDGDADVFSREPFVVWFQSPHTAVKDFVIIPLHTTPETSVKEIDELVEVYTDVKHRWK

AENFIFMGDFNAGCSYVPKKAWKNIRLRTDPRFVWLIGDQEDTTVKKSTNCAYDRIVL

RGQEIVSSVVPKSNSVFDFQKAYKLTEEEALDVSDHFPVEFKLQ

LINKER SEQUENCES

SEQ ID NO: 31
GGGGS

SEQ ID NO: 32
GGGGSGGGGSGGGGS

SEQ ID NO: 33
APAPAPAPAPAPAP

SEQ ID NO: 34
AEAAAKEAAAKA

SEQ ID NO: 35
SGGSGSS

SEQ ID NO: 36
SGGSGGSGGSGGSGSS

SEQ ID NO: 37
SGGSGGSGGSGGSGGSGGSGGSGGSGGSGS

SEQ ID NO: 38
GGSGGSGGSGGSGGSGGSGGSGGSGGSGS

OTHER SEQUENCES
Human Serum Albumin (Mature Protein):

SEQ ID NO: 39

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

-continued

AEVENDEMPADLPSLAADFVESKDVCKNYAEAKDVFLGMFLYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGL

Human Factor XI:

SEQ ID NO: 40

MIFLYQVVHFILFTSVSGECVTQLLKDTCFEGGDITTVFTPSAKYCQVVCTYHPRCLL

FTFTAESPSEDPTRWFTCVLKDSVTETLPRVNRTAAISGYSFKQCSHQISACNKDIYV

DLDMKGINYNSSVAKSAQECQERCTDDVHCHFFTYATRQFPSLEHRNICLLKHTQTGT

PTRITKLDKVVSGFSLKSCALSNLACIRDIFPNTVFADSNIDSVMAPDAFVCGRICTH

HPGCLFFTFFSQEWPKESQRNLCLLKTSESGLPSTRIKKSKALSGFSLQSCRHSIPVF

CHSSFYHDTDFLGEELDIVAAKSHEACQKLCTNAVRCQFFTYTPAQASCNEGKGKCYL

KLSSNGSPTKILHGRGGISGYTLRLCKMDNECTTKIKPRIVGGTASVRGEWPWQVTLH

TTSPTQRHLCGGSIIGNQWILTAAHCFYGVESPKILRVYSGILNQSEIKEDTSFFGVQ

EIIIHDQYKMAESGYDIALLKLETTVNYTDSQRPICLPSKGDRNVIYTDCWVTGWGYR

KLRDKIQNTLQKAKIPLVTNEECQKRYRGHKITHKMICAGYREGGKDACKGDSGGPLS

CKHNEVWHLVGITSWGEGCAQRERPGVYTNVVEYVDWILEKTQAV

Human prekallikrein:

SEQ ID NO: 41

MILFKQATYFISLFATVSCGCLTQLYENAFFRGGDVASMYTPNAQYCQMRCTFHPRCL

LESFLPASSINDMEKRFGCFLKDSVTGTLPKVHRTGAVSGHSLKQCGHQISACHRDIY

KGVDMRGVNFNVSKVSSVEECQKRCTNNIRCQFFSYATQTFHKAEYRNNCLLKYSPGG

TPTAIKVLSNVESGFSLKPCALSEIGCHMNIFQHLAFSDVDVARVLTPDAFVCRTICT

YHPNCLFFTFYTNVWKIESQRNVCLLKTSESGTPSSSTPQENTISGYSLLTCKRTLPE

PCHSKIYPGVDFGGEELNVTFVKGVNVCQETCTKMIRCQFFTYSLLPEDCKEEKCKCF

LRLSMDGSPTRIAYGTQGSSGYSLRLCNTGDNSVCTTKTSTRIVGGINSSWGEWPWQV

SLQVKLTAQRHLCGGSLIGHQWVLTAAHCEDGLPLQDVWRIYSGILNLSDITKDTPFS

QIKEIIIHQNYKVSEGNHDIALIKLQAPLNYTEFQKPICLPSKGDTSTIYTNCWVTGW

GFSKEKGEIQNILQKVNIPLVTNEECQKRYQDYKITQRMVCAGYKEGGKDACKGDSGG

PLVCKHNGMWRLVGITSWGEGCARREQPGVYTKVAEYMDWILEKTQSSDGKAQMQSPA

ACTIVATABLE LINKER SEQUENCES
FXIIa-susceptible linker (Factor XI peptide):

SEQ ID NO: 42

CTTKIKPRIVGGTASVRGEWPWQVT

FXIIa-susceptible linker

SEQ ID NO: 43

GGGGSPRIGGGGS

FXIIa-susceptible linker (Prekallikrein peptide):

SEQ ID NO: 44

VCTTKTSTRIVGGTNSSWGEWPWQVS

FXIIa-susceptible linker (Prekallikrein peptide):

SEQ ID NO: 45

STRIVGG

-continued

SIGNAL PEPTIDES
Alpha mating factor (P01149):
                                                                          SEQ ID NO: 46

MRFPSIFTAVLFAASSALAAPVNTTTEDETAQIPAEAVIGYSDLEGDEDVAVLPESNS

TNNGLLFINTTIASIAAKEEGVS

Human Albumin Secretory Signal Peptide + Propeptide (P02768):
                                                                          SEQ ID NO: 47

MKWVTFISLLFLFSSAYSRGVERR

Human DNASE1L3 Signal Peptide (Q13609):
                                                                          SEQ ID NO: 48

MSRELAPLLLLLLSIHSALA

---

What is claimed is:

1. A method for treating a subject for thrombosis, the method comprising administering a therapeutically effective amount of a DNase1-like 3 (D1L3) variant to a subject in need, wherein the D1L3 variant has chromatin-degrading activity and comprises an amino acid sequence that has at least 95% sequence identity to amino acids 21-282 of SEQ ID NO: 4 or amino acids 21 to 252 of SEQ ID NO: 5, wherein the D1L3 variant comprises a substitution at the amino acid corresponding to position 68 of the polypeptide of SEQ ID NO: 4, and wherein the D1L3 variant has a C-terminal deletion of at least 10 consecutive amino acids corresponding to amino acids 296-305 of the polypeptide of SEQ ID NO: 4.

2. The method of claim 1, wherein the D1L3 variant has a C-terminal deletion of at least 20 consecutive amino acids corresponding to amino acids 286-305 of the polypeptide of SEQ ID NO: 4 or amino acids 256-275 of the polypeptide of SEQ ID NO: 5.

3. The method of claim 1, wherein the substitution corresponds to the substitution C68A, C68S, or C68G in the polypeptide of SEQ ID NO: 4.

4. The method of claim 1, wherein the substitution corresponds to the substitution C68A in the polypeptide of SEQ ID NO: 4.

5. The method of claim 1, wherein the D1L3 variant comprises an amino acid sequence that is at least 98% identical to amino acids 21-282 of SEQ ID NO: 4.

6. The method of claim 1, wherein the D1L3 variant is administered parenterally.

7. The method of claim 6, wherein the D1L3 variant is administered intravenously.

8. A method for treating a subject for stroke, the method comprising administering a therapeutically effective amount of a DNase1-like 3 (D1L3) variant to a subject in need, wherein the D1L3 variant has chromatin-degrading activity and comprises an amino acid sequence that has at least 95% sequence identity to amino acids 21-282 of SEQ ID NO: 4 or amino acids 21 to 252 of SEQ ID NO: 5, wherein the D1L3 variant comprises a substitution at the amino acid corresponding to position 68 of the polypeptide of SEQ ID NO: 4, and wherein the D1L3 variant has a C-terminal deletion of at least 10 consecutive amino acids corresponding to amino acids 296-305 of the polypeptide of SEQ ID NO: 4.

9. The method of claim 8, wherein the D1L3 variant has a C-terminal deletion of at least 20 consecutive amino acids corresponding to amino acids 286-305 of the polypeptide of SEQ ID NO: 4 or amino acids 256-275 of the polypeptide of SEQ ID NO: 5.

10. The method of claim 8, wherein the substitution corresponds to the substitution C68A, C68S, or C68G in the polypeptide of SEQ ID NO: 4.

11. The method of claim 8, wherein the substitution corresponds to the substitution C68A in the polypeptide of SEQ ID NO: 4.

12. The method of claim 8, wherein the D1L3 variant comprises an amino acid sequence that is at least 98% identical to amino acids 21-282 of SEQ ID NO: 4.

13. The method of claim 8, wherein the D1L3 variant is administered parenterally.

14. The method of claim 13, wherein the D1L3 variant is administered intravenously.

15. A method for treating a subject for myocardial infarction, the method comprising administering a therapeutically effective amount of a DNase1-like 3 (D1L3) variant to a subject in need,
      wherein the D1L3 variant has chromatin-degrading activity and comprises an amino acid sequence that has at least 95% sequence identity to amino acids 21-282 of SEQ ID NO: 4 or amino acids 21 to 252 of SEQ ID NO: 5, wherein the D1L3 variant comprises a substitution at the amino acid corresponding to position 68 of the polypeptide of SEQ ID NO: 4, and wherein the D1L3 variant has a C-terminal deletion of at least 10 consecutive amino acids corresponding to amino acids 296-305 of the polypeptide of SEQ ID NO: 4.

16. The method of claim 15, wherein the D1L3 variant has a C-terminal deletion of at least 20 consecutive amino acids corresponding to amino acids 286-305 of the polypeptide of SEQ ID NO: 4 or amino acids 256-275 of the polypeptide of SEQ ID NO: 5.

17. The method of claim 15, wherein the substitution corresponds to the substitution C68A, C68S, or C68G in the polypeptide of SEQ ID NO: 4.

18. The method of claim 15, wherein the substitution corresponds to the substitution C68A in the polypeptide of SEQ ID NO: 4.

19. The method of claim 15, wherein the D1L3 variant is administered parenterally.

20. A method for treating a subject for intrabiliary blood clots, the method comprising administering a therapeutically effective amount of a DNase1-like 3 (D1L3) variant to a subject in need,
      wherein the D1L3 variant has chromatin-degrading activity and comprises an amino acid sequence that has at least 95% sequence identity to amino acids 21-282 of SEQ ID NO: 4 or amino acids 21 to 252 of SEQ ID NO: 5, wherein the D1L3 variant comprises a substitution at the amino acid corresponding to position 68 of the polypeptide of SEQ ID NO: 4, and wherein the D1L3 variant has a C-terminal deletion of at least 10 consecutive amino acids corresponding to amino acids 296-305 of the polypeptide of SEQ ID NO: 4.

21. A method for treating a subject having or being at risk for ischemia-reperfusion injury, the method comprising administering a therapeutically effective amount of a DNase1-like 3 (D1L3) variant to a subject in need,
      wherein the D1L3 variant has chromatin-degrading activity and comprises an amino acid sequence that has at least 95% sequence identity to amino acids 21-282 of SEQ ID NO: 4 or amino acids 21 to 252 of SEQ ID NO: 5, wherein the D1L3 variant comprises a substitution at the amino acid corresponding to position 68 of the polypeptide of SEQ ID NO: 4, and wherein the D1L3 variant has a C-terminal deletion of at least 10 consecutive amino acids corresponding to amino acids 296-305 of the polypeptide of SEQ ID NO: 4.

22. The method of claim 21, wherein the D1L3 variant has a C-terminal deletion of at least 20 consecutive amino acids corresponding to amino acids 286-305 of the polypeptide of SEQ ID NO: 4 or amino acids 256-275 of the polypeptide of SEQ ID NO: 5.

23. The method of claim 21, wherein the substitution corresponds to the substitution C68A, C68S, or C68G in the polypeptide of SEQ ID NO: 4.

24. The method of claim 21, wherein the D1L3 variant is administered parenterally.

* * * * *

SEQUENCE LISTING

Sequence total quantity: 48
SEQ ID NO: 1               moltype = AA   length = 282
FEATURE                    Location/Qualifiers
source                     1..282
                           mol_type = protein
                           organism = Homo sapiens
SEQUENCE: 1
MRGMKLLGAL LALAALLQGA VSLKIAAFNI QTFGETKMSN ATLVSYIVQI LSRYDIALVQ    60
EVRDSHLTAV GKLLDNLNQD APDTYHYVVS EPLGRNSYKE RYLFVYRPDQ VSAVDSYYYD   120
DGCEPCGNDT FNREPAIVRF FSRFTEVREF AIVPLHAAPG DAVAEIDALY DVYLDVQEKW   180
GLEDVMLMGD FNAGCSYVRP SQWSSIRLWT SPTFQWLIPD SADTTATPTH CAYDRIVVAG   240
MLLRGAVVPD SALPFNFQAA YGLSDQLAQA ISDHYPVEVM LK                     282

SEQ ID NO: 2               moltype = AA   length = 302
FEATURE                    Location/Qualifiers
source                     1..302
                           mol_type = protein
                           organism = Homo sapiens
SEQUENCE: 2
MHYPTALLFL ILANGAQAFR ICAFNAQRLT LAKVAREQVM DTLVRILARC DIMVLQEVVD    60
SSGSAIPLLL RELNRFDGSG PYSTLSSPQL GRSTYMETYV YFYRSHKTQV LSSYVYNDED   120
DVFAREPFVA QFSLPSNVLP SLVLVPLHTT PKAVEKELNA LYDVFLEVSQ HWQSKDVILL   180
GDFNADCASL TKKRLDKLEL RTEPGFHWVI ADGEDTTVRA STHCTYDRVV LHGERCRSLL   240
HTAAAFDFPT SFQLTEEEAL NISDHYPVEV ELKLSQAHSV QPLSLTVLLL LSLLSPQLCP   300
AA                                                                302

SEQ ID NO: 3               moltype = AA   length = 299
FEATURE                    Location/Qualifiers
source                     1..299
                           mol_type = protein
                           organism = Homo sapiens
SEQUENCE: 3
MGGPRALLAA LWALEAAGTA ALRIGAFNIQ SFGDSKVSDP ACGSIIAKIL AGYDLALVQE    60
VRDPDLSAVS ALMEQINSVS EHEYSFVSSQ PLGRDQYKEM YLFVYRKDAV SVVDTYLYPD   120
PEDVFSREPF VVKFSAPGTG ERAPPLPSRR ALTPPPLPAA AQNLVLIPLH AAPHQAVAEI   180
DALYDVYLDV IDKWGTDDML FLGDFNADCS YVRAQDWAAI RLRSSEVFKW LIPDSADTTV   240
GNSDCAYDRI VACGARLRRS LKPQSATVHD FQEEFGLDQT QALAISDHFP VEVTLKFHR    299

SEQ ID NO: 4               moltype = AA   length = 305
FEATURE                    Location/Qualifiers
source                     1..305
                           mol_type = protein
                           organism = Homo sapiens
SEQUENCE: 4
MSRELAPLLL LLLSIHSALA MRICSFNVRS FGESKQEDKN AMDVIVKVIK RCDIILVMEI    60
KDSNNRICPI LMEKLNRNSR RGITYNYVIS SRLGRNTYKE QYAFLYKEKL VSVKRSYHYH   120
DYQDGDADVF SREPFVVWFQ SPHTAVKDFV IIPLHTTPET SVKEIDELVE VYTDVKHRWK   180
AENFIFMGDF NAGCSYVPKK AWKNIRLRTD PRFVWLIGDQ EDTTVKKSTN CAYDRIVLRG   240
QEIVSSVVPK SNSVFDFQKA YKLTEEEALD VSDHFPVEFK LQSSRAFTNS KKSVTLRKKT   300
KSKRS                                                             305

SEQ ID NO: 5               moltype = AA   length = 275
FEATURE                    Location/Qualifiers
source                     1..275
                           mol_type = protein
                           organism = Homo sapiens
SEQUENCE: 5
MSRELAPLLL LLLSIHSALA MRICSFNVRS FGESKQEDKN AMDVIVKVIK RCDIILVMEI    60
KDSNNRICPI LMEKLNREKL VSVKRSYHYH DYQDGDADVF SREPFVVWFQ SPHTAVKDFV   120

```
IIPLHTTPET SVKEIDELVE VYTDVKHRWK AENFIFMGDF NAGCSYVPKK AWKNIRLRTD    180
PRFVWLIGDQ EDTTVKKSTN CAYDRIVLRG QEIVSSVVPK SNSVFDFQKA YKLTEEEALD    240
VSDHFPVEFK LQSSRAFTNS KKSVTLRKKT KSKRS                               275

SEQ ID NO: 6            moltype = AA  length = 360
FEATURE                 Location/Qualifiers
source                  1..360
                        mol_type = protein
                        organism = Homo sapiens
SEQUENCE: 6
MIPLLLAALL CVPAGALTCY GDSGQPVDWF VVYKLPALRG SGEAAQRGLQ YKYLDESSGG    60
WRDGRALINS PEGAVGRSLQ PLYRSNTSQL AFLLYNDQPP QPSKAQDSSM RGHTKGVLLL    120
DHDGGFWLVH SVPNFPPPAS SAAYSWPHSA CTYGQTLLCV SFPFAQFSKM GKQLTYTYPW    180
VYNYQLEGIF AQEFPDLENV VKGHHVSQEP WNSSITLTSQ AGAVFQSFAK FSKFGDDLYS    240
GWLAAALGTN LQVQFWHKTV GILPSNCSDI WQVLNVNQIA FPGPAGPSFN STEDHSKWCV    300
SPKGPWTCVG DMNRNQGEEQ RGGGTLCAQL PALWKAFQPL VKNYQPCNGM ARKPSRAYKI    360

SEQ ID NO: 7            moltype = AA  length = 361
FEATURE                 Location/Qualifiers
source                  1..361
                        mol_type = protein
                        organism = Homo sapiens
SEQUENCE: 7
MKQKMMARLL RTSFALLFLG LFGVLGAATI SCRNEEGKAV DWFTFYKLPK RQNKESGETG    60
LEYLYLDSTT RSWRKSEQLM NDTKSVLGRT LQQLYEAYAS KSNNTAYLIY NDGVPKPVNY    120
SRKYGHTKGL LLWNRVQGFW LIHSIPQFPP IPEEGYDYPP TGRRNGQSGI CITFKYNQYE    180
AIDSQLLVCN PNVYSCSIPA TFHQELIHMP QLCTRASSSE IPGRLLTTLQ SAQGQKFLHF    240
AKSDSFLDDI FAAWMAQRLK THLLTETWQR KRQELPSNCS LPYHVYNIKA IKLSRHSYFS    300
SYQDHAKWCI SQKGTKNRWT CIGDLNRSPH QAFRSGGFIC TQNWQIYQAF QGLVLYYESC    360
K                                                                    361

SEQ ID NO: 8            moltype = AA  length = 305
FEATURE                 Location/Qualifiers
source                  1..305
                        mol_type = protein
                        organism = Homo sapiens
SEQUENCE: 8
MSRELAPLLL LLLSIHSALA MRICSFNVRS FGESKQEDKN AMDVIVKVIK RCDIILVMEI    60
KDSNNRICPI LMEKLNRNSR RGITYNYVIS SRLGRNTYKE RYAFLYKEKL VSVKRSYHYH    120
DYQDGDADVF SREPFVVWFQ SPHTAVKDFV IIPLHTTPET SVKEIDELVE VYTDVKHRWK    180
AENFIFMGDF NAGCSYVPKK AWKNIRLRTD PRFVWLIGDQ EDTTVKKSTN CAYDRIVLRG    240
QEIVSSVVPK SNSVFDFQKA YKLTEEEALD VSDHFPVEFK LQSSRAFTNS KKSVTLRKKT    300
KSKRS                                                                305

SEQ ID NO: 9            moltype = AA  length = 282
FEATURE                 Location/Qualifiers
source                  1..282
                        mol_type = protein
                        organism = Homo sapiens
SEQUENCE: 9
MSRELAPLLL LLLSIHSALA MRICSFNVRS FGESKQEDKN AMDVIVKVIK RCDIILVMEI    60
KDSNNRICPI LMEKLNRNSR RGITYNYVIS SRLGRNTYKE QYAFLYKEKL VSVKRSYHYH    120
DYQDGDADVF SREPFVVWFQ SPHTAVKDFV IIPLHTTPET SVKEIDELVE VYTDVKHRWK    180
AENFIFMGDF NAGCSYVPKK AWKNIRLRTD PRFVWLIGDQ EDTTVKKSTN CAYDRIVLRG    240
QEIVSSVVPK SNSVFDFQKA YKLTEEEALD VSDHFPVEFK LK                       282

SEQ ID NO: 10           moltype = AA  length = 290
FEATURE                 Location/Qualifiers
source                  1..290
                        mol_type = protein
                        organism = Homo sapiens
SEQUENCE: 10
MSRELAPLLL LLLSIHSALA MRICSFNVRS FGESKQEDKN AMDVIVKVIK RCDIILVMEI    60
KDSNNRICPI LMEKLNRNSR RGITYNYVIS SRLGRNTYKE QYAFLYKEKL VSVKRSYHYH    120
DYQDGDADVF SREPFVVWFQ SPHTAVKDFV IIPLHTTPET SVKEIDELVE VYTDVKHRWG    180
LENFIFMGDF NAGCSYVRPS QWKNIRLRTD PRFVWLIGDQ EDTTVKKSTN CAYDRIVLRG    240
QEIVSSVVPK SNSVFDFQAA YKLTEEEALD VSDHFPVEFK LQSSRAFTNS               290

SEQ ID NO: 11           moltype = AA  length = 291
FEATURE                 Location/Qualifiers
source                  1..291
                        mol_type = protein
                        organism = Homo sapiens
SEQUENCE: 11
MSRELAPLLL LLLSIHSALA MRICSFNVRS FGESKQEDKN AMDVIVKVIK RCDIILVMEI    60
KDSNNRICPI LMEKLNRNSR RGITYNYVIS SRLGRNTYKE QYAFLYKEKL VSVKRSYHYH    120
DYQDGDADVF SREPFVVWFQ SPHTAVKDFV IIPLHTTPET SVKEIDELVE VYTDVKHRWG    180
LENFIFMGDF NAGCSYVRPS QWKNIRLRTD PRFVWLIGDQ EDTTVKKSTN CAYDRIVLRG    240
QEIVSSVVPK SNSVFDFQAA YKLTEEEALD VSDHFPVEFK LQSSRAFTNS K             291
```

-continued

```
SEQ ID NO: 12                   moltype = AA  length = 292
FEATURE                         Location/Qualifiers
source                          1..292
                                mol_type = protein
                                organism = Homo sapiens
SEQUENCE: 12
MSRELAPLLL LLLSIHSALA MRICSFNVRS FGESKQEDKN AMDVIVKVIK RCDIILVMEI    60
KDSNNRICPI LMEKLNRNSR RGITYNYVIS SRLGRNTYKE QYAFLYKEKL VSVKRSYHYH   120
DYQDGDADVF SREPFVVWFQ SPHTAVKDFV IIPLHTTPET SVKEIDELVE VYTDVKHRWG   180
LENFIFMGDF NAGCSYVRPS QWKNIRLRTD PRFVWLIGDQ EDTTVKKSTN CAYDRIVLRG   240
QEIVSSVVPK SNSVFDFQAA YKLTEEEALD VSDHFPVEFK LQSSRAFTNS KK           292

SEQ ID NO: 13                   moltype = AA  length = 305
FEATURE                         Location/Qualifiers
source                          1..305
                                mol_type = protein
                                organism = Homo sapiens
SEQUENCE: 13
MSRELAPLLL LLLSIHSALA MRICSFNVRS FGESKQEDKN AMDVIVKVIK RCDIILVMEI    60
KDSNNRIAPI LMEKLNRNSR RGITYNYVIS SRLGRNTYKE QYAFLYKEKL VSVKRSYHYH   120
DYQDGDADVF SREPFVVWFQ SPHTAVKDFV IIPLHTTPET SVKEIDELVE VYTDVKHRWK   180
AENFIFMGDF NAGCSYVPKK AWKNIRLRTD PRFVWLIGDQ EDTTVKKSTN CAYDRIVLRG   240
QEIVSSVVPK SNSVFDFQKA YKLTEEEALD VSDHFPVEFK LQSSRAFTNS KKSVTLRKKT   300
KSKRS                                                               305

SEQ ID NO: 14                   moltype = AA  length = 282
FEATURE                         Location/Qualifiers
source                          1..282
                                mol_type = protein
                                organism = Homo sapiens
SEQUENCE: 14
MSRELAPLLL LLLSIHSALA MRICSFNVRS FGESKQEDKN AMDVIVKVIK RCDIILVMEI    60
KDSNNRICPI LMEKLNRNSR RGITYNYVIS SRLGRNTYKE QYAFLYKEKL VSVKRSYHYH   120
DYQDGDADVF SREPFVVWFQ SPHTAVKDFV IIPLHTTPET SVKEIDELVE VYTDVKHRWK   180
AENFIFMGDF NAGCSYVPKK AWKNIRLRTD PRFVWLIGDQ EDTTVKKSTN CAYDRIVLRG   240
QEIVSSVVPK SNSVFDFQKA YKLTEEEALD VSDHYPVEVM LK                      282

SEQ ID NO: 15                   moltype = AA  length = 282
FEATURE                         Location/Qualifiers
source                          1..282
                                mol_type = protein
                                organism = Homo sapiens
SEQUENCE: 15
MSRELAPLLL LLLSIHSALA MRICSFNVRS FGESKQEDKN AMDVIVKVIK RCDIILVMEI    60
KDSNNRICPI LMEKLNRNSR RGITYNYVIS SRLGRNTYKE QYAFLYKEKL VSVKRSYHYH   120
DYQDGDADVF SREPFVVWFQ SPHTAVKDFV IIPLHTTPET SVKEIDELVE VYTDVKHRWK   180
AENFIFMGDF NAGCSYVPKK AWKNIRLRTD PRFVWLIGDQ EDTTVKKSTN CAYDRIVLRG   240
QEIVSSVVPK SNSVFDFQKA YKLTEEEALD VSDHFPVEFK LQ                      282

SEQ ID NO: 16                   moltype = AA  length = 254
FEATURE                         Location/Qualifiers
source                          1..254
                                mol_type = protein
                                organism = Homo sapiens
SEQUENCE: 16
MSRELAPLLL LLLSIHSALA MRICSFNVRS FGESKQEDKN AMDVIVKVIK RCDIILVMEI    60
KDSNNRICPI LMEKLNREKL VSVKRSYHYH DYQDGDADVF SREPFVVWFQ SPHTAVKDFV   120
IIPLHTTPET SVKEIDELVE VYTDVKHRWK AENFIFMGDF NAGCSYVPKK AWKNIRLRTD   180
PRFVWLIGDQ EDTTVKKSTN CAYDRIVLRG QEIVSSVVPK SNSVFDFQKA YKLTEEEALD   240
VSDHFPVEFK LQSS                                                     254

SEQ ID NO: 17                   moltype = AA  length = 847
FEATURE                         Location/Qualifiers
REGION                          1..847
                                note = Synthetic Sequence
source                          1..847
                                mol_type = protein
                                organism = synthetic construct
SEQUENCE: 17
DAHKSEVAHR FKDLGEENFK ALVLIAFAQY LQQCPFEDHV KLVNEVTEFA KTCVADESAE    60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
LVNRRPCFSA LEVDETYVPK EFNAETFTFH ADICTLSEKE RQIKKQTALV ELVKHKPKAT   540
```

-continued

```
KEQLKAVMDD FAAFVEKCCK ADDKETCFAE EGKKLVAASQ AALGLMRICS FNVRSFGESK   600
QEDKNAMDVI VKVIKRCDII LVMEIKDSNN RICPILMEKL NRNSRRGITY NYVISSRLGR   660
NTYKEQYAFL YKEKLVSVKR SYHYHDYQDG DADVFSREPF VVWFQSPHTA VKDFVIIPLH   720
TTPETSVKEI DELVEVYTDV KHRWKAENFI FMGDFNAGCS YVPKKAWKNI RLRTDPRFVW   780
LIGDQEDTTV KKSTNCAYDR IVLRGQEIVS SVVPKSNSVF DFQKAYKLTE EEALDVSDHY   840
PVEVMLK                                                            847

SEQ ID NO: 18            moltype = AA  length = 852
FEATURE                  Location/Qualifiers
REGION                   1..852
                         note = Synthetic Sequence
source                   1..852
                         mol_type = protein
                         organism = synthetic construct
SEQUENCE: 18
DAHKSEVAHR FKDLGEENFK ALVLIAFAQY LQQCPFEDHV KLVNEVTEFA KTCVADESAE   60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
LVNRRPCFSA LEVDETYVPK EFNAETFTFH ADICTLSEKE RQIKKQTALV ELVKHKPKAT   540
KEQLKAVMDD FAAFVEKCCK ADDKETCFAE EGKKLVAASQ AALGLGGGGS MRICSFNVRS   600
FGESKQEDKN AMDVIVKVIK RCDIILVMEI KDSNNRICPI LMEKLNRNSR RGITYNYVIS   660
SRLGRNTYKE QYAFLYKEKL VSVKRSYHYH DYQDGDADVF SREPFVVWFQ SPHTAVKDFV   720
IIPLHTTPET SVKEIDELVE VYTDVKHRWK AENFIFMGDF NAGCSYVPKK AWKNIRLRTD   780
PRFVWLIGDQ EDTTVKKSTN CAYDRIVLRG QEIVSSVVPK SNSVFDFQKA YKLTEEEALD   840
VSDHYPVEVM LK                                                      852

SEQ ID NO: 19            moltype = AA  length = 862
FEATURE                  Location/Qualifiers
REGION                   1..862
                         note = Synthetic Sequence
source                   1..862
                         mol_type = protein
                         organism = synthetic construct
SEQUENCE: 19
DAHKSEVAHR FKDLGEENFK ALVLIAFAQY LQQCPFEDHV KLVNEVTEFA KTCVADESAE   60
NCDKSLHTLF GDKLCTVATL RETYGEMADC CAKQEPERNE CFLQHKDDNP NLPRLVRPEV   120
DVMCTAFHDN EETFLKKYLY EIARRHPYFY APELLFFAKR YKAAFTECCQ AADKAACLLP   180
KLDELRDEGK ASSAKQRLKC ASLQKFGERA FKAWAVARLS QRFPKAEFAE VSKLVTDLTK   240
VHTECCHGDL LECADDRADL AKYICENQDS ISSKLKECCE KPLLEKSHCI AEVENDEMPA   300
DLPSLAADFV ESKDVCKNYA EAKDVFLGMF LYEYARRHPD YSVVLLLRLA KTYETTLEKC   360
CAAADPHECY AKVFDEFKPL VEEPQNLIKQ NCELFEQLGE YKFQNALLVR YTKKVPQVST   420
PTLVEVSRNL GKVGSKCCKH PEAKRMPCAE DYLSVVLNQL CVLHEKTPVS DRVTKCCTES   480
LVNRRPCFSA LEVDETYVPK EFNAETFTFH ADICTLSEKE RQIKKQTALV ELVKHKPKAT   540
KEQLKAVMDD FAAFVEKCCK ADDKETCFAE EGKKLVAASQ AALGLGGGGS GGGGSGGGGS   600
MRICSFNVRS FGESKQEDKN AMDVIVKVIK RCDIILVMEI KDSNNRICPI LMEKLNRNSR   660
RGITYNYVIS SRLGRNTYKE QYAFLYKEKL VSVKRSYHYH DYQDGDADVF SREPFVVWFQ   720
SPHTAVKDFV IIPLHTTPET SVKEIDELVE VYTDVKHRWK AENFIFMGDF NAGCSYVPKK   780
AWKNIRLRTD PRFVWLIGDQ EDTTVKKSTN CAYDRIVLRG QEIVSSVVPK SNSVFDFQKA   840
YKLTEEEALD VSDHYPVEVM LK                                            862

SEQ ID NO: 20            moltype = AA  length = 852
FEATURE                  Location/Qualifiers
REGION                   1..852
                         note = Synthetic Sequence
source                   1..852
                         mol_type = protein
                         organism = synthetic construct
SEQUENCE: 20
MRICSFNVRS FGESKQEDKN AMDVIVKVIK RCDIILVMEI KDSNNRICPI LMEKLNRNSR   60
RGITYNYVIS SRLGRNTYKE QYAFLYKEKL VSVKRSYHYH DYQDGDADVF SREPFVVWFQ   120
SPHTAVKDFV IIPLHTTPET SVKEIDELVE VYTDVKHRWK AENFIFMGDF NAGCSYVPKK   180
AWKNIRLRTD PRFVWLIGDQ EDTTVKKSTN CAYDRIVLRG QEIVSSVVPK SNSVFDFQKA   240
YKLTEEEALD VSDHYPVEVM LKGGGGSDAH KSEVAHRFKD LGEENFKALV LIAFAQYLQQ   300
CPFEDHVKLV NEVTEFAKTC VADESAENCD KSLHTLFGDK LCTVATLRET YGEMADCCAK   360
QEPERNECFL QHKDDNPNLP RLVRPEVDVM CTAFHDNEET FLKKYLYEIA RRHPYFYAPE   420
LLFFAKRYKA AFTECCQAAD KAACLLPKLD ELRDEGKASS AKQRLKCASL QKFGERAFKA   480
WAVARLSQRF PKAEFAEVSK LVTDLTKVHT ECCHGDLLEC ADDRADLAKY ICENQDSISS   540
KLKECCEKPL LEKSHCIAEV ENDEMPADLP SLAADFVESK DVCKNYAEAK DVFLGMFLYE   600
YARRHPDYSV VLLLRLAKTY ETTLEKCCAA ADPHECYAKV FDEFKPLVEE PQNLIKQNCE   660
LFEQLGEYKF QNALLVRYTK KVPQVSTPTL VEVSRNLGKV GSKCCKHPEA KRMPCAEDYL   720
SVVLNQLCVL HEKTPVSDRV TKCCTESLVN RRPCFSALEV DETYVPKEFN AETFTFHADI   780
CTLSEKERQI KKQTALVELV KHKPKATKEQ LKAVMDDFAA FVEKCCKADD KETCFAEEGK   840
KLVAASQAAL GL                                                      852
```

```
SEQ ID NO: 21              moltype = AA   length = 862
FEATURE                    Location/Qualifiers
REGION                     1..862
                           note = Synthetic Sequence
source                     1..862
                           mol_type = protein
                           organism = synthetic construct
SEQUENCE: 21
MRICSFNVRS FGESKQEDKN AMDVIVKVIK RCDIILVMEI KDSNNRICPI LMEKLNRNSR  60
RGITYNYVIS SRLGRNTYKE QYAFLYKEKL VSVKRSYHYH DYQDGDADVF SREPFVVWFQ  120
SPHTAVKDFV IIPLHTTPET SVKEIDELVE VYTDVKHRWK AENFIFMGDF NAGCSYVPKK  180
AWKNIRLRTD PRFVWLIGDQ EDTTVKKSTN CAYDRIVLRG QEIVSSVVPK SNSVFDFQKA  240
YKLTEEEALD VSDHYPVEVM LKGGGGSGGG GSGGGGSDAH KSEVAHRFKD LGEENFKALV  300
LIAFAQYLQQ CPFEDHVKLV NEVTEFAKTC VADESAENCD KSLHTLFGDK LCTVATLRET  360
YGEMADCCAK QEPERNECFL QHKDDNPNLP RLVRPEVDVM CTAFHDNEET FLKKYLYEIA  420
RRHPYFYAPE LLFFAKRYKA AFTECCQAAD KAACLLPKLD ELRDEGKASS AKQRLKCASL  480
QKFGERAFKA WAVARLSQRF PKAEFAEVSK LVTDLTKVHT ECCHGDLLEC ADDRADLAKY  540
ICENQDSISS KLKECCEKPL LEKSHCIAEV ENDMPADLP SLAADFVESK DVCKNYAEAK  600
DVFLGMFLYE YARRHPDYSV VLLLRLAKTY ETTLEKCCAA ADPHECYAKV FDEFKPLVEE  660
PQNLIKQNCE LFEQLGEYKF QNALLVRYTK KVPQVSTPTL VEVSRNLGKV GSKCCKHPEA  720
KRMPCAEDYL SVVLNQLCVL HEKTPVSDRV TKCCTESLVN RRPCFSALEV DETYVPKEFN  780
AETFTFHADI CTLSEKERQI KKQTALVELV KHKPKATKEQ LKAVMDDFAA FVEKCCKADD  840
KETCFAEEGK KLVAASQAAL GL                                          862

SEQ ID NO: 22              moltype = AA   length = 885
FEATURE                    Location/Qualifiers
REGION                     1..885
                           note = Synthetic Sequence
source                     1..885
                           mol_type = protein
                           organism = synthetic construct
SEQUENCE: 22
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGLGGGGS GGGGSGGGGS  600
MRICSFNVRS FGESKQEDKN AMDVIVKVIK RCDIILVMEI KDSNNRICPI LMEKLNRNSR  660
RGITYNYVIS SRLGRNTYKE QYAFLYKEKL VSVKRSYHYH DYQDGDADVF SREPFVVWFQ  720
SPHTAVKDFV IIPLHTTPET SVKEIDELVE VYTDVKHRWK AENFIFMGDF NAGCSYVPKK  780
AWKNIRLRTD PRFVWLIGDQ EDTTVKKSTN CAYDRIVLRG QEIVSSVVPK SNSVFDFQKA  840
YKLTEEEALD VSDHFPVEFK LQSSRAFTNS KKSVTLRKKT KSKRS                 885

SEQ ID NO: 23              moltype = AA   length = 884
FEATURE                    Location/Qualifiers
REGION                     1..884
                           note = Synthetic Sequence
source                     1..884
                           mol_type = protein
                           organism = synthetic construct
SEQUENCE: 23
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGLAPAPA PAPAPAPAPM  600
RICSFNVRSF GESKQEDKNA MDVIVKVIKR CDIILVMEIK DSNNRICPIL MEKLNRNSRR  660
GITYNYVISS RLGRNTYKEQ YAFLYKEKLV SVKRSYHYD YQDGDADVFS REPFVVWFQS  720
PHTAVKDFVI IPLHTTPETS VKEIDELVEV YTDVKHRWKA ENFIFMGDFN AGCSYVPKKA  780
WKNIRLRTDP RFVWLIGDQE DTTVKKSTNC AYDRIVLRGQ EIVSSVVPKS NSVFDFQKAY  840
KLTEEEALDV SDHFPVEFKL QSSRAFTNSK KSVTLRKKTK SKRS                  884

SEQ ID NO: 24              moltype = AA   length = 882
FEATURE                    Location/Qualifiers
REGION                     1..882
                           note = Synthetic Sequence
source                     1..882
                           mol_type = protein
                           organism = synthetic construct
```

-continued

```
SEQUENCE: 24
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGLAEAAA KEAAAKAMRI  600
CSFNVRSFGE SKQEDKNAMD VIVKVIKRCD IILVMEIKDS NNRICPILME KLNRNSRRGI  660
TYNYVISSRL GRNTYKEQYA FLYKEKLVSV KRSYHYHDYQ DGDADVFSRE PFVVWFQSPH  720
TAVKDFVIIP LHTTPETSVK EIDELVEVYT DVKHRWKAEN FIFMGDFNAG CSYVPKKAWK  780
NIRLRTDPRF VWLIGDQEDT TVKKSTNCAY DRIVLRGQEI VSSVVPKSNS VFDFQKAYKL  840
TEEEALDVSD HFPVEFKLQS SRAFTNSKKS VTLRKKTKSK RS                     882

SEQ ID NO: 25            moltype = AA  length = 854
FEATURE                  Location/Qualifiers
REGION                   1..854
                         note = Synthetic Sequence
source                   1..854
                         mol_type = protein
                         organism = synthetic construct
SEQUENCE: 25
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGLSGGSG SSMRICSFNV  600
RSFGESKQED KNAMDVIVKV IKRCDIILVM EIKDSNNRIC PILMEKLNRN SRRGITYNYV  660
ISSRLGRNTY KEQYAFLYKE KLVSVKRSYH YHDYQDGDAD VFSREPFVVW FQSPHTAVKD  720
FVIIPLHTTP ETSVKEIDEL VEVYTDVKHR WKAENFIFMG DFNAGCSYVP KKAWKNIRLR  780
TDPRFVWLIG DQEDTTVKKS TNCAYDRIVL RGQEIVSSVV PKSNSVFDFQ KAYKLTEEEA  840
LDVSDHFPVE FKLQ                                                    854

SEQ ID NO: 26            moltype = AA  length = 863
FEATURE                  Location/Qualifiers
REGION                   1..863
                         note = Synthetic Sequence
source                   1..863
                         mol_type = protein
                         organism = synthetic construct
SEQUENCE: 26
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGLSGGSG GSGGSGGSGS  600
SMRICSFNVR SFGESKQEDK NAMDVIVKVI KRCDIILVME IKDSNNRICP ILMEKLNRNS  660
RRGITYNYVI SSRLGRNTYK EQYAFLYKEK LVSVKRSYHY HDYQDGDADV FSREPFVVWF  720
QSPHTAVKDF VIIPLHTTPE TSVKEIDELV EVYTDVKHRW KAENFIFMGD FNAGCSYVPK  780
KAWKNIRLRT DPRFVWLIGD QEDTTVKKST NCAYDRIVLR GQEIVSSVVP KSNSVFDFQK  840
AYKLTEEEAL DVSDHFPVEF KLQ                                          863

SEQ ID NO: 27            moltype = AA  length = 878
FEATURE                  Location/Qualifiers
REGION                   1..878
                         note = Synthetic Sequence
source                   1..878
                         mol_type = protein
                         organism = synthetic construct
SEQUENCE: 27
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
```

```
CAAADPHECY AKVFDEFKPL VEEPQNLIKQ NCELFEQLGE YKFQNALLVR YTKKVPQVST     420
PTLVEVSRNL GKVGSKCCKH PEAKRMPCAE DYLSVVLNQL CVLHEKTPVS DRVTKCCTES     480
LVNRRPCFSA LEVDETYVPK EFNAETFTFH ADICTLSEKE RQIKKQTALV ELVKHKPKAT     540
KEQLKAVMDD FAAFVEKCCK ADDKETCFAE EGKKLVAASQ AALGLSGGSG GSGGSGGSGG     600
SGGSGGSGGS GGSGSSMRIC SFNVRSFGES KQEDKNAMDV IVKVIKRCDI ILVMEIKDSN     660
NRICPILMEK LNRNSRRGIT YNYVISSRLG RNTYKEQYAF LYKEKLVSVK RSYHYHDYQD     720
GDADVFSREP FVVWFQSPHT AVKDFVIIPL HTTPETSVKE IDELVEVYTD VKHRWKAENF     780
IFMGDFNAGC SYVPKKAWKN IRLRTDPRFV WLIGDQEDTT VKKSTNCAYD RIVLRGQEIV     840
SSVVPKSNSV FDFQKAYKLT EEEALDVSDH FPVEFKLQ                            878

SEQ ID NO: 28          moltype = AA  length = 1494
FEATURE                Location/Qualifiers
REGION                 1..1494
                       note = Synthetic Sequence
source                 1..1494
                       mol_type = protein
                       organism = synthetic construct
SEQUENCE: 28
DAHKSEVAHR FKDLGEENFK ALVLIAFAQY LQQCPFEDHV KLVNEVTEFA KTCVADESAE      60
NCDKSLHTLF GDKLCTVATL RETYGEMADC CAKQEPERNE CFLQHKDDNP NLPRLVRPEV     120
DVMCTAFHDN EETFLKKYLY EIARRHPYFY APELLFFAKR YKAAFTECCQ AADKAACLLP     180
KLDELRDEGK ASSAKQRLKC ASLQKFGERA FKAWAVARLS QRFPKAEFAE VSKLVTDLTK     240
VHTECCHGDL LECADDRADL AKYICENQDS ISSKLKECCE KPLLEKSHCI AEVENDEMPA     300
DLPSLAADFV ESKDVCKNYA EAKDVFLGMF LYEYARRHPD YSVVLLLRLA KTYETTLEKC     360
CAAADPHECY AKVFDEFKPL VEEPQNLIKQ NCELFEQLGE YKFQNALLVR YTKKVPQVST     420
PTLVEVSRNL GKVGSKCCKH PEAKRMPCAE DYLSVVLNQL CVLHEKTPVS DRVTKCCTES     480
LVNRRPCFSA LEVDETYVPK EFNAETFTFH ADICTLSEKE RQIKKQTALV ELVKHKPKAT     540
KEQLKAVMDD FAAFVEKCCK ADDKETCFAE EGKKLVAASQ AALGLSGGSG GSGGSGGSGG     600
SGGSGGSGGS GGSGSSMRIC SFNVRSFGES KQEDKNAMDV IVKVIKRCDI ILVMEIKDSN     660
NRICPILMEK LNRNSRRGIT YNYVISSRLG RNTYKEQYAF LYKEKLVSVK RSYHYHDYQD     720
GDADVFSREP FVVWFQSPHT AVKDFVIIPL HTTPETSVKE IDELVEVYTD VKHRWKAENF     780
IFMGDFNAGC SYVPKKAWKN IRLRTDPRFV WLIGDQEDTT VKKSTNCAYD RIVLRGQEIV     840
SSVVPKSNSV FDFQKAYKLT EEEALDVSDH FPVEFKLQSS GGSGGSGGSG GSGGSGGSGG     900
SGGSGGSGSD AHKSEVAHRF KDLGEENFKA LVLIAFAQYL QQCPFEDHVK LVNEVTEFAK     960
TCVADESAEN CDKSLHTLFG DKLCTVATLR ETYGEMADCC AKQEPERNEC FLQHKDDNPN    1020
LPRLVRPEVD VMCTAFHDNE ETFLKKYLYE IARRHPYFYA PELLFFAKRY KAAFTECCQA    1080
ADKAACLLPK LDELRDEGKA SSAKQRLKCA SLQKFGERAF KAWAVARLSQ RFPKAEFAEV    1140
SKLVTDLTKV HTECCHGDLL ECADDRADLA KYICENQDSI SSKLKECCEK PLLEKSHCIA    1200
EVENDEMPAD LPSLAADFVE SKDVCKNYAE AKDVFLGMFL YEYARRHPDY SVVLLLRLAK    1260
TYETTLEKCC AAADPHECYA KVFDEFKPLV EEPQNLIKQN CELFEQLGEY KFQNALLVRY    1320
TKKVPQVSTP TLVEVSRNLG KVGSKCCKHP EAKRMPCAED YLSVVLNQLC VLHEKTPVSD    1380
RVTKCCTESL VNRRPCFSAL EVDETYVPKE FNAETFTFHA DICTLSEKER QIKKQTALVE    1440
LVKHKPKATK EQLKAVMDDF AAFVEKCCKA DDKETCFAEE GKKLVAASQA ALGL          1494

SEQ ID NO: 29          moltype = AA  length = 879
FEATURE                Location/Qualifiers
REGION                 1..879
                       note = Synthetic Sequence
source                 1..879
                       mol_type = protein
                       organism = synthetic construct
SEQUENCE: 29
DAHKSEVAHR FKDLGEENFK ALVLIAFAQY LQQCPFEDHV KLVNEVTEFA KTCVADESAE      60
NCDKSLHTLF GDKLCTVATL RETYGEMADC CAKQEPERNE CFLQHKDDNP NLPRLVRPEV     120
DVMCTAFHDN EETFLKKYLY EIARRHPYFY APELLFFAKR YKAAFTECCQ AADKAACLLP     180
KLDELRDEGK ASSAKQRLKC ASLQKFGERA FKAWAVARLS QRFPKAEFAE VSKLVTDLTK     240
VHTECCHGDL LECADDRADL AKYICENQDS ISSKLKECCE KPLLEKSHCI AEVENDEMPA     300
DLPSLAADFV ESKDVCKNYA EAKDVFLGMF LYEYARRHPD YSVVLLLRLA KTYETTLEKC     360
CAAADPHECY AKVFDEFKPL VEEPQNLIKQ NCELFEQLGE YKFQNALLVR YTKKVPQVST     420
PTLVEVSRNL GKVGSKCCKH PEAKRMPCAE DYLSVVLNQL CVLHEKTPVS DRVTKCCTES     480
LVNRRPCFSA LEVDETYVPK EFNAETFTFH ADICTLSEKE RQIKKQTALV ELVKHKPKAT     540
KEQLKAVMDD FAAFVEKCCK ADDKETCFAE EGKKLVAASQ AALGLSGGSG GSGGSGGSGG     600
SGGSGGSGGS GGSGSSMRIC SFNVRSFGES KQEDKNAMDV IVKVIKRCDI ILVMEIKDSN     660
NRICPILMEK LNREQYAFLY KEKLVSVKRS YHYHDYQDGD ADVFSREPFV VWFQSPHTAV     720
KDFVIIPLHT TPETSVKEID ELVEVYTDVK HRWKAENFIF MGDFNAGCSY VPKKAWKNIR     780
LRTDPRFVWL IGDQEDTTVK KSTNCAYDRI VLRGQEIVSS VVPKSNSVFD FQKAYKLTEE     840
EALDVSDHFP VEFKLQSSRA FTNSKKSVTL RKKTKSKRS                            879

SEQ ID NO: 30          moltype = AA  length = 856
FEATURE                Location/Qualifiers
REGION                 1..856
                       note = Synthetic Sequence
source                 1..856
                       mol_type = protein
                       organism = synthetic construct
SEQUENCE: 30
DAHKSEVAHR FKDLGEENFK ALVLIAFAQY LQQCPFEDHV KLVNEVTEFA KTCVADESAE      60
NCDKSLHTLF GDKLCTVATL RETYGEMADC CAKQEPERNE CFLQHKDDNP NLPRLVRPEV     120
DVMCTAFHDN EETFLKKYLY EIARRHPYFY APELLFFAKR YKAAFTECCQ AADKAACLLP     180
```

```
KLDELRDEGK ASSAKQRLKC ASLQKFGERA FKAWAVARLS QRFPKAEFAE VSKLVTDLTK    240
VHTECCHGDL LECADDRADL AKYICENQDS ISSKLKECCE KPLLEKSHCI AEVENDEMPA    300
DLPSLAADFV ESKDVCKNYA EAKDVFLGMF LYEYARRHPD YSVVLLLRLA KTYETTLEKC    360
CAAADPHECY AKVFDEFKPL VEEPQNLIKQ NCELFEQLGE YKFQNALLVR YTKKVPQVST    420
PTLVEVSRNL GKVGSKCCKH PEAKRMPCAE DYLSVVLNQL CVLHEKTPVS DRVTKCCTES    480
LVNRRPCFSA LEVDETYVPK EFNAETFTFH ADICTLSEKE RQIKKQTALV ELVKHKPKAT    540
KEQLKAVMDD FAAFVEKCCK ADDKETCFAE EGKKLVAASQ AALGLSGGSG GSGGSGGSGG    600
SGGSGGSGGS GGSGSSMRIC SFNVRSFGES KQEDKNAMDV IVKVIKRCDI ILVMEIKDSN    660
NRICPILMEK LNREQYAFLY KEKLVSVKRS YHYHDYQDGD ADVFSREPFV VWFQSPHTAV    720
KDFVIIPLHT TPETSVKEID ELVEVYTDVK HRWKAENFIF MGDFNAGCSY VPKKAWKNIR    780
LRTDPRFVWL IGDQEDTTVK KSTNCAYDRI VLRGQEIVSS VVPKSNSVFD FQKAYKLTEE    840
EALDVSDHFP VEFKLQ                                                    856

SEQ ID NO: 31              moltype = AA   length = 5
FEATURE                    Location/Qualifiers
REGION                     1..5
                           note = Synthetic Sequence
source                     1..5
                           mol_type = protein
                           organism = synthetic construct
SEQUENCE: 31
GGGGS                                                                  5

SEQ ID NO: 32              moltype = AA   length = 15
FEATURE                    Location/Qualifiers
REGION                     1..15
                           note = Synthetic Sequence
source                     1..15
                           mol_type = protein
                           organism = synthetic construct
SEQUENCE: 32
GGGGSGGGGS GGGGS                                                      15

SEQ ID NO: 33              moltype = AA   length = 14
FEATURE                    Location/Qualifiers
REGION                     1..14
                           note = Synthetic Sequence
source                     1..14
                           mol_type = protein
                           organism = synthetic construct
SEQUENCE: 33
APAPAPAPAP APAP                                                       14

SEQ ID NO: 34              moltype = AA   length = 12
FEATURE                    Location/Qualifiers
REGION                     1..12
                           note = Synthetic Sequence
source                     1..12
                           mol_type = protein
                           organism = synthetic construct
SEQUENCE: 34
AEAAAKEAAA KA                                                         12

SEQ ID NO: 35              moltype = AA   length = 7
FEATURE                    Location/Qualifiers
REGION                     1..7
                           note = Synthetic Sequence
source                     1..7
                           mol_type = protein
                           organism = synthetic construct
SEQUENCE: 35
SGGSGSS                                                                7

SEQ ID NO: 36              moltype = AA   length = 16
FEATURE                    Location/Qualifiers
REGION                     1..16
                           note = Synthetic Sequence
source                     1..16
                           mol_type = protein
                           organism = synthetic construct
SEQUENCE: 36
SGGSGGSGGS GGSGSS                                                     16

SEQ ID NO: 37              moltype = AA   length = 31
FEATURE                    Location/Qualifiers
REGION                     1..31
                           note = Synthetic Sequence
source                     1..31
                           mol_type = protein
```

-continued

```
                         organism = synthetic construct
SEQUENCE: 37
SGGSGGSGGS GGSGGSGGSG GSGGSGGSGS S                                31

SEQ ID NO: 38          moltype = AA  length = 29
FEATURE                Location/Qualifiers
REGION                 1..29
                       note = Synthetic Sequence
source                 1..29
                       mol_type = protein
                       organism = synthetic construct
SEQUENCE: 38
GGSGGSGGSG GSGGSGGSGG SGGSGGSGS                                   29

SEQ ID NO: 39          moltype = AA  length = 585
FEATURE                Location/Qualifiers
source                 1..585
                       mol_type = protein
                       organism = Homo sapiens
SEQUENCE: 39
DAHKSEVAHR FKDLGEENFK ALVLIAFAQY LQQCPFEDHV KLVNEVTEFA KTCVADESAE  60
NCDKSLHTLF GDKLCTVATL RETYGEMADC CAKQEPERNE CFLQHKDDNP NLPRLVRPEV  120
DVMCTAFHDN EETFLKKYLY EIARRHPYFY APELLFFAKR YKAAFTECCQ AADKAACLLP  180
KLDELRDEGK ASSAKQRLKC ASLQKFGERA FKAWAVARLS QRFPKAEFAE VSKLVTDLTK  240
VHTECCHGDL LECADDRADL AKYICENQDS ISSKLKECCE KPLLEKSHCI AEVENDEMPA  300
DLPSLAADFV ESKDVCKNYA EAKDVFLGMF LYEYARRHPD YSVVLLLRLA KTYETTLEKC  360
CAAADPHECY AKVFDEFKPL VEEPQNLIKQ NCELFEQLGE YKFQNALLVR YTKKVPQVST  420
PTLVEVSRNL GKVGSKCCKH PEAKRMPCAE DYLSVVLNQL CVLHEKTPVS DRVTKCCTES  480
LVNRRPCFSA LEVDETYVPK EFNAETFTFH ADICTLSEKE RQIKKQTALV ELVKHKPKAT  540
KEQLKAVMDD FAAFVEKCCK ADDKETCFAE EGKKLVAASQ AALGL                 585

SEQ ID NO: 40          moltype = AA  length = 625
FEATURE                Location/Qualifiers
source                 1..625
                       mol_type = protein
                       organism = Homo sapiens
SEQUENCE: 40
MIFLYQVVHF ILFTSVSGEC VTQLLKDTCF EGGDITTVFT PSAKYCQVVC TYHPRCLLFT  60
FTAESPSEDP TRWFTCVLKD SVTETLPRVN RTAAISGYSF KQCSHQISAC NKDIYVDLDM  120
KGINYNSSVA KSAQECQERC TDDVHCHFFT YATRQFPSLE HRNICLLKHT QTGTPTRITK  180
LDKVVSGFSL KSCALSNLAC IRDIFPNTVF ADSNIDSVMA PDAFVCGRIC THHPGCLFFT  240
FFSQEWPKES QRNLCLLKTS ESGLPSTRIK KSKALSGFSL QSCRHSIPVF CHSSFYHDTD  300
FLGEELDIVA AKSHEACQKL CTNAVRCQFF TYTPAQASCN EGKGKCYLKL SSNGSPTKIL  360
HGRGGISGYT LRLCKMDNEC TTKIKPRIVG GTASVRGEWP WQVTLHTTSP TQRHLCGGSI  420
IGNQWILTAA HCFYGVESPK ILRVYSGILN QSEIKEDTSF FGVQEIIIHD QYKMAESGYD  480
IALLKLETTV NYTDSQRPIC LPSKGDRNVI YTDCWVTGWG YRKLRDKIQN TLQKAKIPLV  540
TNEECQKRYR GHKITHKMIC AGYREGGKDA CKGDSGGPLS CKHNEVWHLV GITSWGEGCA  600
QRERPGVYTN VVEYVDWILE KTQAV                                       625

SEQ ID NO: 41          moltype = AA  length = 638
FEATURE                Location/Qualifiers
source                 1..638
                       mol_type = protein
                       organism = Homo sapiens
SEQUENCE: 41
MILFKQATYF ISLFATVSCG CLTQLYENAF FRGGDVASMY TPNAQYCQMR CTFHPRCLLF  60
SFLPASSIND MEKRFGCFLK DSVTGTLPKV HRTGAVSGHS LKQCGHQISA CHRDIYKGVD  120
MRGVNFNVSK VSSVEECQKR CTNNIRCQFF SYATQTFHKA EYRNNCLLKY SPGGTPTAIK  180
VLSNVESGFS LKPCALSEIG CHMNIFQHLA FSDVDVARVL TPDAFVCRTI CTYHPNCLFF  240
TFYTNVWKIE SQRNVCLLKT SESGTPSSST PQENTISGYS LLTCKRTLPE PCHSKIYPGV  300
DFGGEELNVT FVKGVNVCQE TCTKMIRCQF FTYSLLPEDC KEEKCKCFLR LSMDGSPTRI  360
AYGTQGSSGY SLRLCNTGDN SVCTTKTSTR IVGGTNSSWG EWPWQVSLQV KLTAQRHLCG  420
GSLIGHQWVL TAAHCFDGLP LQDVWRIYSG ILNLSDITKD TPFSQIKEII IHQNYKVSEG  480
NHDIALIKLQ APLNYTEFQK PICLPSKGDT STIYTNCWVT GWGFSKEKGE IQNILQKVNI  540
PLVTNEECQK RYQDYKITQR MVCAGYKEGG KDACKGDSGG PLVCKHNGMW RLVGITSWGE  600
GCARREQPGV YTKVAEYMDW ILEKTQSSDG KAQMQSPA                         638

SEQ ID NO: 42          moltype = AA  length = 25
FEATURE                Location/Qualifiers
REGION                 1..25
                       note = Synthetic Sequence
source                 1..25
                       mol_type = protein
                       organism = synthetic construct
SEQUENCE: 42
CTTKIKPRIV GGTASVRGEW PWQVT                                       25

SEQ ID NO: 43          moltype = AA  length = 13
FEATURE                Location/Qualifiers
```

-continued

```
REGION                    1..13
                          note = Synthetic Sequence
source                    1..13
                          mol_type = protein
                          organism = synthetic construct
SEQUENCE: 43
GGGGSPRIGG GGS                                                    13

SEQ ID NO: 44             moltype = AA   length = 26
FEATURE                   Location/Qualifiers
REGION                    1..26
                          note = Synthetic Sequence
source                    1..26
                          mol_type = protein
                          organism = synthetic construct
SEQUENCE: 44
VCTTKTSTRI VGGTNSSWGE WPWQVS                                      26

SEQ ID NO: 45             moltype = AA   length = 7
FEATURE                   Location/Qualifiers
REGION                    1..7
                          note = Synthetic Sequence
source                    1..7
                          mol_type = protein
                          organism = synthetic construct
SEQUENCE: 45
STRIVGG                                                           7

SEQ ID NO: 46             moltype = AA   length = 81
FEATURE                   Location/Qualifiers
source                    1..81
                          mol_type = protein
                          organism = Saccharomyces cerevisiae
SEQUENCE: 46
MRFPSIFTAV LFAASSALAA PVNTTTEDET AQIPAEAVIG YSDLEGDFDV AVLPFSNSTN  60
NGLLFINTTI ASIAAKEEGV S                                           81

SEQ ID NO: 47             moltype = AA   length = 24
FEATURE                   Location/Qualifiers
source                    1..24
                          mol_type = protein
                          organism = Homo sapiens
SEQUENCE: 47
MKWVTFISLL FLFSSAYSRG VFRR                                        24

SEQ ID NO: 48             moltype = AA   length = 20
FEATURE                   Location/Qualifiers
source                    1..20
                          mol_type = protein
                          organism = Homo sapiens
SEQUENCE: 48
MSRELAPLLL LLLSIHSALA                                             20
```